(12) United States Patent
Yoon et al.

(10) Patent No.: US 9,074,980 B2
(45) Date of Patent: Jul. 7, 2015

(54) METHOD FOR THE TOXICITY ASSESSMENTS OF NANO-MATERIALS

(75) Inventors: Tae-Hyun Yoon, Seoul (KR); Song-Hee Lee, Seoul (KR); Dong-Wook Kwon, Seoul (KR); Jong-Hoon Park, Seoul (KR); Hyun-Ju Yoo, Seoul (KR); Hyun-Woo Nho, Seoul (KR)

(73) Assignee: INDUSTRY-UNIVERSITY CORPORATION FOUNDATION HANYANG UNIVERSITY, Seoul (KR)

( * ) Notice: Subject to any disclaimer, the term of this patent is extended or adjusted under 35 U.S.C. 154(b) by 0 days.

(21) Appl. No.: 13/278,716

(22) Filed: Oct. 21, 2011

(65) Prior Publication Data

US 2012/0219985 A1 Aug. 30, 2012

(30) Foreign Application Priority Data

Jan. 20, 2011 (KR) .................. 10-2011-0005971
Mar. 7, 2011 (KP) .................. 10-2011-0019857
May 11, 2011 (KR) .................. 10-2011-0043947

(51) Int. Cl.

| C12Q 1/18 | (2006.01) |
| G01N 21/64 | (2006.01) |
| G01N 21/29 | (2006.01) |
| G01N 15/14 | (2006.01) |
| G01N 15/04 | (2006.01) |
| G01N 33/50 | (2006.01) |
| B82Y 5/00 | (2011.01) |
| B82Y 35/00 | (2011.01) |

(Continued)

(52) U.S. Cl.
CPC ............ *G01N 15/1475* (2013.01); *G01N 15/04* (2013.01); *G01N 15/147* (2013.01); *G01N 15/1484* (2013.01); *G01N 21/6458* (2013.01); *G01N 21/648* (2013.01); *G01N 33/5014* (2013.01); *G01N 2015/0038* (2013.01); *G01N 2015/0092* (2013.01); *G01N 2015/1075* (2013.01); *G01N 2015/1486* (2013.01); *G01N 2015/1497* (2013.01); *G01N 2510/00* (2013.01)

(58) Field of Classification Search
None
See application file for complete search history.

(56) References Cited

U.S. PATENT DOCUMENTS

2006/0216238 A1* 9/2006 Manchester et al. ......... 424/9.34
2011/0115895 A1* 5/2011 Huisken ......................... 348/79

OTHER PUBLICATIONS

Alkilany et al., Toxicity and cellular uptake of gold nanoparticles: what we have learned so far?, J. Nanopart. Res. (2010) 12:2313-2333.*

(Continued)

*Primary Examiner* — Karen Cochrane Carlson
*Assistant Examiner* — Jennifer M. H. Tichy
(74) *Attorney, Agent, or Firm* — Fitch, Even, Tabin & Flannery, LLP

(57) ABSTRACT

The present invention relates to a method for the toxicity assessment of nano-materials, and more specifically, it is relates to an objective, reproducible and accurate assessment method for the unbiased toxicity testings of nano-materials, which minimize artifacts of the conventional methods for the toxicity assessment of the nano-materials by considering the dose characteristics of the nano-material itself using Selective multi-Plane Illumination Microcopy (SPIM); and the response characteristics of the nano-material using the improved or novel cellular responses assessment methods for nano-materials (e.g., modified MTT assay using image cytometric analysis, normal-inverted exposure apparatus, and modified flow cytometry), and a system and an apparatus thereof.

9 Claims, 42 Drawing Sheets

(51) Int. Cl.
G01N 15/00 (2006.01)
G01N 15/10 (2006.01)

(56) References Cited

OTHER PUBLICATIONS

Dhawan et al., Toxicity assessment of nanomaterials: methods and challenges, Anal. Bioanal. Chem. (2010) 398:589-605.*
Friedrich et al., Detection of single quantum dots in model systems with sheet illumination microscopy, J. Fluorecs, Published online Oct. 6, 2011.*
Garini et al., From micro to nano: recent advances in high-resolution microscopy, Current Opinion in Biotechnology (2005) 16:3-12.*
Hillegass et al., Assessing nanotoxicity in cells in vitro, WIREs Nanomedicine and Nanobiotechnology, vol. 2, May/Jun. 2010.*
Huisken et al., Even fluorescence excitation by multidirectional selective plane illumination microscopy (mSPIM), Optics Letters, vol. 32, No. 17, Sep. 1, 2007.*
Huisken et al., Selective plane illumination microscopy techniques in developmental biology, Development 136, 1963-1975 (2009).*
Ntziachristos, Going deeper than microscopy: the optical imaging frontier in biology, Nature Methods, vol. 7, No. 8, Aug. 2010.*
Reynaud et al., Meeting report: First light sheet based fluorescence microscopy workshop, Biotechnology Journal (2010) 5: 798-804.*
Weber et al., Light sheet microscopy for real-time developmental biology, Current Opinion in Genetics & Development, (2011) 21:566-572 (.*
Weber et al., Omnidirectional microscopy, Nature Methods, vol. 9, No. 7, Jul. 2012.*
Zeiss, Education in Microscopy and Digital Imaging, accessed Jan. 21, 2014, online at: zeiss-campus.magnet.fsu.edu/articles/basics/care.html.*
Friedrich et al., Detection of single quantum dots in model organisms with sheet illumination microscopy, Biochemical and Biophysical Research Communications, 390 (2009) 722-727.*
Teeguarden, Justin G. et al., "Particokinetics In Vitro: Dosimetry Considerations for In Vitro Nanoparticle Toxicity Assessments", Toxicological Sciences, 95(2), 2007, pp. 300-312.
Laaksonen, Timo et al., "Failure of MTT as a Toxicity Testing Agent for Mesoporous Silicon Microparticles", Chem. Res. Toxicol, 20, 2007, pp. 1913-1918.
Marquis, Bryce J. et al., "Analytical methods to assess nanoparticle toxicity", www.rsc.org/analyst, Analyst., 134, 2009, pp. 425-439.
Worle-Knirsch, J.M. et al., "Oops They Did It Again! Carbon Nanotubes Hoax Scientists in Viability Assays", Nano Letters, vol. 6, No. 6, 2006, pp. 1261-1268.

* cited by examiner

Schematics of experiment by HILO illumination for detection of nanoparticle

Schematics of experiment by TIR illumination for detection of nanoparticle

Au$^{BBI15}$          Au$^{BBI30}$          SiO$_2$$^{F515-50}$

METHOD FOR THE TOXICITY ASSESSMENTS OF NANO-MATERIALS

TECHNICAL FIELD

The present disclosure relates to a method for the toxicity assessment of nano-materials, more specifically, it relates to an objective and accurate method for the toxicity assessment of nano-materials, which reduces the error of conventional methods for the toxicity assessment of the nano-materials by considering the characteristics of the nano-materials themselves in a cell using a Selective Plane Illumination Microscopy (SPIM) method; and the cellular responsiveness assessment to the nano-materials using flow cytometry, image cytometry, a normal and inverted exposure apparatus and the like, and a system and an apparatus therefor.

BACKGROUND

The toxicity of nano-sized materials (hereinafter, nano-materials) which can be generated when the nano-materials are exposed to a human body is emerging as a new problem according to recent dramatic development of nano-technology. In consideration of the gradual increase in frequency of breath inhalation, oral inhalation and skin exposure, accurate and scientific information about nano-technology and the stability of nano-materials is urgently being requested.

The toxicity of nano-materials results from their very small size and nano-material-specific physicochemical characteristics which are largely different from a bulk-material. The toxicity such as the possibility of inducing cancer from materials having acicular structure, such as asbestos and glass fibers, has been already known for a long time. Unlike asbestos and glass fiber, the toxicity of nano-materials resulting from their very small size as well as their morphological characteristics is receiving more attention. It has been reported that high surface reactivity and cell membrane permeability allow the nano-materials to be easily introduced into a living body, enhance the possibility of inducing cellular level stress, and can further have a continuous effect by accumulating in a living body, like asbestos. It is considered that nano-materials, unlike micro-sized materials, can be deposited in the body by penetrating deeply into the body so as to cause cardiovascular diseases, and particularly, that nano-materials penetrating through a nasal nerve can move in the body by blood so as to also cause brain damage.

Most of nano-material toxicity studies conducted on living bodies are conducted by injection using syringe or cell culture, and mainly with metals, metal oxides, carbon nano-materials and the like. In general, it is known that nano-particles are introduced into a human body by the respiratory system, mouth and skin, rather than by injection.

It is time that international co-operation should be actively pushed ahead to prevent the potential harmful effects of nano-materials in advance and to make provisions for nano-materials, and an institutional strategy should be simultaneously prepared to minimize or reduce potential dangers, such as indiscriminate development and application of nano-technology, and improper disposal of nano-materials.

However, the toxicity of nano-particles and the like affecting a human body or environment may be serious, and a method to assess the actual influence of the exposure of nano-materials on the human body and environment has not been properly established yet.

Up to now, generally, the toxicity assessment method used for existing chemicals has been applied to nano-materials in many cases. However, the smaller the particle size is, the wider the surface area is so as to increase the responsiveness to living tissue and the toxicity caused thereby. Therefore, an investigation into the new physical and chemical properties of nano-materials considering the nano-sized characteristics and the toxicity caused thereby is critical.

Therefore, in order to assess the toxicity of nano-materials, there is a need to study their unique characteristics and problems, and the potential causes of their behavior, exposure and toxicity.

Recently, the direct exposure of consumers to nano-materials is dramatically increasing because many products using nano-materials are produced in various industrial fields, and many of them are consumed. Accordingly, the toxicity of nano-materials is being studied worldwide, and the importance of the development of a method for the toxicity assessment of nano-materials is also magnified. A supplemental platform for the cellular toxicity assessment of nano-materials is needed by developing a protocol, which can solve the problems arising in conventional nano-material toxicity assessments, and by developing a new instrument for nano-material toxicity assessment.

Therefore, the present inventors found that a more objective assessment of the toxicity of nano-materials is possible by analyzing characteristics of the nano-materials themselves, such as concentration (number), size, distribution and the like, using Selective Plane Illumination Microscopy (SPIM); analyzing influences (reactivity) of nano-materials on a cell using flow cytometry, image cytometry, a normal and inverted exposure apparatus and the like in sequence; and combining the results.

SUMMARY

Accordingly, an object of the present invention is to provide a method for the toxicity assessment of nano-materials using Selective multi-Plane Illumination Microscopy (mSPIM), a system therefor, and a device therefor.

Another object of the present invention is to provide a method for the toxicity assessment of nano-materials comprising the dose characteristics assessment of the nano-materials themselves using Selective Plane Illumination Microscopy (SPIM), and the sequential cellular responsiveness assessment to the nano-materials; a system therefor; and a device therefor.

Further, another object of the present invention is to provide a method and device using image cytometry and a normal and inverted exposure apparatus to assess the cellular responsiveness as a specific embodiment of the nano-material toxicity assessment system.

In order to solve the problems, the present invention provides a method or system for the toxicity assessment of nano-materials comprising the steps of: 1) assessing the dose characteristics of the nano-materials themselves using Selective multi-Plane Illumination Microscopy (mSPIM); 2) assessing the cellular responsiveness to the nano-materials; and 3) combining the results of the assessed dose characteristics of the nano-materials and the cellular responsiveness to the nano-materials.

The dose characteristics of the nano-materials themselves include characteristics such as concentration (number) and the size (hydrodynamic size) distribution of the nano-materials dispersed in a cell medium, agglomeration and sedimentation coefficients of the nano-materials in a cell medium, cellular uptake of the nano-materials; and the like.

In this case, the measurement of the concentration (number) of the nano-materials dispersed in a cell medium is conducted in real time through nano-material image analysis, preferably, and the analysis of the size distribution of the nano-materials dispersed in a cell medium is conducted by measuring diffusion coefficient D according to Brownian movement of the nano-materials in real time through analysis of video or continuously shot images of the nano-materials:

$$D=kT/(6\pi\eta r),$$

wherein, k is Boltzmann constant, T is temperature, $\eta$ is solution viscosity and r is the radius of a nano-material.

The calculation of the agglomeration coefficient and sedimentation coefficient of nano-materials in the cell medium can be performed by measuring the concentration and the size distribution of the nano-materials at 2 or more sample heights using mSPIM of PLS (parallel light sheet) mode, and the calculation of the cellular uptake of the nano-materials can be conducted by measuring the concentration and the size distribution of the nano-materials actually exposed; and the concentration and the size distribution of the nano-materials accumulated in a cell.

In this case, to calculate the cellular uptake of the nano-materials, for example, SPIM of PLS (parallel light sheet) mode; and the combination of SPIMs of HILO (highly inclined and laminated optical sheet) mode or TIR (total internal reflection) mode can be used.

And, the cellular responsiveness to the nano-materials can be confirmed by measuring a link between the nano-materials and apoptosis, and the step of assessing cellular responsiveness to the nano-materials is conducted by using a staining method, flow cytometry, image cytometry, analysis using a normal and inverted exposure apparatus and the like. A detailed explanation thereof will be separately provided later.

In another form, the present invention provides a device for the toxicity assessment of nano-materials. A diagram of the device is represented in FIG. 3.

The device for the toxicity assessment of nano-materials comprises a device equipped with mSPIM consisting of a laser light source, a cylindrical lens reducing the laser beam thickness and an objective lens, an objective lens placed perpendicular thereto and focusing fluorescent light, and a detector; and a device measuring cellular responsiveness to nano-materials, and is intended to sequentially measure the nano-material characteristics and cellular responsiveness using the said devices, respectively.

Particularly, the mSPIM can consist of a laser-based dark field fluorescent microscope illustrated in FIG. 4, and the mSPIM is bound to a nano-material exposure device. In this case, the nano-material exposure device may comprise a microfluidic chip or an exposure apparatus for well plates produced by using poly(dimethylsiloxane) (PDMS), polymethylmethacrylate (PMMA), polyacrylates, polycarbonates, polycyclic olefins, polyimides, or polyurethanes, preferably.

The mSPIM can be (i) a combination of two or more SPIMs of PLS (parallel light sheet) mode; or (ii) a combination of SPIM of PLS (parallel light sheet) mode with SPIM of HILO (highly inclined and laminated optical sheet) mode or TIR (total internal reflection) mode, and when the combination (i) of two or more SPIMs is utilized, the distribution of the size (hydrodynamic size) according to sample height and agglomeration coefficient in a cell medium can be measured, and when the combination (ii) of two or more SPIMs is utilized, the cellular uptake of nano-particles can be measured.

The device of the present invention for the toxicity assessment of nano-materials may be equipped with a device for measuring cellular responsiveness to the nano-materials, for example, a flow cytometer, an image cytometer, a normal and inverted exposure apparatus and the like.

Therefore, in another form, the present invention provides a method for the toxicity assessment of nano-materials comprising the steps of analyzing the dose characteristics of nano-materials using Selective Multi-Plane Illumination Microscopy (mSPIM), and analyzing the cellular responsiveness to the nano-materials using image cytometry.

The image cytometry can consist of cell morphology analysis, fluorescence image analysis or absorption image analysis, and comprises quantification of the degree of apoptosis.

In this case, the fluorescence image analysis can use an organic fluorescent dye, an inorganic nano-particle or a fluorescent protein, and the absorption image analysis can use an absorption dye selected from a group consisting of MTT (3-(4,5-dimethyl thiazol-2-yl)-2,5-diphenyltetrazolium bromide)), MTS (5-(3-caroboxymeth-oxyphenyl)-2H-tetra-zolium inner salt), WST (4-[3-(4-Iodophenyl)-2(4-nitrophenyl)-2H-5-tetrazolio]1,3-benzene disulfonate) and trypan blue.

The quantification of the degree of apoptosis can be conducted by analyzing at least one selected from a group consisting of: the value of the morphology factor selected from a group consisting of occupied area per cell and circularity; or at least one fluorescent intensity or absorbance per cell selected from a group consisting of mean fluorescent intensity or absorbance per cell; and integrated fluorescent intensity or absorbance per cell, from the filmed images, wherein:

$$\text{circularity}=4\pi\times(\text{cell area/cell perimeter}^2);$$

mean fluorescent intensity or absorbance per cell
=mean of fluorescent intensities or absorbances of each fixel in a cell region;
integrated fluorescent intensity or absorbance per cell
=mean fluorescent intensity or absorbance per cell×number of fixel occupied by a cell.

Further, in another form, the present invention provides a method for the toxicity assessment of nano-materials comprising the steps of analyzing the dose characteristics of the nano-materials using Selective Multi-Plane Illumination Microscopy (mSPIM), and analyzing the cellular responsiveness to the nano-materials using a normal and inverted exposure apparatus. In this case, it is preferable to conduct image cytometry additionally.

The normal and inverted exposure apparatus may comprise a microfluidic chip or an exposure instrument for well plates produced by using at least one polymer material selected from a group consisting of poly(dimethylsiloxane (PDMS), polymethylmethacrylate (PMMA), polyacrylates, polycarbonates, polycyclic olefins, polyimides and polyurethanes, and the inverted exposure apparatus can be utilized to make the cultured cell layer face down so as to be exposed to the nano-materials, and used to the concentration correction of the exposed nano-materials.

Thus, the present invention provides a method, which can directly measure the quantitative and the size distribution of nano-particles in real-time by sequentially performing the desired analyses, respectively; can reduce errors resulting from the heterogeneity of the nano-particles, which is generated in the existing in-vitro nano-particles exposure test by monitoring the agglomeration coefficient of the nano-particles in a cell medium, and the cellular uptake of the nano-particles and the like; and further assess the dose-response relation of the nano-particles more accurately and reproducibly by selectively assessing only the direct toxic effects of the nano-materials.

In the toxicity assessment of nano-materials, the present invention suggests various problems, which result from the use of existing protocols for assessing the toxicity of chemicals, and also suggests solutions or improvements in areas where experimenters make many mistakes.

Particularly, in order to reduce errors, the dose characteristics of the nano-materials, such as concentration (number), the size and distribution, are analyzed, sequentially, the influence of the nano-materials on a cell (reactivity) is analyzed, and then the results are combined to obtain a more accurate result for the toxicity analysis.

Therefore, a platform for the toxicity assessment of nano-materials based on the present invention can be produced so as to obtain more accurate and reproducible results in future toxicity assessments of nano-materials.

DETAILED DESCRIPTION

Figure 1A:
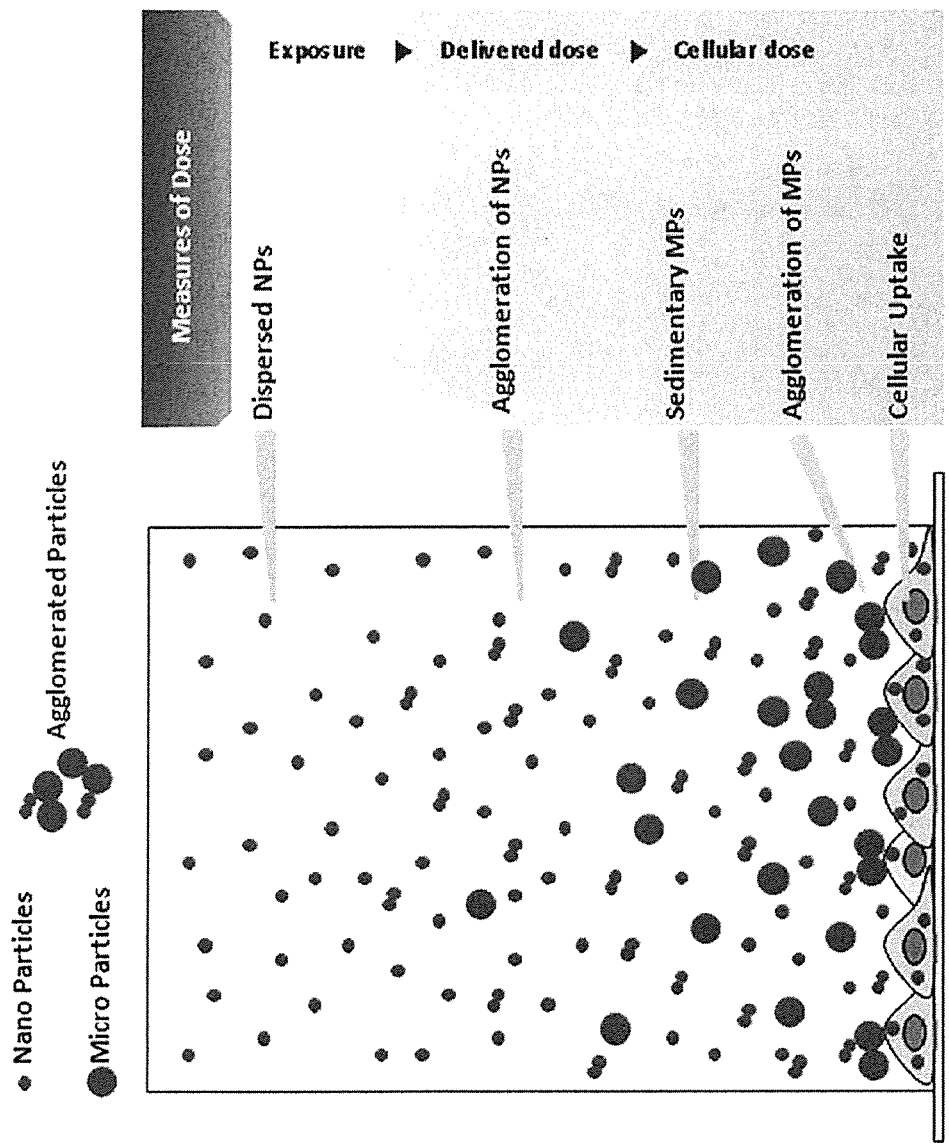
FIG. 1: diagrams representing a process showing errors by the concentration change according to agglomeration and sedimentation when nano-particles are actually exposed to cell culture solution [Justin G. Teeguarden et al., 2007].

The terms used in the present invention are defined as follows.

"Nano-material" refers to a nano-particle and nano-structure material wherein the length of at least one dimension among the three dimensions in the size of the particle is smaller than 100 nm. Particularly, in the present invention, nano-material is used in combination with the term nano-particle.

"Nano-particle" refers to a particle having a diameter of 1 to 100 nm.

"Toxicity of nano-material" is a generic term for the danger, risk, hazard, toxicity and the like of a nano-sized particle or liquefied material. More specifically, the hazard refers to a material or behavior which can cause a disturbance, i.e., a source of risk, and the risk is defined as the probability or likelihood of the occurrence of harmful results to a person or group exposed to a certain concentration or dose of a harmful material. In the OECD, the risk is defined as [Risk=Hazard×Exposure].

In general, it is a problem that the smaller the particle is, the higher the responsiveness, and the toxicity to a living body can increase with increasing surface. Particularly, some nano-materials, which can penetrate into animal cells, can pass through cell membranes or the blood-brain barrier, and they may unintentionally affect cell or tissues. Therefore, there is a need to study nano-material toxicity and prepare safety control guidelines and the like. According to references, the nano-material toxicity examinations of carbons, silica, $TiO_2$ and silver nano-particles are sequentially underway.

"Tissue or cell sample" refers to a similar cell aggregate obtained from a tissue of a subject or patient. A source of the tissue or cell sample may be a fresh, frozen and/or conserved organ or tissue sample; or a solid tissue from a biopsy or aspirate; blood or any blood cell; a cell at any point during pregnancy or development of a subject. The tissue sample may also be a primary or cultured cell, or cell line.

"Apoptosis" is used in its broad meaning, and generally means a cell death following the rule of a mammal or controlled cell death, which involves at least one characteristic cell change including cytoplasm compression, loss of plasma membrane microvilli, karyokinesis, chromosomal DNA degradation or mitochondrial dysfunction.

In the present invention, "monitoring" or "real-time assessment" refers to a systematic detection of variables effective for a certain period of time (Traxler. 1997). Namely, it is to find out what is changed to what and how it is changed for a certain period time. There are two kinds of monitoring: one is a regular monitoring method using a limitation or standard, or indicator as a criterion for effectiveness verification, and the other is an irregular monitoring method, as a meaning of "surveillance", which does not set a qualitative standard value before examination (observation). In the present invention, the term "monitoring" is being used in combination with the term "assessment".

Unless otherwise indicated in the present disclosure, "comprise" and "comprising" include a suggested step or element, or a group of steps or elements, but it should be understood not to exclude any other step or element, or group of steps or elements.

Unless otherwise defined, all technical terms used in the present invention are used consistent with what a skilled person in the art related to the present invention generally understands. Further, preferred methods or samples are listed in the present invention, but also similar or equivalent methods or samples are included in the scope of the present invention.

Hereinafter, the present invention is described in detail.

The present invention relates to a method for the toxicity assessment of nano-materials (nano-particles).

The nano-materials of interest may be any nano-particles and nano-structure materials wherein the length of at least one dimension among a particle's three dimensions is smaller than 100 nm. Any such nano-materials can be included in the scope of the present invention without limitation, and for example, they may be materials listed in Table 1. Gold nano, silver nano, SWCNT (single-walled carbon nanotube), MWCNT (multi-walled carbon nanotube), fullerene (C60), iron, nano-particles, carbon black, titanium dioxide, aluminum oxide, cerium oxide, zinc oxide, silicon dioxide, polystyrene, dendrimer, nano-clay and the like may be utilized, and in one example of the present invention, gold nano-particles or titanium dioxides were used.

In order to figure out and understand the danger (toxicity) of nano-materials due to exposure, first of all, tone must understand the physical and chemical characteristics of the nano-materials, the physical behavior thereof, and the cell physiological in vivo function thereof.

TABLE 1

| No. | Materials |
|---|---|
| 1 | Silver nanoparticles |
| 2 | Single-walled carbon nanotubes (SWCNTs) |
| 3 | Multi-walled carbon nanotubes (MWCNTs) |
| 4 | Fullerenes (C60) |
| 5 | Iron nanoparticles |
| 6 | Carbon black |
| 7 | Titanium dioxide |
| 8 | Aluminium oxide |
| 9 | Cerium oxide |
| 10 | Zinc oxide |
| 11 | Silicon dioxide |
| 12 | Polystyrene |
| 13 | Dendrimers |
| 14 | Nanoclays |

Because different nano-materials have somewhat different characteristics, in the present invention, firstly, the dose characteristics of the nano-materials themselves, for example, the concentration (number) and the size (hydrodynamic size) distribution of the nano-materials dispersed in a cell medium; agglomeration and sedimentation coefficients of the nano-materials in a cell medium; cellular uptake of the nano-materials; and the like are analyzed, and additionally, the actual influence of the nano-materials on a cell (for example, association with apoptosis), namely, the cellular responsiveness to the nano-materials is analyzed. The nano-materials have various concentrations by being diffused in cells in a time-dependent manner, and then the cells in a cell layer are exposed to the nano-materials for a certain period of time so as to undergo apoptosis. The actual influence of the nano-materials on the cells can be analyzed by figuring out the link between apoptosis and the nano-materials.

Cellular responsiveness is divided into apoptosis, necrosis and the like. Because exposure to the hazardous material causes cell deterioration and changes to normal cell division, the cellular responsiveness mechanism to the hazardous material can be confirmed by searching for metabolic processes different from that of normal cells, i.e., the cell death (cell deterioration) process. Herein, the cell death process is classified into two processes, and one of them is a cell death process called "necrosis", wherein intracellular contents are released due to cell swelling and cell lysis. Further, the other cell process called "apoptosis" is characterized by early cell shrinkage, and refers to the destruction of cell-cell bonds with nearby cells. In the apoptosis process, cell volume is reduced, and the inner membranes in the cytoplasm, ribosome, glomerulus and other cell organelles are shrunken.

The toxicity assessment of the nano-material currently used is conducted by using a conventional in vitro cellular-based toxicity assessment system. Namely, the method, wherein cells are cultured at the bottom of a petri dish or multiwell plate, and the cells are exposed to nano-materials, followed by analyzing the degree of cell growth or apoptosis by a cell analysis method using various fluorescent and absorption dyes, has been used to measure the cellular toxicity of nano-materials, but this conventional method results in many errors.

When assessing the toxicity of nano-materials, a significant in determining the concentration occurs in the measurement of the amount of the cell-exposed nano-materials, i.e., the nano-material exposure dose.

Accurate measurement of the "nano-material exposure dose (e.g., particle number, particle size distribution, particle surface area, total amount and the like)" is not easy with general methods, and the reproducibility of the result of the toxicity assessment may significantly deteriorate due to the surroundings, such as a preparation method of nano-material dispersion, exposure time or medium and the like, because they involve many changes in the particle size and the concentration according to the medium conditions after exposure. For example, when nano-materials are dispersed in a cell medium, the nano-materials are agglomerated and sedimented in several hours due to the high ionic strength of the cell culture solution before the cells are cultured. Therefore, in the case of an in vitro test method using surface-mounted cells, the concentration of the nano-particles actually exposed may have a greater difference in the particle number and distribution than that of the nano-materials initially injected.

As a general method to measure the particle size of the nano-materials dispersed in aqueous solution, dynamic light scattering (DLS) is used, but it requires samples of several ml or more, and it is difficult to accurately measure the particle size distribution when particles having various sizes are mixed. As mentioned above, when the nano-particles are exposed to a cell culture solution, a method to simultaneously measure the size distribution of the particles from several nanometers to several micrometers is needed because the particles can grow to several micrometers, and a method to measure the concentration change of the nano-particles exposed to the cells in real-time is needed.

Further, because the toxicity caused by the agglomerated and sedimented particles and the toxicity caused by the nano-particles well dispersed in a cell medium may be different in their mechanism of toxicity, and because there is a strong likelihood of assessing the nano-material toxicity to be greater than the actual toxicity of the nano-particles due to the heterogeneity of the nano-particles, wherein the higher concentration of the nano-particles is distributed as the particles move down to the bottom of the well plate compared with the actual toxicity of the nano-particles due to "agglomeration and sedimentation", these causes of error should be clearly distinguished. As one example, when there is agglomeration and sedimentation, there is an excess concentration of the nano-particles around the cells compared to the injected concentration of the nano-particles because the nano-particles are distributed heterogeneously in a solution. Thus, the overestimate of nano-particle toxicity is a significant error in the nano-particle toxicity assessment system currently being used.

To address these issues, hereinafter, examples of modifying the conventional methods according to the specific methods are described in detail.

First of all, examples of conventional techniques relevant to the present invention are as follows.

UV/VIS spectrometer: as the similar conventional technique with the present invention, the change of optical density caused by the scattering or uptake of nano-particles is measured using a UV/VIS spectrometer to quantify the concentration of the nano-particles dispersed in a solution. This spectrometer can determine the concentration of the nano-particle-containing sample for analysis by measuring the amount of penetrated light while changing the wavelength range of the light from UV to visible light. It is possible that the higher the concentration of the sample for analysis, the lower the penetration ratio of the light absorbed or scattered by the sample for analysis.

Dynamic light scattering (DLS): nano-particles put in the path of light scatter the light. The intensity of the scattered light is changed by the Brownian movement of the nano-particles in a time-dependent manner. Because the dispersed particles in a solution move faster as the particle size thereof become smaller, the changing rate of the scattered light also becomes faster. Using this property, the diffusion coefficient can be obtained by applying an autocorrelation function, and from this, the hydrodynamic size of the particles can be obtained. In general, the distribution of the nano-particles provided from the DLS analysis method is provides information regarding number, volume and intensity. The intensity is the strength of the signal produced during the DLS measurement, the volume is changed to the distribution volume, and the number graph represents the distribution of the particle number. The intensity graph has the advantage of showing the distribution of the particles having various sizes, but also has the disadvantages that the micro-sized particles seem to really occupy most of the distribution because of the high signal per unit particle. On the other hand, the number graph has the advantage of showing the distribution of the particle number, but also has the disadvantage that the graph is drawn almost excluding the micro-size particles.

TEM (transmission electron microscopy): TEM is a representative device which can analyze the morphology of a nano-material such as size, shape, and surface condition. In order to analyze the primary size (the size of each particle before the agglomeration) of the nano-particles, a sufficient number of representative TEM images of the nano-particles are obtained, and then the size distribution can be analyzed using an image analysis program.

XRD (X-ray diffraction): XRD makes it possible to experimentally measure the crystal phase and the size of powder-type nano-particles. Particularly, the minimum crystal size of nano-particles can be calculated using the Scherrer formula. For example, the diffracted X-ray is spread out with decreasing crystal size (<0.2 μm). Full width at half maximum (FWHM) of the peak of the diffracted X-ray is measured to quantify the degree of dispersion, and therefore, the particle size can be estimated.

ICP-MS (inductively coupled plasma mass spectrometry): in trace element analysis methods of chemical analysis, the weight method, color-developing method, atomic absorption spectrophotometry, X-ray fluorometry, atomic emission spectroscopy and the like are developed, and among them, now, ICP-AES (inductively coupled plasma atomic emission spectroscopy) is the most widely used method for analysis. The ICP-MS (inductively coupled plasma mass spectroscopy, hereinafter, called ICP-MS) uses high-temperature plasma as a source for analysis like the ICP-AES, and both have the advantages of simultaneous analysis of multi-elements and short analysis time in common. However, the ICP-MS is able to analyze smaller amounts of elements because it has a lower detection limit from tens to thousands times than ICP-AES. These analysis methods are mainly used to decide the total amount of the nano-particles.

Namely, up to now, in order to observe the change of the cells exposed to nano-particles, the concentration of the nano-particle solution has been analyzed using the UV/VIS spectrometer or ICP-MS before exposing thereof to the cell culture solution, and the size distribution thereof has been analyzed using the DLS or TEM.

[Problem]

However, these methods may cause the following problems.

Figure 1B:
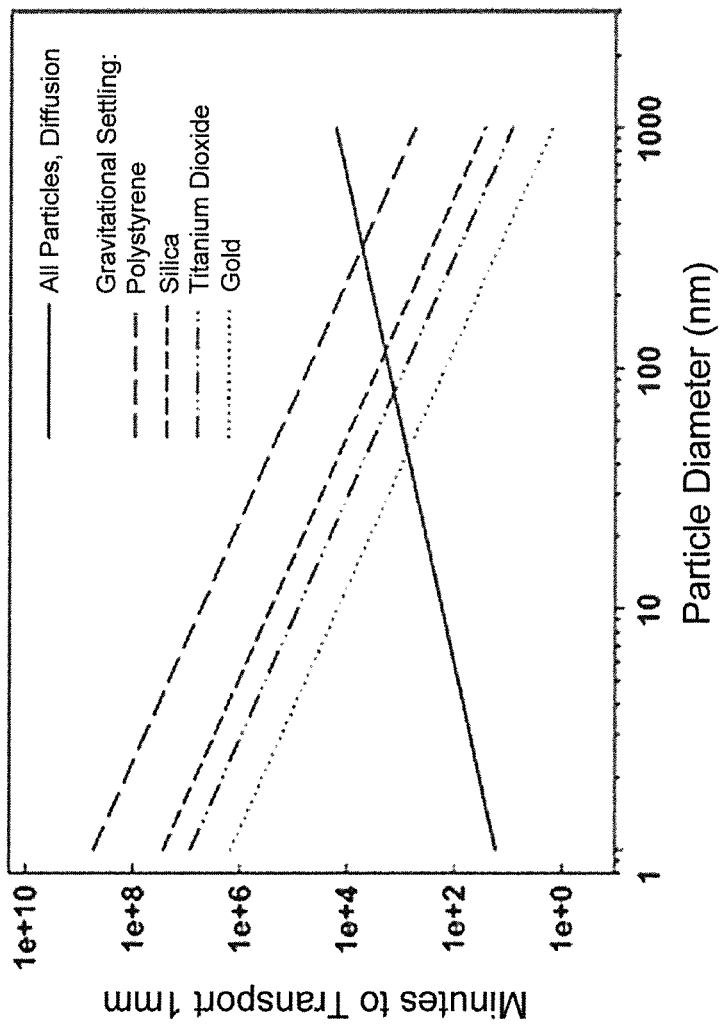
Figure 1C:
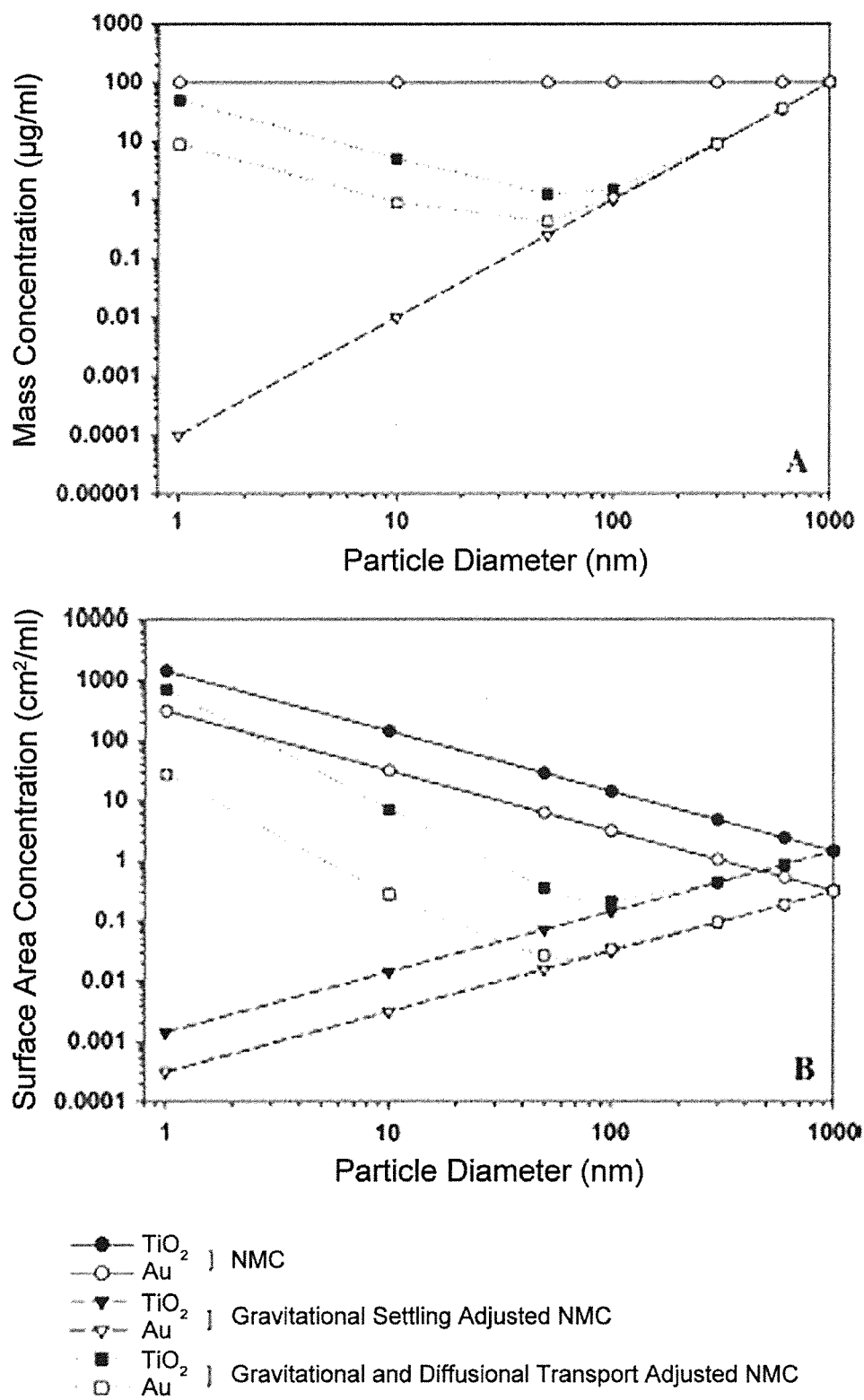

(1) Concentration Heterogeneity in Medium Caused by Agglomeration and Sedimentation of Nano-Particles When nano-particles, which are widely used industrially and generally prepared, are dispersed in a cell medium (e.g., RPMI-1640, DMEM), most of the nano-particles are agglomerated and sedimented by the high ionic strength of the cell medium as shown in FIG. 1.

The result of the toxicity assessed by the conventional in vitro-based assessment method, wherein the cells are cultured at the bottom of a well plate and exposed to the toxic materials, may be the result of the toxicity assessment of the sedimented micro-size particles but not the toxicity of the nano-particles. The cytotoxicity caused by the sedimented particles after the agglomeration may be different from that actually caused by the nano-particles in the toxicity mechanism, and the toxicity can be overestimated relative to the actual toxicity of the nano-particles due to the heterogeneity of the nano-particles distributed with a higher concentration at the bottom of the well plate, and therefore, the causes of these errors should be addressed.

Further, the concentration of the nano-particles is higher around the cells than the concentration of the injected nanoparticles because the nano-particles are heterogeneously distributed in a solution when the particles are agglomerated and sedimented. The resulting overestimate of the nano-particle toxicity is one of the most significant errors of the nano-particle toxicity assessment system currently used.

Namely, there is a need to develop a method, which can measure the concentration change of the nano-particles in real-time to show the cellular responsiveness while solving the errors caused by agglomeration and sedimentation, but the quantitative relation between nano-particles and cellular responsiveness is difficult to obtain because conventional methods are performed without considering the concentration change due to agglomeration and sedimentation.

(2) Error Caused by the Optical or Catalytic Characteristics of Nano-Particles

Further, when apoptosis is assessed by general spectrometry when the prepared nano-particles are sedimented, incorrect cellular toxicity assessments may result from the error caused by absorption, luminescence, scattering and the like of the sedimented nano-particles.

An example of such errors can be seen in the MTT assay. The MTT assay is a test method using an ability of mitochondria, which reduces MTT tetrazolium, a yellow aqueous substrate to blue-purple non-aqueous MTT formazan by the function of a dehydrogenase, and it is widely used to test the toxicities of various chemicals. Because this technique can obtain reproducible optical concentration with minimum physical treatment, it is widely used as a method to measure the cell activity. However, fatal errors may be generated in the analysis result when abiotic factors outside of the cell affect the reduction process of the tetrazolium salts.

For example, the absorbance value may be changed according to the change of pH, adducts (serum, cholesterol, ascorbic acid salt) of the cell culture solution (Marquis et al, Analyst, 2009, 134, 425-439). Further, recently, several studies about nano-materials reported that there may be errors in measuring apoptosis due to the interaction of cellular toxicity staining material such as MTT with carbon-based material such as SWCNTs and others. It was recently reported that the interaction between MTT and SWCNTs is induced due to their properties, wherein the reduced MTT formazan is not dissolved out by a solvent because it is attached to the surface of the SWCNTs (Worle-Knirsch et al, Nano Lett 2006, 6, 1028-33). And Laaksonen et al. reported that the oxidation reaction on the surface of PSi nano-particles becomes a cause of the MTT reduction reaction, and the MTT can be reduced directly. Therefore, performing a toxicity test with PSi particle ingredients using an MTT assay has limitations (Laaksonen et al. Chem. Res. Toxicol. (2007)). These errors in the existing MTT assay mostly result from the interactions, such as the reduction of MTT to MTT-formazan, with abiotic causes existing outside of the cell.

(3) Limit of the Conventional Nano-Particle Analysis Method

Because use of the UV/VIS spectrometer to measure the concentration of nano-materials measures the change in optical density caused by the scattering or uptake of nano-particles, quantification of the measured value may decrease when the scattering or absorption characteristics are changed by the change in the kind of nano-particles or in aqueous solution (e.g., agglomeration, surface change and the like).

ICP-MS is an analysis method to detect the total amount of the subject element present in a sample, and therefore, there is a problem that the materials (e.g., ions dissolved from the particles), which are the same as the actual nano-particles and present with different shapes in a solution, are detected simultaneously with the actual nano-particles being analyzed, so as to be difficult to be distinguished.

In the case of DLS, when particles having various sizes are in the solution at the same time, information regarding the small particles cannot be obtained easily because scattered light from the large particles is significant, and solution having low concentrations cannot be easily measured.

The particle size analysis using TEM or XRD provides the size information of the nano-particles, but it is only measured in the dried powder state, and therefore, the information of the nano-particles actually dispersed in the solution cannot be accurately confirmed. The assumption that the sample condition has been changed due to the pre-treatment process cannot be excluded. Further, because the pre-treatment process is required, it is difficult to detect the size change of the nano-particles in real-time, and because the obtained images only show an extremely small part of the total sample, the problem of representativeness also arises.

Therefore, an objective of the present invention is to provide a method, which can compensate for the previously reported problems in nano-toxicity assessment by minimizing the errors caused by exposure dose agglomeration, sedimentation and the like to the nano-particles actually accumulated in a cell in the cellular toxicity assessment, and by measuring and interpreting the influence of the nano-particles on cell growth or death in real-time.

Regarding this matter, in the present invention, we want to reduce the errors in two main ways.

In order to analyze nano-material toxicity, first of all, the present invention analyzes the dose characteristics of the nano-materials themselves which influence cells.

Namely, the factors of the error caused by the changes in the concentration and the size of the nano-materials, which are generated when the nano-materials are agglomerated in a cell culture solution, are removed. For example, the concentration (number) and the size (hydrodynamic size) distribution of the nano-materials dispersed in a cell medium; the agglomeration and sedimentation coefficients of the nano-materials in a cell medium; and the cellular uptake of the nano-materials are analyzed to select only the cellular responsiveness affected by the nano-particles. For this, a method and device using Selective multi-Plane Illumination Microscopy (mSPIM) are used.

Next, the actual influence of the nano-materials on the cells is analyzed by measuring cellular responsiveness.

In order to objectively analyze the direct influence of the nano-materials on apoptosis and the like, the present invention removes the errors in the existing apoptosis analysis method caused by indirect toxic factors, for example, the errors caused by the heterogeneity of the nano-particles in an aqueous solution resulting from agglomeration and sedimentation or the errors caused by optical or catalytic reactivity of the nano-particles, so as to selectively assess only the direct toxic effects of the nano-materials.

For this, after the mSPIM analysis, the cellular responsiveness to the nano-materials are measured using, in sequence, a staining method, flow cytometry, image cytometry, analysis using a normal and inverted exposure apparatus and the like. In one embodiment of the present invention, the image cytometry and the normal and inverted exposure apparatus are used.

Thus, in the present invention, the nano-material toxicity can be objectively and accurately assessed by combining the results of selectively choosing and analyzing the cells reacting with the nano-materials with respect to the concentration and the size of the nano-materials using mSPIM; and the result of sequentially analyzing the cellular responsiveness by observing the degree of apoptosis to the nano-materials.

Figure 2:
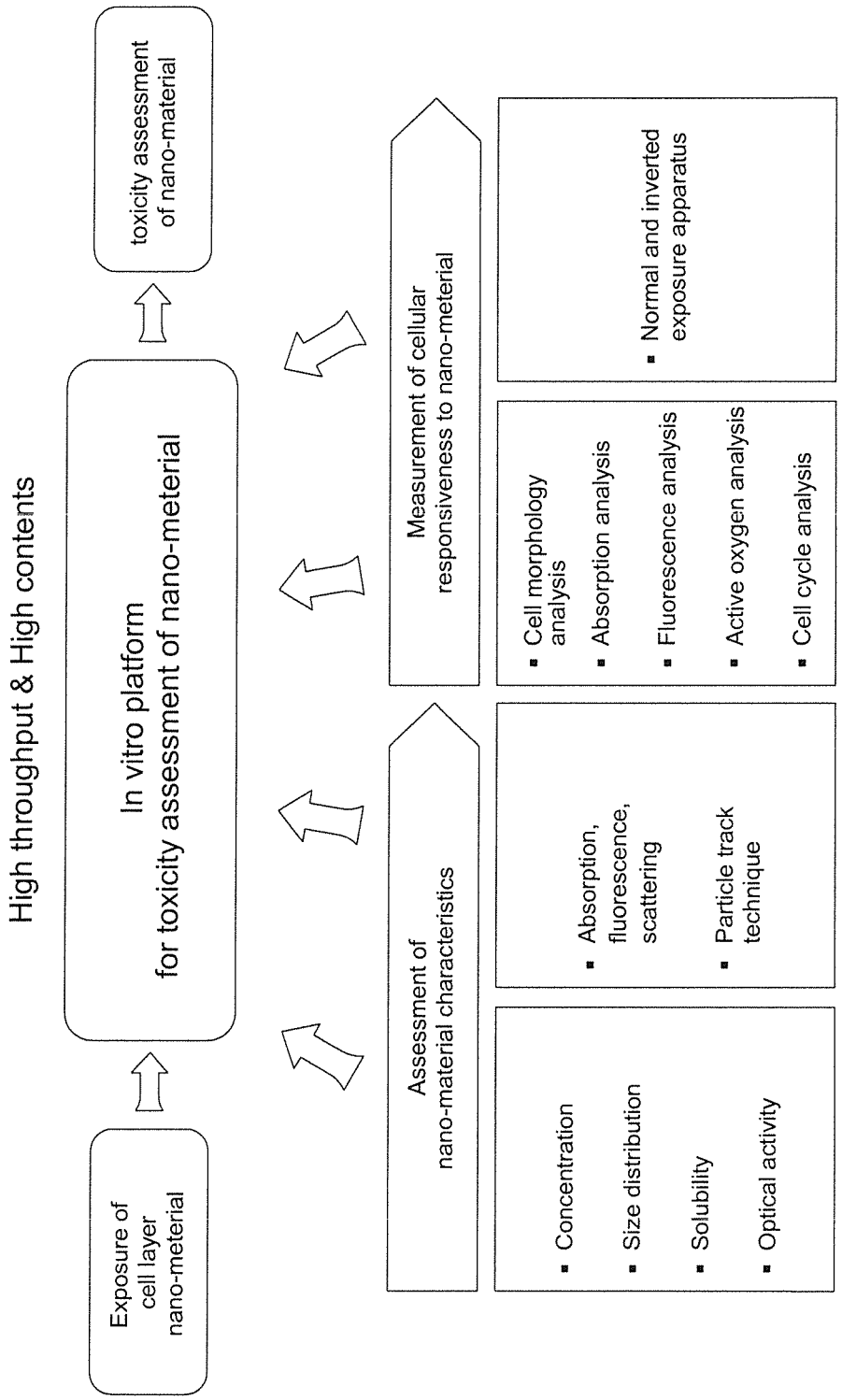
FIG. 2: a concept map of an in vitro platform for the toxicity assessment of nano-materials.

Therefore, one aspect of the present invention relates to a method or system for the toxicity assessment of nano-materials comprising the steps of: 1) assessing the dose characteristics of the nano-materials themselves using Selective multi-Plane Illumination Microscopy (mSPIM); 2) assessing the cellular responsiveness to the nano-materials; and 3) combining the results of the assessed dose characteristics of the nano-materials and the cellular responsiveness to the nano-materials, and a device therefor. A concept map of an in vitro platform for the toxicity assessment of the nano-materials is shown in FIG. 2.

[Analysis Using a SPIM-Nano-Material Dose Characteristics Assessment]

First of all, the present invention is characterized by analyzing the dose characteristics of the nano-materials themselves, which influence the cells, using Selective multi-Plane Illumination Microscopy (mSPIM).

In order to accurately analyze the nano-material toxicity, errors resulting from the changes in the concentration (number) and the size distribution by the agglomeration of the nano-materials in a cell culture solution can be removed by using mSPIM. Namely, the cellular response due to the nano-particles can be determined by analyzing the concentration (number) and the size (hydrodynamic size) distribution of the nano-materials dispersed in a cell medium; the agglomeration and sedimentation coefficients of the nano-materials in a cell medium; and the cellular uptake of the nano-materials.

In the case of general chemicals, intracellular delivery by diffusion is a main process because there is no agglomeration or sedimentation, but in the case of nano-materials, which can be agglomerated or sedimented, the concentration heterogeneity of the nano-materials by the sedimentation and passive intracellular delivery can be important influences in the nano-material toxicity assessment. Further, in comparison with the conditions in the organs of a living body, such as blood vessels and the like, when the heterogeneous nano-particles are assessed with conventional methods only considering the cells at the bottom plane, distorted toxicity results are obtained because cells are three-dimensionally distributed in up-and-down and left-and-right directions.

FIG. 1 is disclosed in a paper issued in 2007 by Justin G. Teeguarden et al., and it is reported that because the concentration of the nano-particles is changed due to agglomeration and sedimentation when the nano-particles are actually exposed to a cell culture medium, errors may occur if the cellular responsiveness of the nano-particles is quantified only with the initial exposure concentration. Further, it shows that the diffusion and sedimentation rates are different according to the size of the nano-particles, and therefore, the concentration heterogeneity may depend on the height of the measurement. Therefore, in the case of cells cultured at the bottom of the medium, the cellular responsiveness can depend more on the influence of the sedimentation of the nano-particles.

To solve these problems, in the present invention, the concentration homogeneity change of the nano-particles in an aqueous solution caused by the agglomeration and sedimentation of the nano-particles is corrected in real-time using a nano-particle real-time monitoring device combined with Selective multi-Plane Illumination Microscopy (mSPIM), and the dose of the nano-particles delivered from the cell medium to the cells (delivered & cellular dose) and the amount of the nano-materials accumulated in the cells (cellular uptake of NPs) are measured in real-time. Therefore, the present invention solves the errors generated when the dose actually delivered to the cell medium and the cells (delivered & cellular dose) is measured.

At this time, mSPIM can be combined according to this purpose.

For example, (i) a combination of two or more SPIMs of PLS (parallel light sheet) mode, or (ii) a combination of SPIM of PLS (parallel light sheet) mode with SPIM of HILO (highly inclined and laminated optical sheet) mode or TIR (total internal reflection) mode can be used. When the combination (i) of two or more SPIMs is utilized, it is intended to measure the agglomeration coefficient in a cell medium according to the sample height, and when the combination (ii) of two or more SPIMs is utilized, it is intended to measure the cellular uptake of nano-particles.

The method or system using the Selective multi-Plane Illumination Microscopy (mSPIM) of the present invention may comprise the following processes as one specific example:

exposing the nano-materials to the cell medium;

measuring the concentration (number) and the size distribution of the nano-materials dispersed in the cell medium using Selective multi-Plane Illumination Microscopy (mSPIM);

calculating the agglomeration and sedimentation coefficients of the nano-materials in the cell medium;

calculating the cellular uptake of the nano-materials in the cells; and analyzing the results.

In the above method, first of all, the subject cells are cultured in a cell medium, and the nano-materials are exposed to the cell medium. Regarding the conditions and methods for cell culture, any common methods known in the art can be used.

The apoptosis is induced by exposing the nano-materials to the cultured cell medium. The exposure of the nano-materials to the cell medium can be performed using a common nano-material exposure device.

For example, a microfluidic chip or an exposure instrument for well plates produced by using a polymer material such as poly(dimethylsiloxane) (PDMS), polymethylmethacrylate (PMMA), polyacrylates, polycarbonates, polycyclic olefins, polyimides, polyurethanes and the like can be used.

In one embodiment of the present invention, a PDMS structure was made and used as a sample holder. Particularly, in the present invention, the sample holder containing the nano-particle solution therein is prepared to have the size which has a smaller dose than the existing sample holder having a volume of several ml so as to inhibit the flow of the solution by convection and surrounding vibration. This reduces the movement of the nano-particles by factors other than the Brownian movement when the nano-particles dispersed in a solution are observed using laser-based dark field and fluorescent microscopes.

More preferably, the surface of the sample holder can be coated to reduce the scattering at the wall. For example, the irregular reflection due to the roughness of the PDMS surface can be improved and made more smoothly and transparently by applying a coat of a pre-polymer solution prepared by diluting PDMS in n-hexane to the PDMS holder.

Further, the quantitative and size analysis of the nano-materials dispersed in the microfluidic chip can be analyzed by combining the sample holder with a channel of the existing microfluidic chip. In this case, the combination can be conducted by mounting a Teflon structure on a master mold of the microfluidic chip followed by repeating the existing method for preparing the microfluidic chip, or by preparing a PDMS microfluidic chip layer and a PDMS layer using the Teflon structure, respectively, followed by attaching the two layers to each other under the condition of oxygen plasma.

The mSPIM can be equipped to the nano-material exposure apparatus. An analyzer equipped with the SPIM may comprise, for example, as described in FIG. 4, a laser-based dark field fluorescent microscope.

And, the present invention has the following technical characteristics:

the thickness of the laser beam is primarily reduced by an iris and slit;

the beam shape is changed to a plate shape by a cylindrical lens; and an image having a high-resolution and high-contrast ratio with minimum background noise can be obtained because the scattering or fluorescent signal of the particles outside of the beam path can be excluded by decreasing the beam thickness up to several micrometers due to secondary reduction of the beam thickness by the objective lens.

Figure 4:
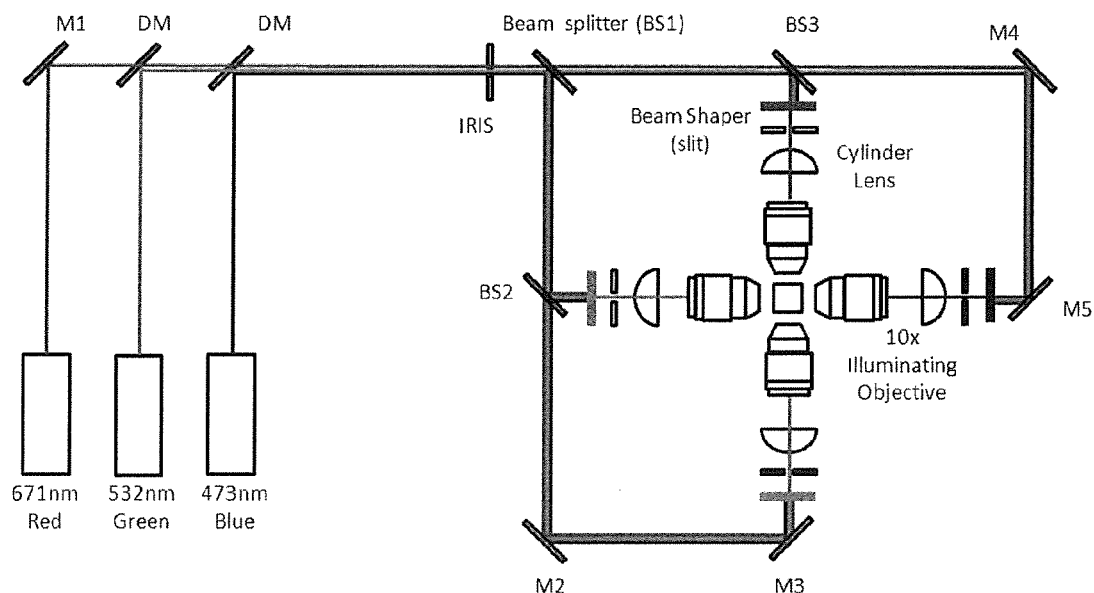
FIG. 4: a schematic diagram of a laser spectroscopy system which can use a SPIM method used in the present invention.
Figure 4:
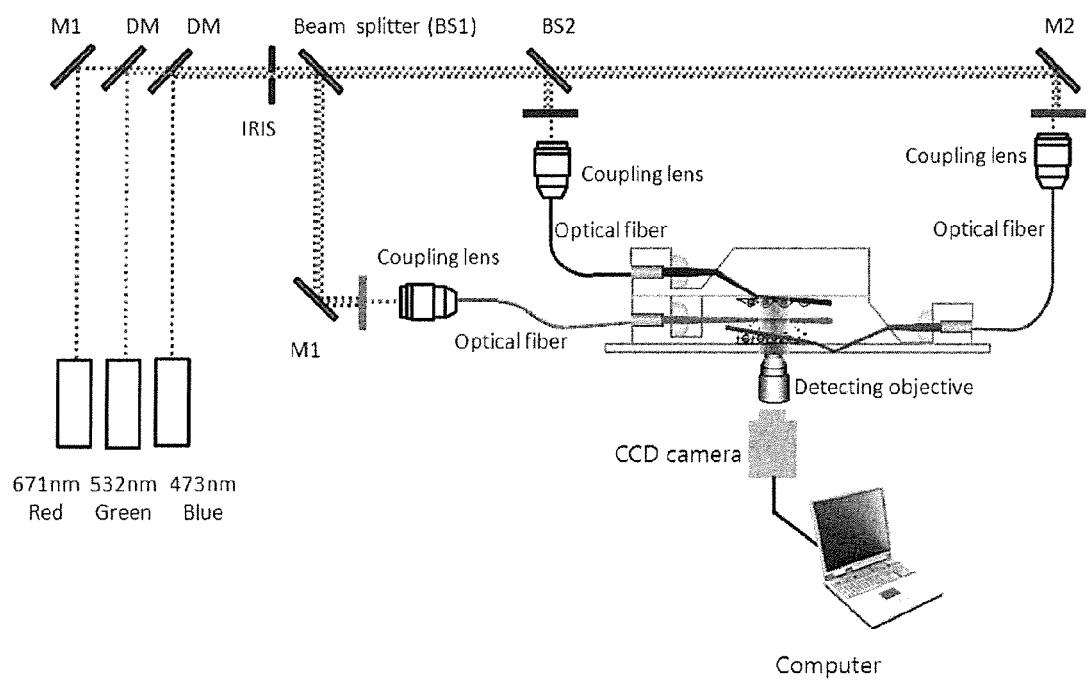

FIG. 4 illustrates a schematic diagram of a laser spectroscopy system which can use a SPIM method of the present invention.

The laser can be irradiated in various directions, and can be formed thin and wide by an iris, slit, cylindrical lens, objective lens and the like. Further, the incidence angle to the sample also can be changed by a prism. The scattering and fluorescence generated from the sample can be collected by a detecting objective lens (omitted from the FIGs) and CCD camera, and then saved to images.

The concentration of the nano-particles in a solution can be quantitatively measured by directly counting the number of nano-particles dispersed in the solution by a scattering or fluorescence method using a laser, and the size distribution of the nano-particles can be analyzed in real-time by measuring the distance of the Brownian movement of the nano-particles per unit time.

Therefore, in another embodiment, the present invention provides a device for analyzing the characteristics of the nano-materials, which is equipped with two or more SPIMs consisting of a laser light source, a cylindrical lens reducing the laser beam thickness and an objective lens, an objective lens placed perpendicular thereto and focusing fluorescent light, and a nano-material detector.

In the present invention, the size and the number of nano-materials dispersed in a cell medium is measured using mSPIM.

In this case, the measurement of the number of nano-materials dispersed in a cell medium can be conducted by nano-material image analysis in real time. The image analysis can be conducted by using video or continuously shot images. For example, the image analysis using imageJ can be used.

And, the size distribution of nano-materials dispersed in a cell medium is analyzed by using diffusion coefficient D according to Brownian movement of the nano-materials through the image analysis of video or continuously shot images of the nano-materials:

$$D=kT/(6\pi\eta r),$$

wherein, k is the Boltzmann constant, T is temperature, $\eta$ is solution viscosity and r is radius of nano-materials (nano particles).

In order to measure the size change of the nano-particles dispersed in a cell medium in real-time, the nano-particle images (collection of video or continuously shot images) are analyzed, and then the diffusion coefficient D of Brownian movement nano-particles can be measured from mean-square-displacements (MSD), mean-square of the moving distance, of the nano-particles. The size of the nano-particles can be calculated by substituting into the stoke-einstein formula.

Next, the agglomeration and sedimentation coefficients of the nano-materials in a cell medium, and the cellular uptake of the nano-materials are calculated.

The calculation of the agglomeration and sedimentation coefficients of the nano-materials in a cell medium can be conducted by measuring the concentration and the size distribution of the nano-materials at 2 or more sample heights in the cell medium using mSPIM of PLS (parallel light sheet) mode.

Namely, the agglomeration and sedimentation coefficients of the nano-material in a cell medium can be calculated by measuring the changes in the number and the size of the nano-particles, and then measuring the rate changes in the number and the size of the nano-particles due to the agglomeration and sedimentation.

At this time, the particle number as well as the particle size increase over time at the part having a lower observed height, but the particle number decreases by agglomeration and sedimentation of the particles over time at the part having a higher observed height, and only the smaller sized particles remain.

On the other hand, the calculation of the cellular uptake of the nano-materials can be conducted by measuring the concentration and the size distribution of the nano-materials actually exposed, and the concentration and the size distribution of the nano-materials accumulated in a cell.

In this case, the calculation can be conducted by using SPIM of PLS (parallel light sheet) mode, and the combination of SPIMs of HILO (highly inclined and laminated optical sheet) mode or TIR (total internal reflection) mode. Through this mSPIM combination, the cellular uptake of the nano-materials can be calculated by measuring the concentration and the size distribution of the actually exposed nano-materials, and the concentration and the size distribution of the nano-materials accumulated in the cells. In this case, whether the particles are accumulated in the cell can be determined at a point when the movements are slowing down by tracking the Brownian movement particles.

The cells are cultured at a lower plane of the sample holder, and when the nano-particles dispersed in the culture solution are exposed, the actual cellular uptake of the nano-particles to the cells may be different from the initial cellular uptake of the nano-particles thereto because the nano-particles are agglomerated and sedimented depending on the conditions of the culture solution. Therefore, in order to measure the actual cellular uptake of the nano-particles to the cells, a laser light source in the form of HILO can be introduced. The cellular uptake of the nano-particles can be measured in the HILO form wherein the laser is irradiated with refraction by passing through the prism to the bottom plane, and at the same time, the nano-particles dispersed in the PLS form can be observed in the middle of the sample.

Thus, the dose characteristics of the nano-materials themselves can be assessed by analyzing the relation of the cellular responsiveness to the particles actually taken up by the cells, based on the calculation of the agglomeration and sedimentation coefficients of the nano-materials in a cell medium and the calculation of the cellular uptake of the nano-materials using SPIM.

[Cellular Responsiveness Analysis]

In the present invention, after analyzing the characteristics of the nano-materials using mSPIM, cellular responsiveness to the nano-materials is sequentially assessed. The cellular responsiveness analysis to the nano-materials can be performed by confirming the association of the nano-materials with apoptosis.

The method of cellular responsiveness analysis to the nano-materials, which can be used, is not limited, but a staining method, flow cytometry, image cytometry, analysis using a normal and inverted exposure apparatus and the like can be used.

Figure 13:
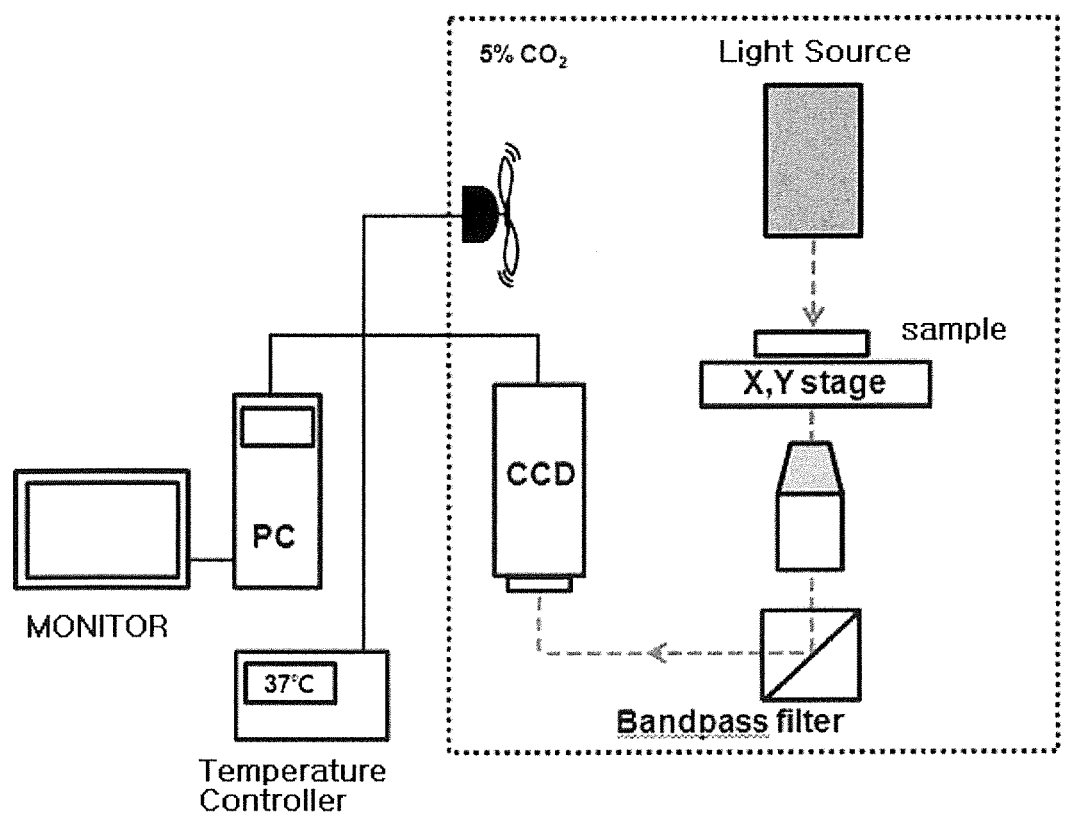
FIG. 13: a schematic diagram of image cytometry.

For example, the apoptosis can be analyzed quantitatively using image cytometry. A schematic diagram of the image cytometry is illustrated in FIG. 13.

At this time, regarding image cytometry, any conventional method can be used, such as cell morphology analysis, fluorescence image analysis or absorption image analysis, without limitation. Particularly, regarding analysis using the improved absorption image analysis of each cell, Korean patent application No. 10-2009-0133151 can be referred to.

For example, organic fluorescent dyes such as DCF, DiOC6, Hoechest 33432 and the like; inorganic nano-particles such as quantum dot (QD) and the like; or fluorescent proteins such as GFP, RFP, YFP and the like can be used for the fluorescence image analysis, and absorption dyes selected from a group consisting of MTT (3-(4,5-dimethyl thiazol-2-yl)-2,5-diphenyltetrazolium bromide)), MTS (5-(3-carboxymeth-oxyphenyl)-2H-tetra-zolium inner salt), WST (4-[3-(4-Iodophenyl)-2(4-nitrophenyl)-2H-5-tetrazolio]1,3-benzene disulfonate) and trypan blue can be used for the absorption image analysis.

The quantification of the degree of apoptosis is conducted by analyzing the value of the morphology factor selected from a group consisting of the occupied area per cell and circularity; mean fluorescent intensity or absorbance per cell; and integrated fluorescent intensity or absorbance per cell, from the filmed images, wherein $$circularity = 4\pi \times (cell\ area/cell\ perimeter^2);$$

mean fluorescent intensity or absorbance per cell=mean of fluorescent intensities or absorbances of each fixel in a cell region;

integrated fluorescent intensity or absorbance per cell=mean fluorescent intensity or absorbance per cell×number of fixel occupied by a cell.

In the step of quantifying the degree of apoptosis, parameters comprising the fluorescence intensity or absorbance per cell obtained from image analysis were independently subjected to univariate analysis to obtain a dose-responsiveness curve, and the degree of apoptosis progression was quantified. These results of the quantitative analysis of apoptosis can be combined, and therefore, the relation of the cellular responsiveness to the particles actually taken up by the cells can be analyzed.

Figure 14:
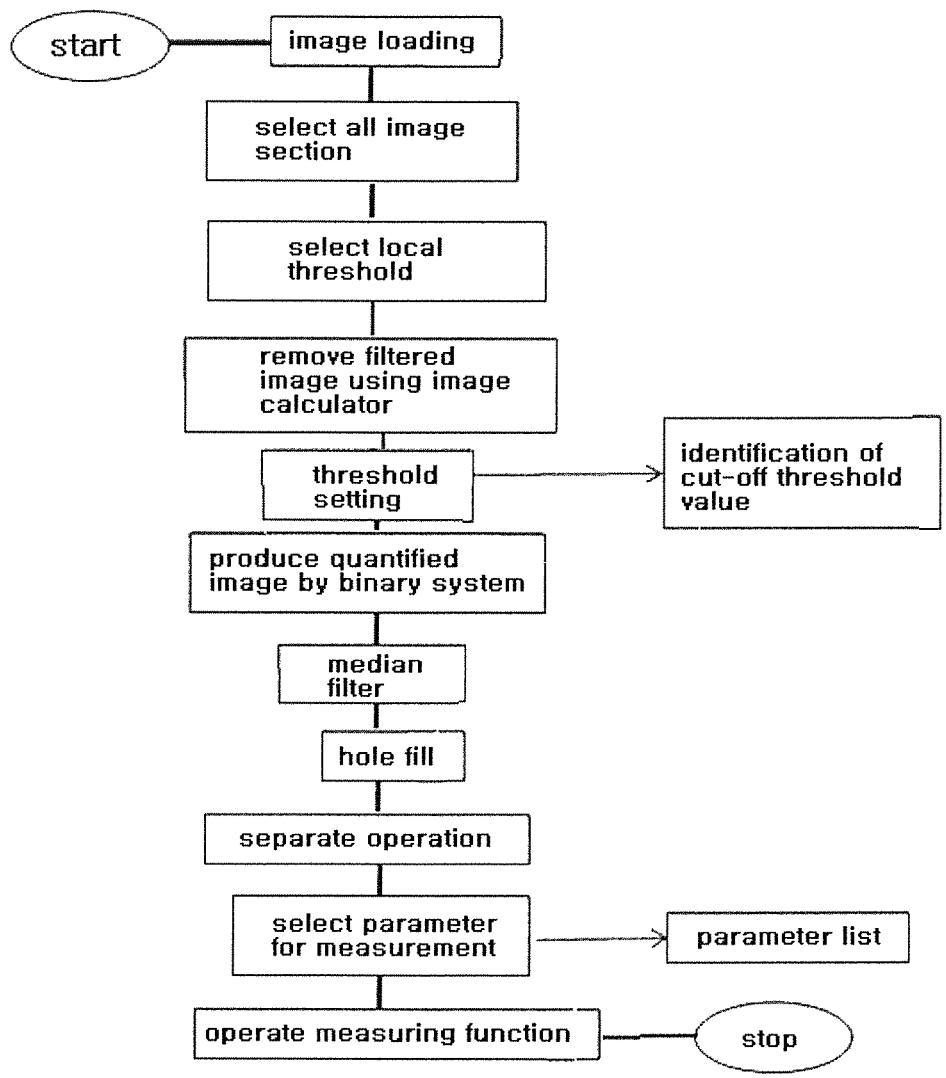
FIGS. 14 to 16: flow charts of processes performing the cell image analysis according to the cell morphology analysis and the results of one example thereof.
Figure 15:
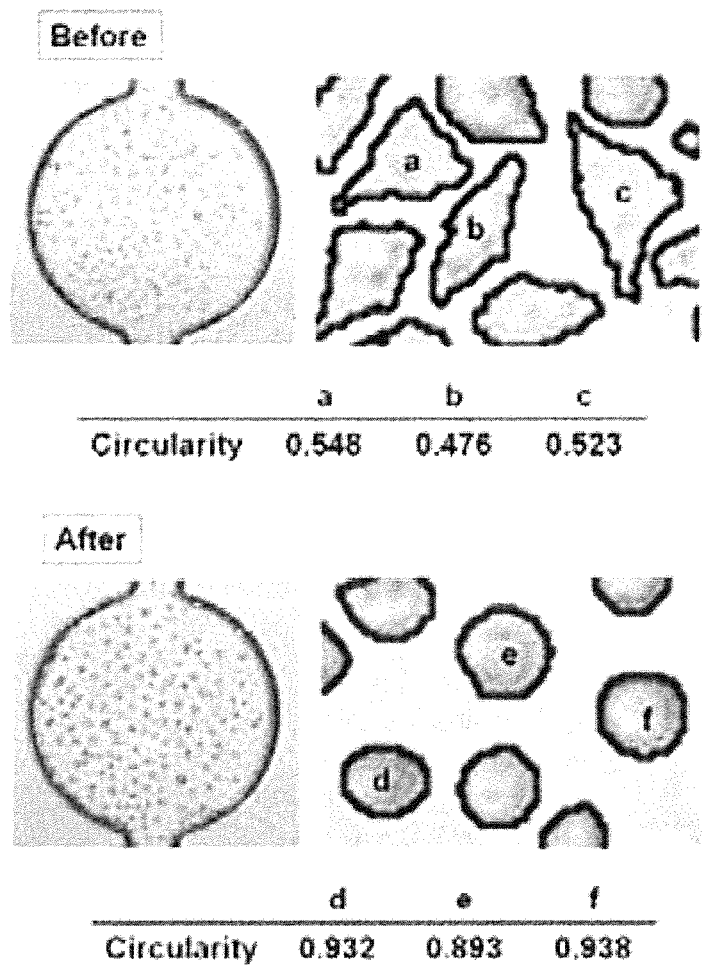
Figure 16:
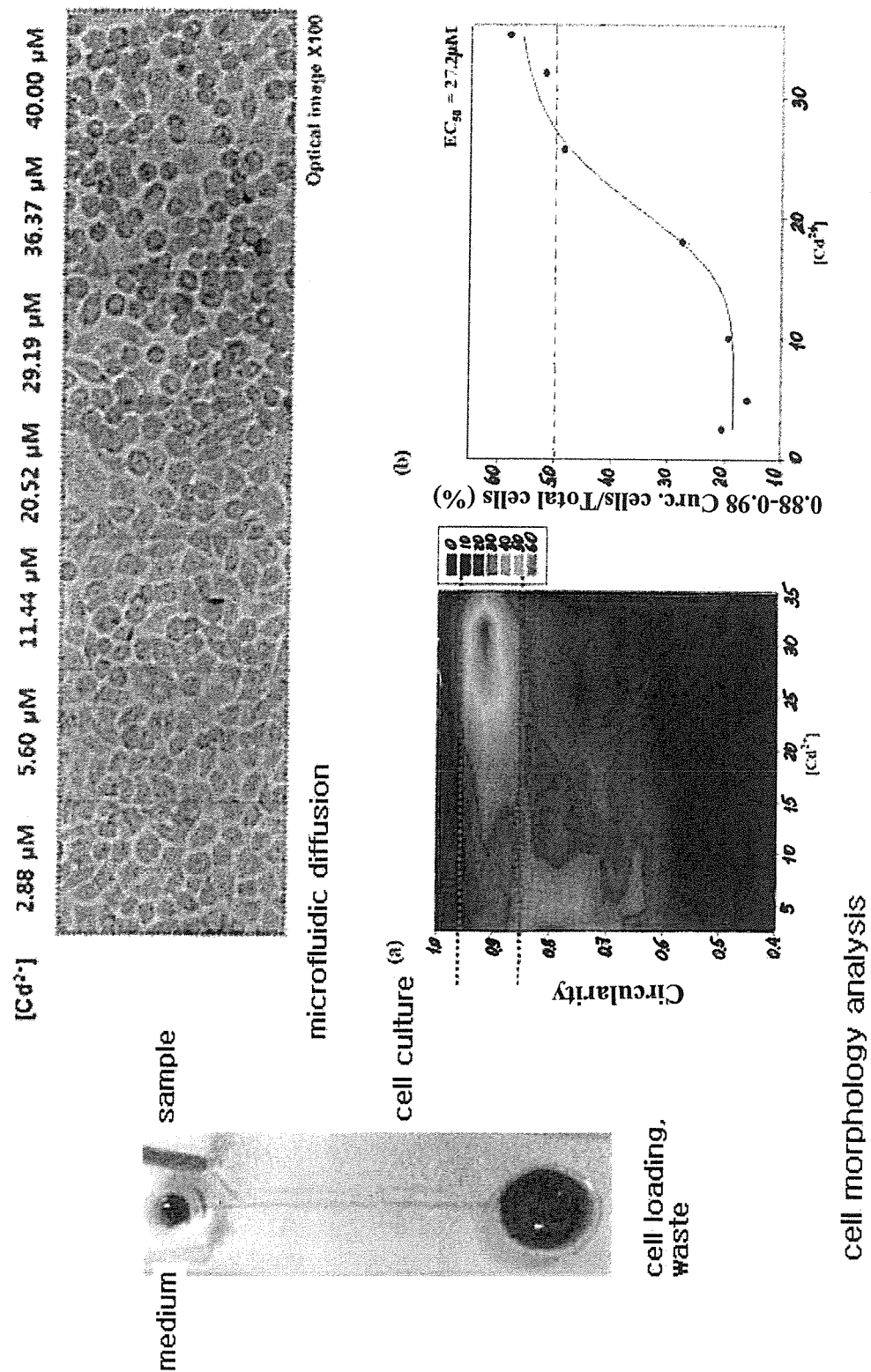
Figure 17:
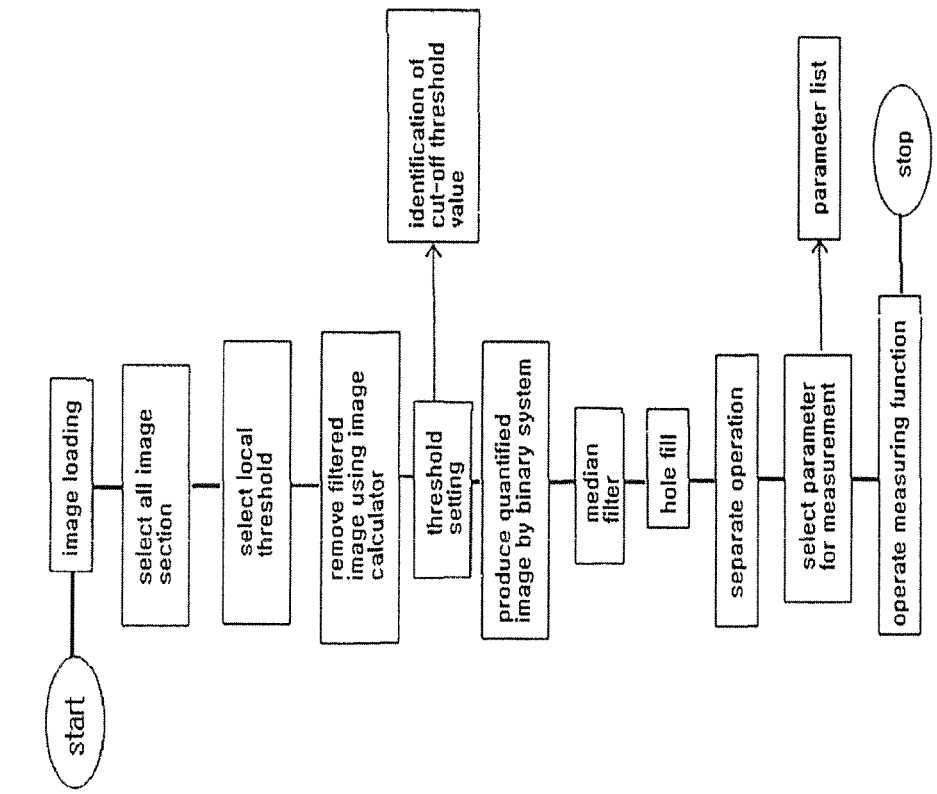
FIGS. 17 to 19: flow charts of processes performing the cell image analysis according to optical density (absorbance) image analysis and the results of one example thereof.
Figure 17:
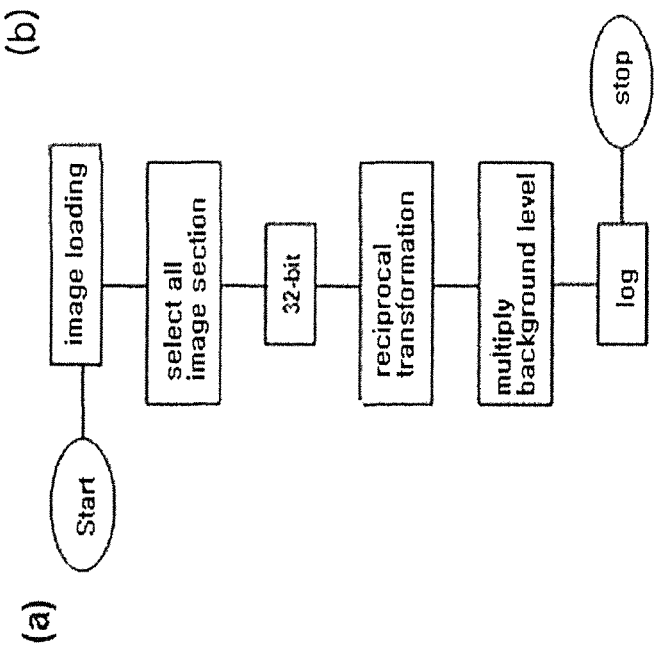
Figure 18:
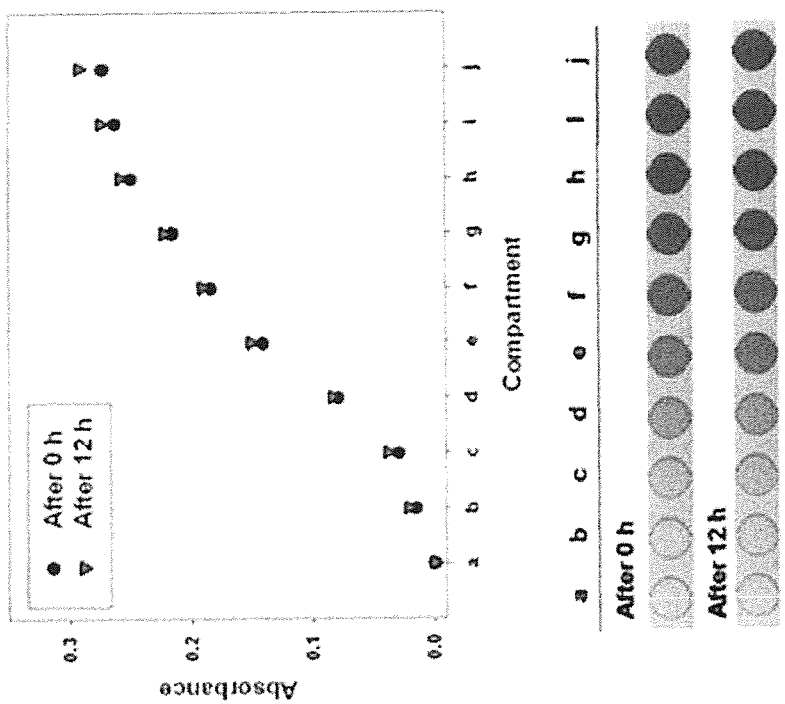
Figure 18:
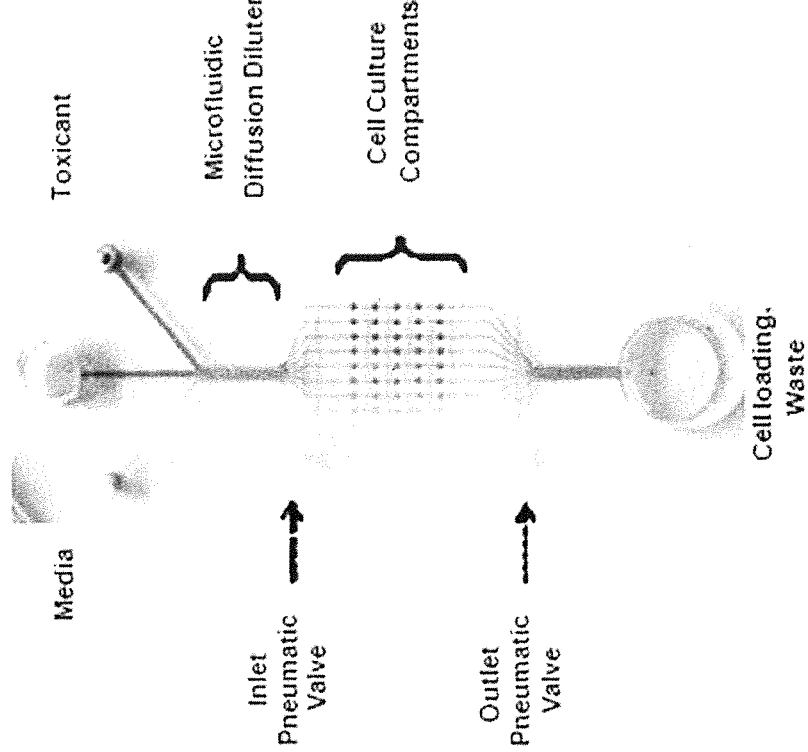
Figure 18:
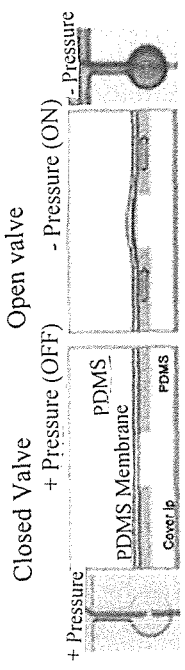
Figure 19A:
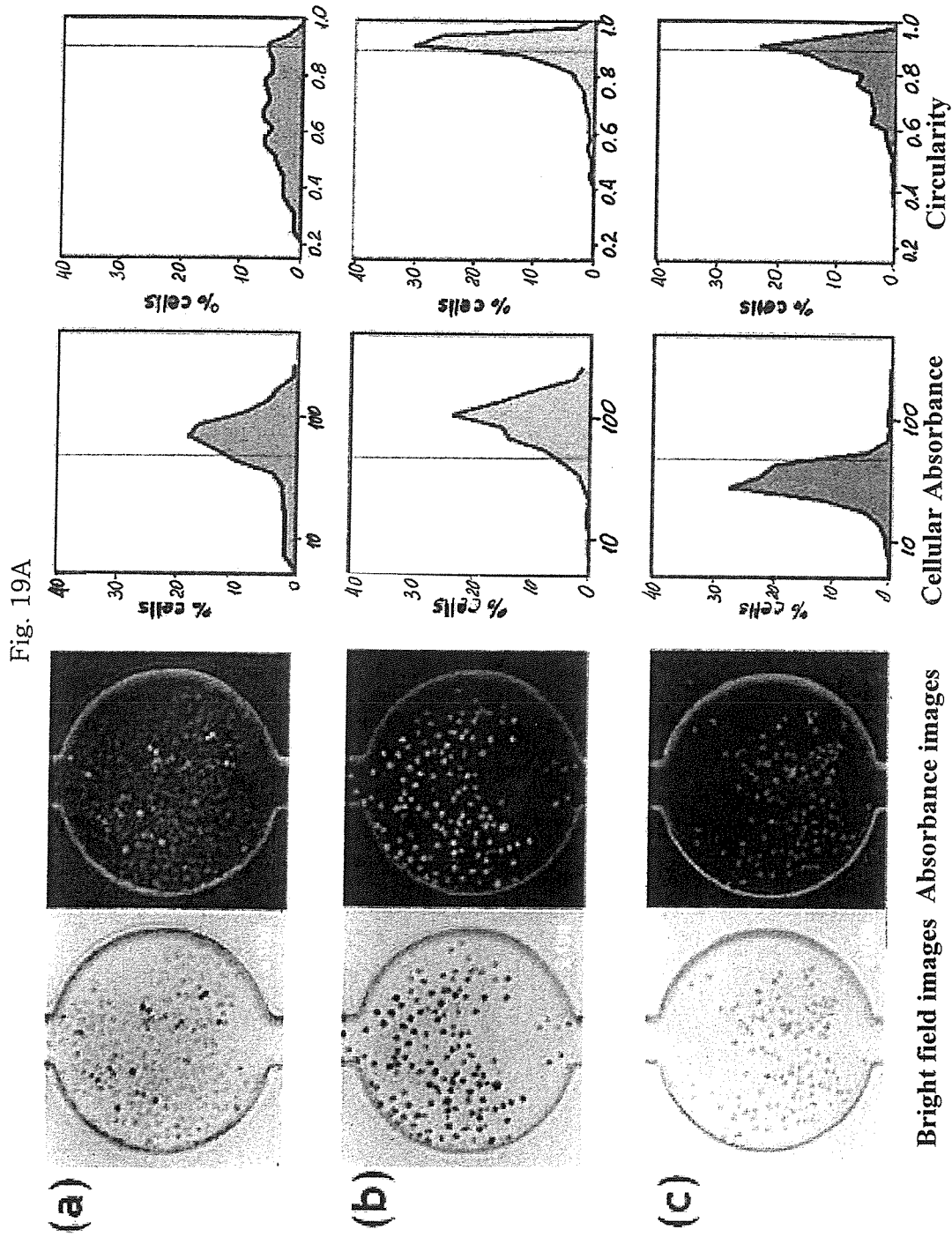
Figure 19B:
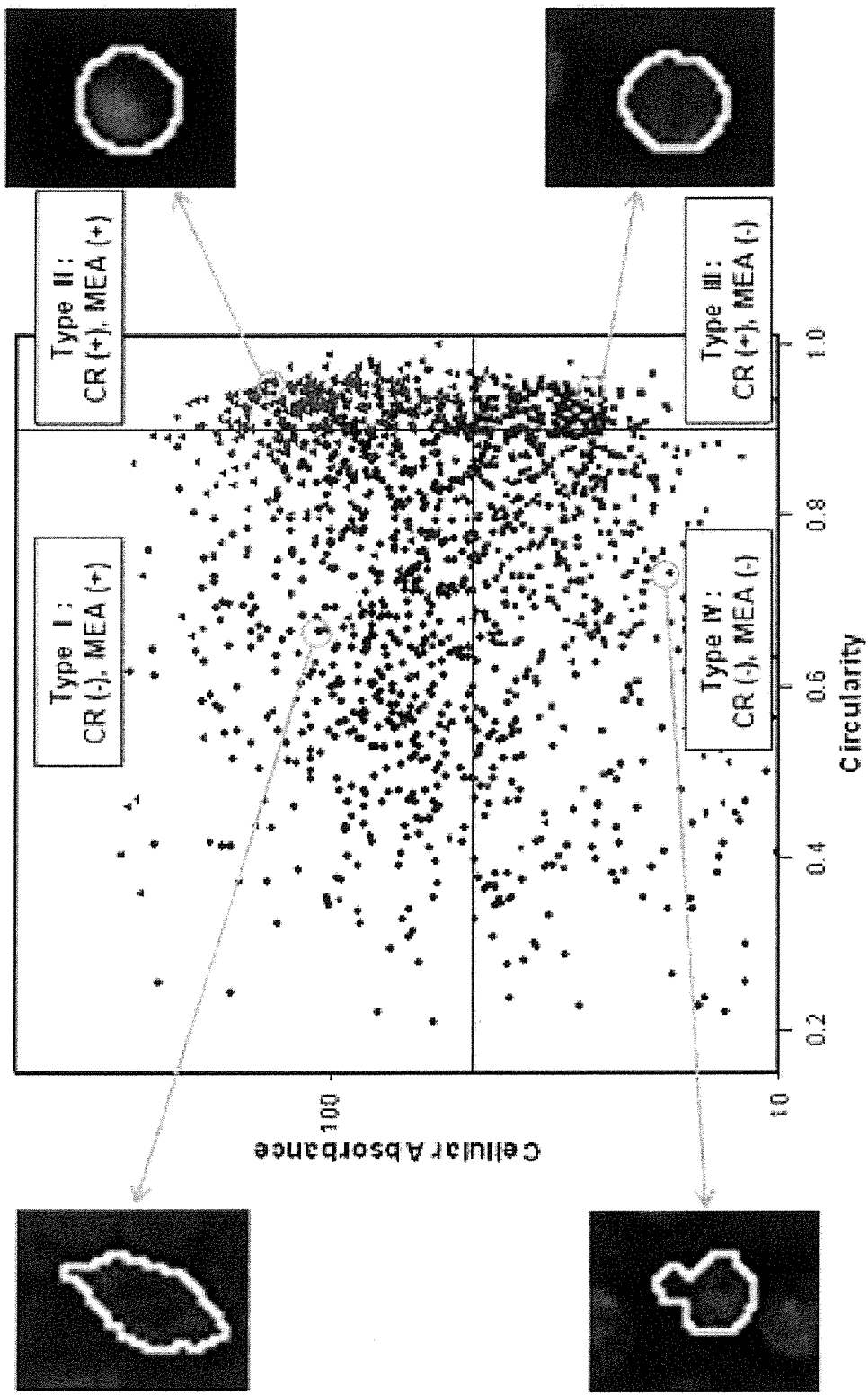

Flow charts of performance processes in the case of the cell morphology analysis are shown in FIGS. 14 to 16. And, the charts in the case of the absorption image analysis are shown in FIGS. 17 to 19.

The absorption image analysis is briefly described with one example, and it may comprise the following processes.

inducing an apoptosis reaction by exposing a cell layer to the nano-materials;

inducing crystal formation or cell staining by injection absorption dyes;

taking pictures of the cell layer, and extracting at least one apoptosis factor selected from a group consisting of the absorption factor per cell, cell number and the morphology factor value from the shot images; and quantifying the apoptosis mechanism and the degree of apoptosis by analyzing the parameters of the extracted apoptosis factors.

As previously described, MTT (3-(4,5-dimethyl thiazol-2-yl)-2,5-diphenyltetrazolium bromide)), MTS (5-(3-carboxymeth-oxyphenyl)-2H-tetra-zolium inner salt), WST (4-[3-(4-Iodophenyl)-2(4-nitrophenyl)-2H-5-tetrazolio]1,3-benzene disulfonate) and trypan blue can be used for fluorescence analysis. When MTT is used, the wavelength selectively passing through to obtain images at the maximum absorption region may be in a range of 550 nm±60 nm; when MTS formazan is used as a fluorescent dye, the wavelength selectively passing through to obtain images at the maximum absorption region may be in a range of 490 nm±60 nm; and when trypan blue is used as a fluorescent dye, the wavelength selectively passing through to obtain images at the maximum absorption region may be in a range of 590 nm±80 nm. Particularly, when MTT is used as a florescent dye, it is preferred to give the optimum time of 10-240 min to induce the formation of formazan crystal by the oxidation-reduction reaction.

In this case, the shooting of the cell layer can be performed using a cell image analysis device which comprises: a light source in the visible light region to obtain optical images selected from a group consisting of a tungsten lamp, LED light source and laser light source; a CCD (charge coupled device) camera detecting cell images collected from an objective lens; a cell culture platform to place a cell culture system containing a mono cell layer; a device for passing through the wave at the light source to obtain images at the maximum absorption region applied to the used fluorescent dye; and an image processing program, which can extract at least one apoptosis factor selected from a group consisting of the fluorescence factor per cell, cell number and the morphology factor value by analyzing the images obtained from the CCD camera to quantify the apoptosis process.

The absorbance per cell in the shot images as an absorption factor per cell can be extracted by distinguishing the cells in the shot images at a microscope equipped with an image acquiring constituent, analyzing the shot images at the image analysis program to segmentate, and overlapping each analyzed and selected cell to an image which was transferred to absorbance after dividing the signal (I) in the original image with signal value ($I_0$) of the background region not containing the cells, followed by transforming it to log value.

And, the degree of apoptosis is quantified by analyzing the value of the morphology factor selected from a group consisting of the occupied area per cell and circularity; or as an absorption factor, at least one absorbance selected from a group consisting of mean absorbance per cell and integrated absorbance per cell, from the filmed images.

In this manner, in one embodiment, the present invention provides a method for the toxicity assessment of nano-materials comprising the steps of analyzing dose characteristics of the nano-materials using Selective Multi-Plane Illumination Microscopy (mSPIM), and analyzing cellular responsiveness to the nano-materials using image cytometry.

In another example, the present invention can assess the cellular responsiveness by quantifying apoptosis through analysis using a normal•inverted exposure apparatus.

The method can selectively assess the direct toxic effects of the nano-materials to in vitro cells by minimizing the influence of the heterogeneity of the nano-particles in a solution caused by agglomeration and sedimentation. Namely, this method is characterized by exposing the nano-materials to the cells using an "inverted exposure apparatus" together with the normal exposure apparatus.

Figure 20:
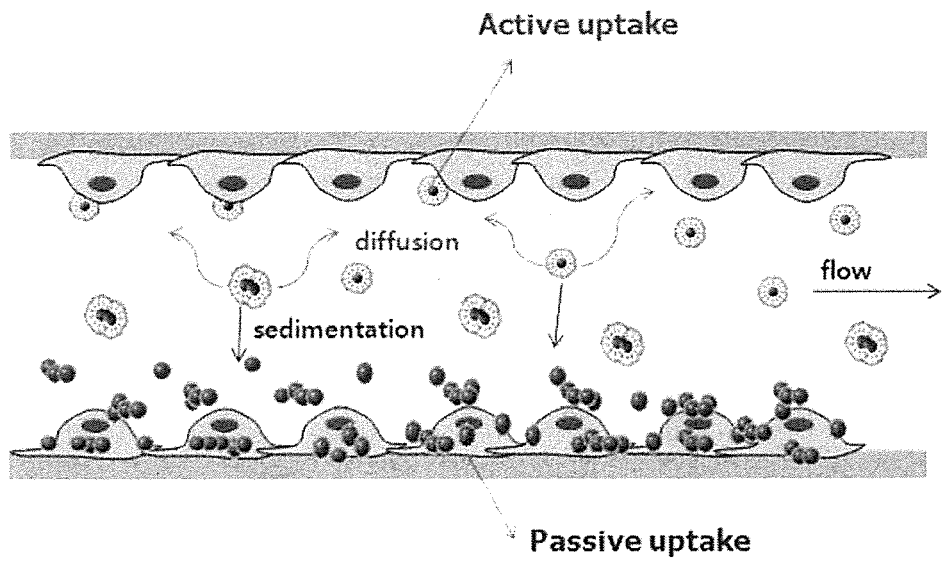
FIG. 20: a diagram representing various cell delivery processes which are expected when nano-particles are exposed in the blood vessel.

Because cells are really not only located on the bottom but are also evenly distributed in all up-and-down and left-and-right directions in organs in a living body, when the heterogeneous nano-particles are exposed in the living body, there are errors indicating that the toxicities of the cells located in the up, left and right planes are different from the toxicity of the cells located in the bottom plane. Therefore, incorrect toxicity results can be obtained if the toxicity assessment of the heterogeneous nano-particles, which can be agglomerated and sedimented, is performed using the conventional in vitro toxicity assessment method (FIG. 20).

In the present invention, a three-dimensional in vitro toxicity assessment method involving placing the cells at the top and bottom planes to expose the heterogeneous nano-particles can be used to solve the problem. When the toxicity assessment of the nano-particles is performed by placing the cells at the top and bottom planes, the practical toxicity of the nano-particles, wherein the toxicities or the toxicity mechanism of nano-particles to the cells of the top and bottom planes are compared according to the degree of heterogeneity of the nano-particles, or the toxicity according to the concentration gradient generated from the sedimentation of the nano-particles is removed, can be selectively assessed.

Namely, the use of the normal and inverted exposure apparatus corrects the concentration resulting from the heterogeneity of the nano-materials in a cell medium, and at this time, the concentration of the exposed nano-materials can be corrected using the known formulas (theoretical formula, empirical formula) reflecting the stability of the nano-materials in the cell medium [see: Justin G. Teeguarden et al., TOXICOLOGICAL SCIENCES 95(2), 300-312 (2007)].

Particularly, when using the normal and inverted exposure apparatus, image cytometry can be used together, more preferably, to solve the error problem caused by the optical or catalytic property of nano-particles when measuring cell activity.

When the nano-particles are exposed in the previously mentioned inverted nano-material exposure apparatus, the influence of the sedimented nano-particles can be removed, but the errors resulting from the optical or catalytic property of the nano-particles, which is generated by the extracellular nano-particles, cannot be removed. Therefore, image cytometry can be used to remove the errors caused by the catalytic property of the nano-particles. The image cytometry is the same as described above.

Namely, in the present invention, the degree of cell death progression caused by apoptosis and necrosis of the cells attached to the surface are analyzed by applying a modified MTT (tetrazolium-based colorimetric) assay and image processing method in a multiwell plate using an inverted nano-material exposure apparatus. The influence resulting from the heterogeneity of the nano-particles in an aqueous solution due to agglomeration and sedimentation is minimized using a normal and inverted exposure apparatus, and the errors of the existing apoptosis analysis method caused by the optical or catalytic reactivity of the nano-particles are minimized by using image cytometry. And the results of the quantitative analysis of the apoptosis are combined, and then the cellular responsiveness to the nano-particles actually taken up by the cells is analyzed.

Therefore, in another example, the present invention provides a method for the toxicity assessment of nano-materials comprising the steps of: assessing the dose characteristics of the nano-materials themselves using Selective multi-Plane Illumination Microscopy (mSPIM); and assessing the cellular responsiveness to the nano-materials using a normal and inverted exposure apparatus.

In this manner, the present invention more accurately and objectively assesses the toxicity of nano-materials by sequentially analyzing the dose characteristics of the nano-materials and the cellular responsiveness to the nano-materials, and then combining (considering) the results.

[Platform and Device]

Another aspect of the present invention relates to a device and platform for the toxicity assessment of nano-materials, which can perform the method or provide the system for the toxicity assessment of the nano-materials.

Further, the present invention provides a nano-material toxicity assessment device and platform equipped with each analyzer to perform the analysis using mSPIM, image cytometry and analysis using a normal and inverted exposure apparatus sequentially through one device. The schematic diagrams thereof are illustrated in FIGS. 3 and 4.

Figure 3:
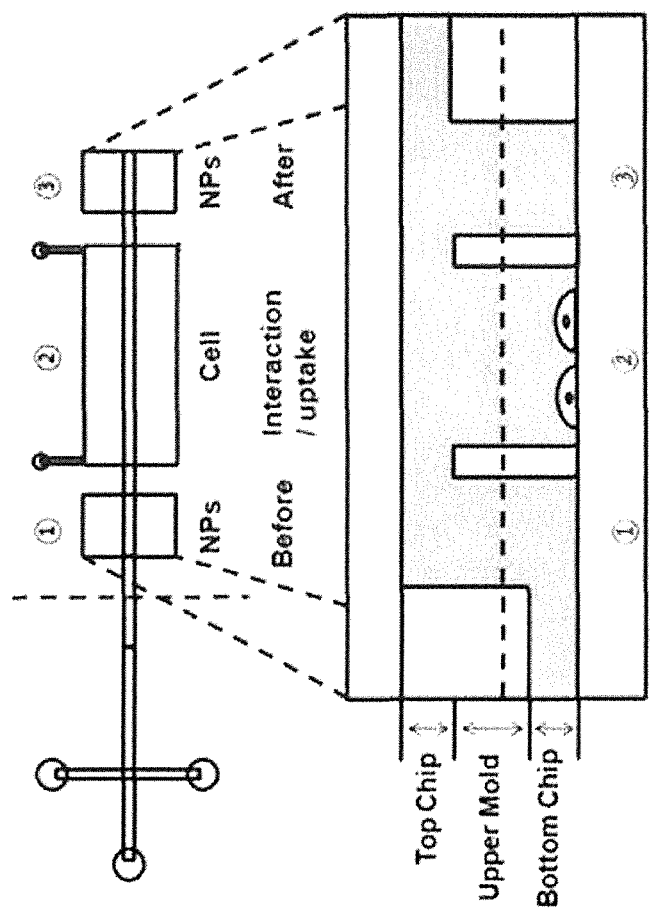
FIG. 3: a diagram of a nano-material toxicity assessment device equipped with an analyzer (chip) to perform the nano-material toxicity assessment sequentially through one device.

The characteristics and the cellular responsiveness of the nano-materials can be sequentially measured using the device equipped with mSPIM consisting of a laser light source, a cylindrical lens reducing the laser beam thickness and an objective lens, an objective lens placed perpendicular thereto and focusing fluorescent light, and a detector (FIGS. 3 and 4); which comprises a channel to analyze the characteristics of the nano-materials exposed in a cell culture solution (located in OD of FIG. 3), a channel to measure the cellular responsiveness to the nano-materials (located in ② of FIG. 3), and a channel to analyze the characteristics of the nano-materials after exposure to the cells (located in ③ of FIG. 3).

Descriptions for each apparatus and method are the same as described above.

Thus, the present invention can reduce the errors caused by the heterogeneity of nano-particles, and therefore can more accurately and reproducibly assess the dose-responsiveness relation of the nano-particles by directly measuring the quantitative and the size distribution of the nano-particles using mSPIM in real-time, and by monitoring the agglomeration coefficient of the nano-particles in a cell medium, the nano-particles' cellular uptake and the like.

Furthermore, the present invention can assess the nano-material toxicity more accurately and objectively by performing a method, which can selectively assess the degree of the nano-material uptake and the direct toxicity of the nano-materials by minimizing the influence resulting from the heterogeneity of the nano-particles in an aqueous solution due to agglomeration and sedimentation; and minimizing the errors of the existing apoptosis analysis method caused by the optical or catalytic reactivity of the nano-particles; and the like.

Therefore, the present invention is very useful to secure a safety guideline about the hazards which can affect nano-material production, environment and health by enabling the danger (toxicity) of nano-material exposure to be accurately figured out and understood.

EXAMPLE

Hereinafter, the present invention will be more particularly described by the preferred examples. However, these are intended to illustrate preferred embodiments of the present invention and do not limit the scope of the present invention. First of all, the effectiveness of (i) a method for assessing the dose characteristics of the nano-materials themselves using Selective multi-Plane Illumination Microscopy (mSPIM) and (ii) a method of analyzing the cellular responsiveness to the nano-materials using a staining method or a normal•inverted nano-material exposure apparatus were experimentally reviewed.

Example 1-1

Figure 5:
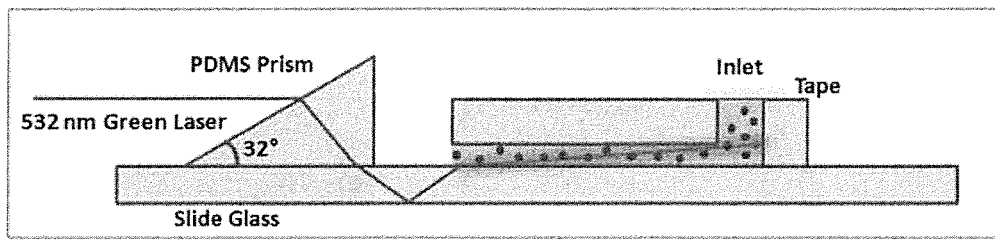
FIG. 5: a schematic diagram of a sample holder which can observe HILO or TIR forms possibly used in the present invention.
Figure 5:
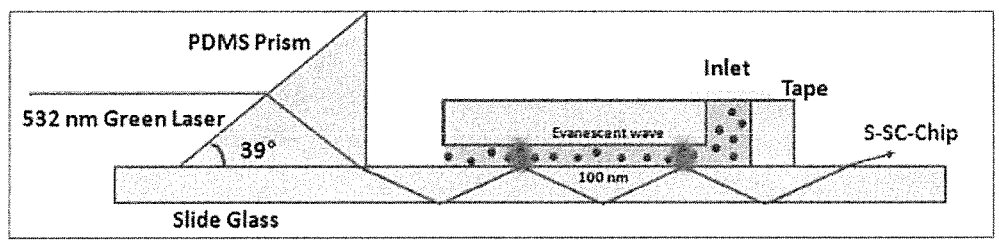

Analysis of Characteristics of Nano-Materials Using SPIM (1) Laser-Based Dark Field and Fluorescent Microscope Constitution The laser-based dark field and fluorescent microscope were formed as shown in FIGS. 4 and 5.

Lasers of various wavelengths were configured simultaneously to generate fluorescences of various wavelengths, and to reflect a short-wavelength laser and to pass a long-wavelength laser using a dichroic mirror. Therefore, lasers of various wavelengths could arrive at the sample at the same time.

In order to block the dispersed light, the thickness of the laser beam was primarily reduced using an iris and a slit. Secondarily, the beam shape was modified through a cylinder lens to the form of a thin plate, and tertiarily, the beam thickness was reduced to several micrometers through an objective lens. Because the scattering of the particles or fluorescence signals outside of the beam path can be excluded by reducing the beam thickness, images having high-resolution and high-contrast ratio can be obtained. Using this, particles of tens of nanometers, which are dispersed in a solution with a concentration ranging from several ppb to hundreds of ppb, can be observed. As shown in FIG. 5, a prism can be located in front of the sample holder so as to observe in HILO or TIR (total internal reflection) mode. In this case, an angle of the prism may decide HILO or TIR mode.

FIG. 5 is a schematic diagram of a sample holder which can observe HILO or TIR form. The laser light enters the sample horizontally and can realize HILO or TIR mode by passing through a prism, which is attached in front of a microfluidic chip by a van der Waals force, followed by being refracted. In the case of HILO, the laser is irradiated by being refracted at a several-degree angle from a horizontal plane. In the case of TIR, the sample within the height range of several hundred nm from the bottom side can be observed because an evanescent field is formed on the total reflection face.

(2) Production of Sample Holder

A PDMS structure was produced using a Teflon mold and used as a sample holder.

The size of the sample holder containing the nano-particle solution was 2 mm×5 mm×3 mm, and it had a smaller dose than the existing sample holder having several ml of volume such as a cuvet.

Further, in order to reduce the scattering at walls, the PDMS holder primarily produced with the Teflon structure was coated with a pre-polymer solution prepared by diluting PDMS in n-hexane to improve the surface, which had caused irregular reflection due to roughness of the PDMS surface, by making the surface smoother and more transparent.

The produced sample holder was combined with a channel of the existing microfluidic chip, and quantification and size analysis were performed of the nano-materials dispersed in the microfluidic chip.

The chip was produced as follows. A Teflon structure was mounted on the master mold of the microfluidic chip, and a pre-polymer, prepared by mixing a hardener and PDMS (1:10), was poured followed by hardening thereof at 60° C. in an oven, according to the existing method, to prepare the microfluidic chip.

(3) Real-Time Measurement of the Number of Nano-Particles Dispersed in Solution

In order to measure the number of the nano-particles in a solution where nano-particles of different sizes are dispersed, 15 nm gold particles (0.477 ppm) and 30 nm gold particles (0.546 Ppm) produced at BBI, and 50 nm $SiO_2$ (0.2 ppm) produced at Biterials were dispersed in a solution, respectively, and they were observed.

The diluted solution was poured into a sample holder having a height of 3 mm, and a laser having a wavelength of 473 nm was perpendicularly irradiated at the wall of the sample holder. At this time, the nano-particles scattered, were brightly shown on the laser beam path, and were saved as images using a 20× objective lens and CCD camera.

Figure 6:
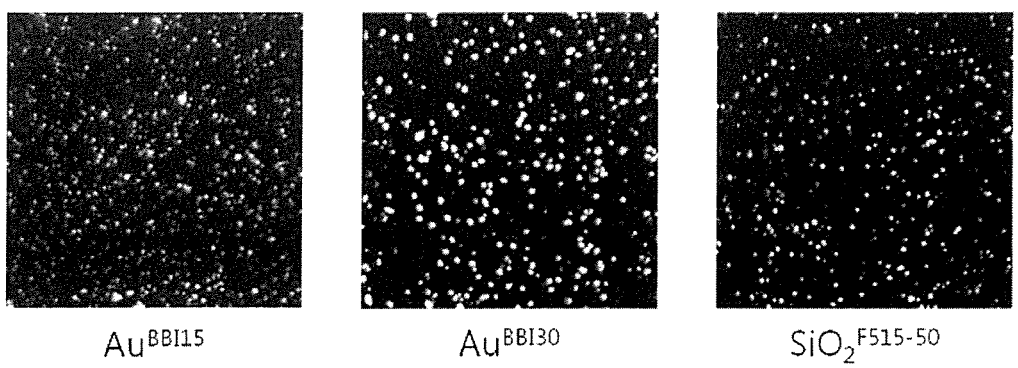
FIG. 6: results of observing gold nano-particles of 15 nm and 30 nm, and silica particles of 50 nm, which are dispersed in DI-water with PLS mode.
Figure 7A:
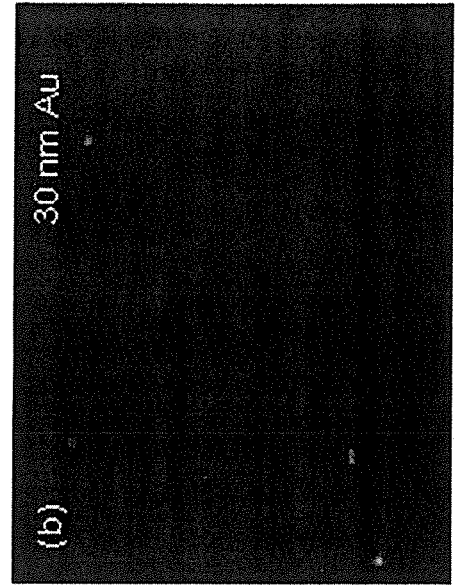
FIG. 7: results of observing the dispersed gold nano-particles of 15 nm and 30 nm with HILO mode, and measuring the size distribution of each particle by tracing the Brownian movement.
Figure 7A:
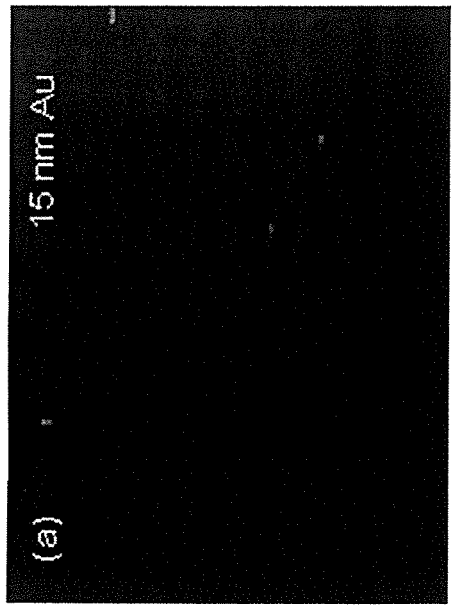
Figure 7B:
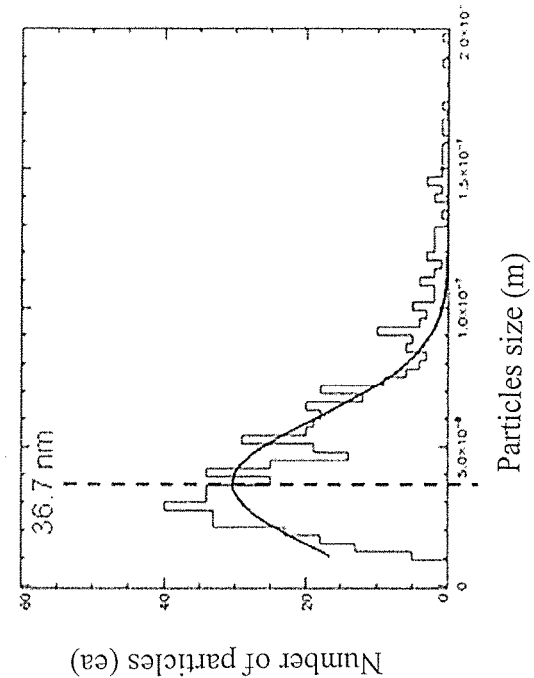
Figure 7B:
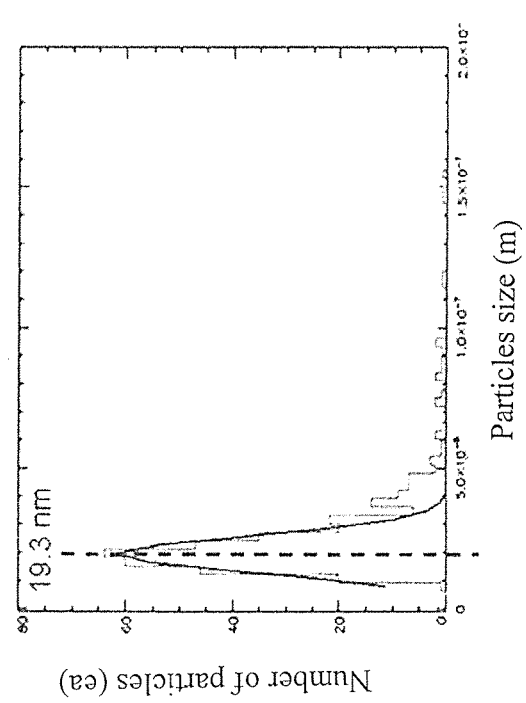

The saved images are the images shown in FIG. 6. FIG. 6 shows the results of observing gold nano-particles of 15 nm and 30 nm, and silica particles of 50 nm, which are dispersed in DI-water with PLS mode. Because the laser beam was thin, the scattered light was not generated at regions out of the focal plane, and the background is expressed darkly, while the nano-particles located on the path of the laser beam are expressed as bright points because they scattered light.

The particle number was measured by analyzing the saved images by image analysis using imageJ. In order to obtain statistically trustable data, one hundred images were saved, and the particle number was measured from the images through the macro function of imageJ. The variables to be entered in the threshold and the size categories of the macro function can be changed, and there may be an image adjustment process such as a maximum filter.

(4) Real-Time Measuring of the Number of Nano-Particles Dispersed in Solution

One hundred photos of the nano-particles dispersed in a solution were shot with about a 50 ms hour or less time interval, and the diffusion coefficient (D) of the Brownian movement nano-particles was measured from mean-square-displacements (MSD) of the brightly expressed nano-particles.

Namely, the nano-particle size was calculated using the stoke-einstein formula:

$$D=kT/(6\pi\eta r).$$

In the stoke-einstein formula, k is the Boltzmann constant, T is temperature, η is solution viscosity and r is particle radius.

In order to track the Brownian movement nano-particles, a solution containing the dispersed 15 nm and 30 nm gold nano-particles was observed with HILO mode.

Each gold nano solution was dropped into a glass having a thickness of 1 mm and covered with a cover slip. It was confirmed that when a prism, wherein an angle of the base plane was about 32°, was placed in front of the cover slip, the laser light entered a glass plane with refraction, and then totally reflected at a glass plane in contact with the air, followed by entry into the nano-particles solution layer with about 4.3° of a refraction angle. At this time, the median values of the observed size distribution of the nano-particles were 19.3 nm and 36.7 nm, respectively, as shown in FIG. 7.

Figure 8:
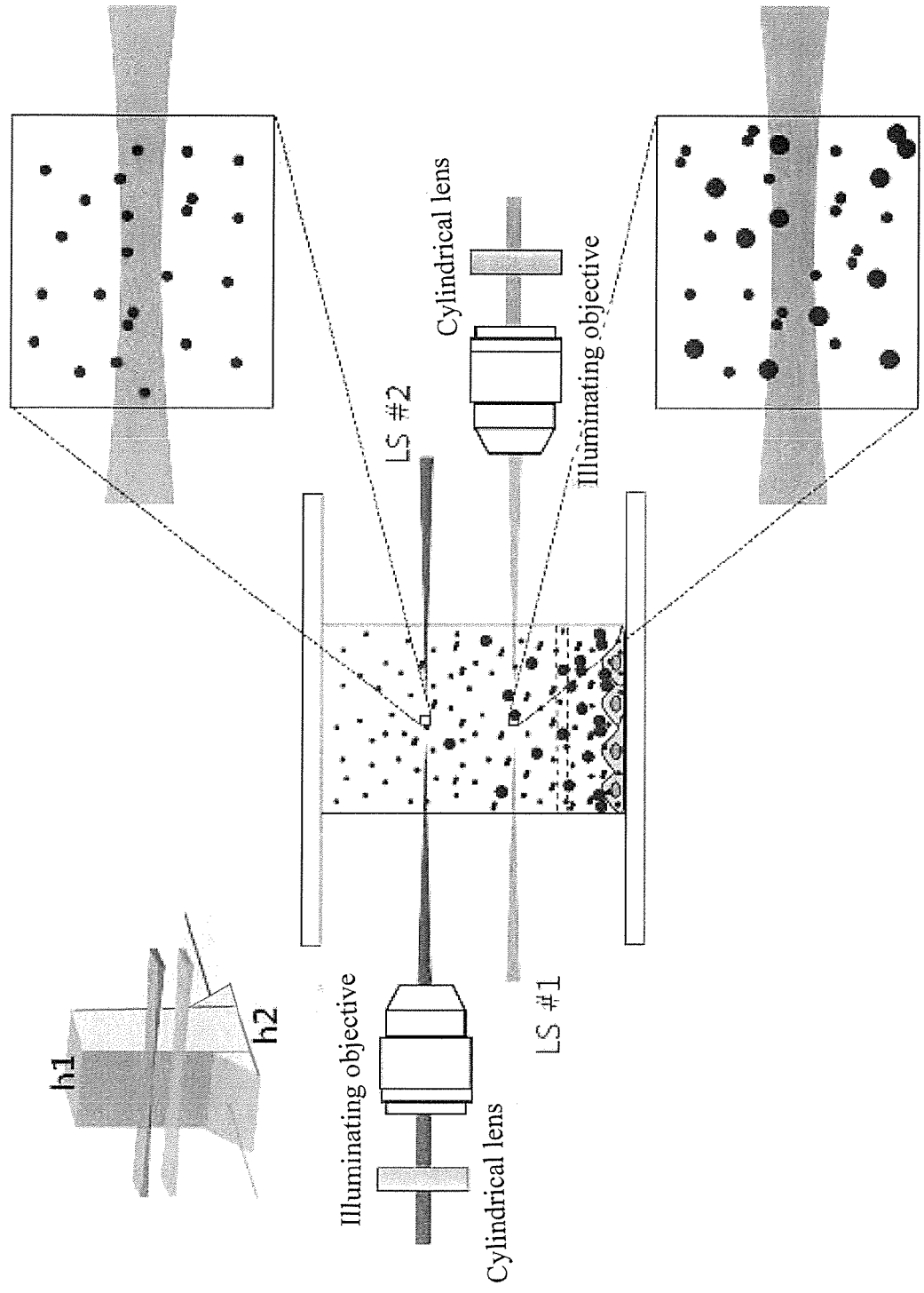
FIG. 8: a schematic diagram of a system, which can monitor the changes of the concentration and the size of the nano-particles which may occur during cell culture, in real-time.
Figure 9:
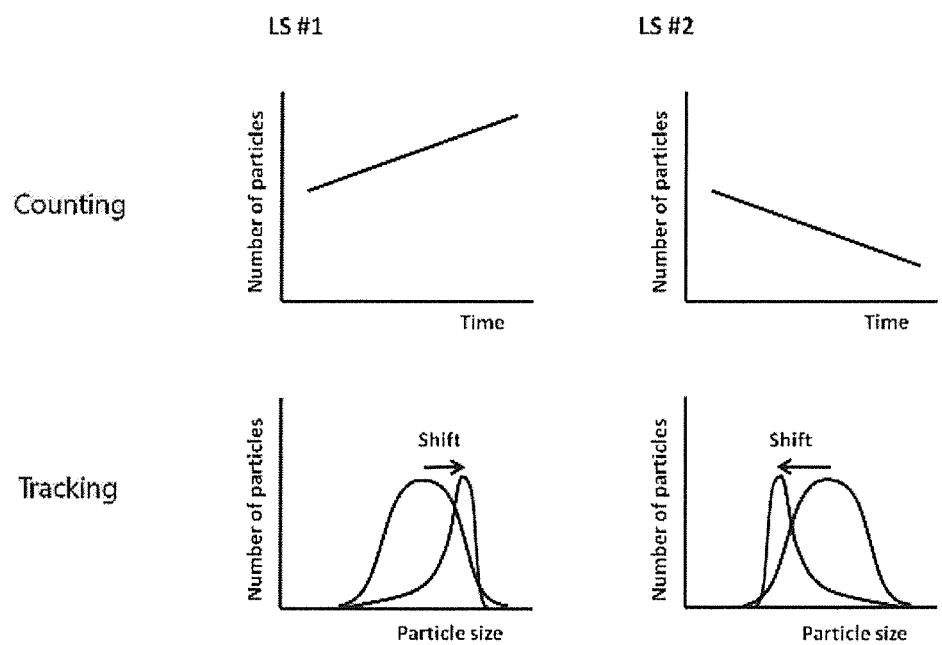
FIG. 9: graphs representing tendencies of sedimentation and agglomeration of nano-particles dispersed according to height in a time-dependent manner under the same conditions of FIG. 6.

(5) Measuring Agglomeration and Sedimentation Rate Coefficients of Nano-Particles In order to measure the agglomeration and sedimentation rate coefficients of the nano-particles exposed to the cell medium, a microfluidic chip, as shown in FIG. 8, was made.

FIG. 8 is a schematic diagram of a system, which can monitor in real-time the changes of the concentration and the size of the nano-particles which may occur during cell culture. The changes in the concentration and the size caused by the diffusion, agglomeration and sedimentation of the nano-particles were measured by simultaneously irradiating the laser beams of PLS forms having different heights within the different heights of the cell culture chamber serving as a sample holder.

The cell culture solution was poured into the prepared microfluidic cell chip and stored in a 37° C. incubator for 6 hours to make a condition where the cells can be cultured. Then, the concentration of cells remaining after serial culture were seeded to the cell culture channel in the microfluidic cell chip, and cultured in the 37° C. incubator for 48 hours or more. After the cell culture, the nano-particles were diluted with a PBS buffer to a lower concentration ranging from several ppm to several ppb, followed by being seeded to the microfluidic cell chip.

The prepared microfluidic cell chip was placed in a dark field and fluorescent microscope based on "SPIM", constituted as shown in FIG. 4, and the number change due to agglomeration and sedimentation of the nano-particles dispersed in the cell culture solution in real-time using the laser light source of PLS form was measured.

One hundred continuous photos of the dispersed nano-particles were obtained with about a 50 ms hour or less time interval. After 30 min, another one hundred continuous photos were obtained with about 50 ms hour of time interval. Like this, one hundreds of continuous photos were obtained with about 50 ms hour of time interval every 30 min for a total of 10 hours. When the changes in the nano-particle number and the size over time were measured from the obtained images, and the change rate in the number and the size were measured due to agglomeration and sedimentation of the nano-particles, the results shown in FIG. 7 were expected.

Namely, when the lower part of the dispersed nano-particles was observed (LS#1), the nano-particles were enlarged and sedimented, and the particle number increased over time because the dispersed nano-particles were sedimentated and agglomerated over time. And when the upper part of the dispersed solution was observed (LS#2), the particles were agglomerated over time, the enlarged particles were sedimented, and therefore, the result showed the tendency that the particle number was gradually reduced and only small particles remained at the upper part because the enlarged particles were not observed.

In other words, the particle number as well as the particle size increased over time at the part having a lower observed height, but the particle number decreased by the agglomeration and sedimentation of the particles over time at the part having a higher observed height, and only the smaller sized particles remained.

(6) Measuring Cellular Uptake of Nano-Particles

The cells were cultured at the lower face of the sample holder, and the real cellular uptake of the nano-particles injected into the cells may be different from the amount of the nano-particles initially injected into the culture solution because the nano-particles were agglomerated or sedimented according to the conditions of the culture solution when the cells were exposed to the nano-particles scattered in the culture solution.

Therefore, a laser source in the form of HILO was introduced to measure the amount of nano-particles actually injected into the cells because the cellular uptaken nano-particles can be measured with the HILO form. The laser passed through a prism and obliquely irradiated the bottom, and at the same time, the nano-particles scattered in the middle of the sample to the PLS form can be observed.

Figure 10:
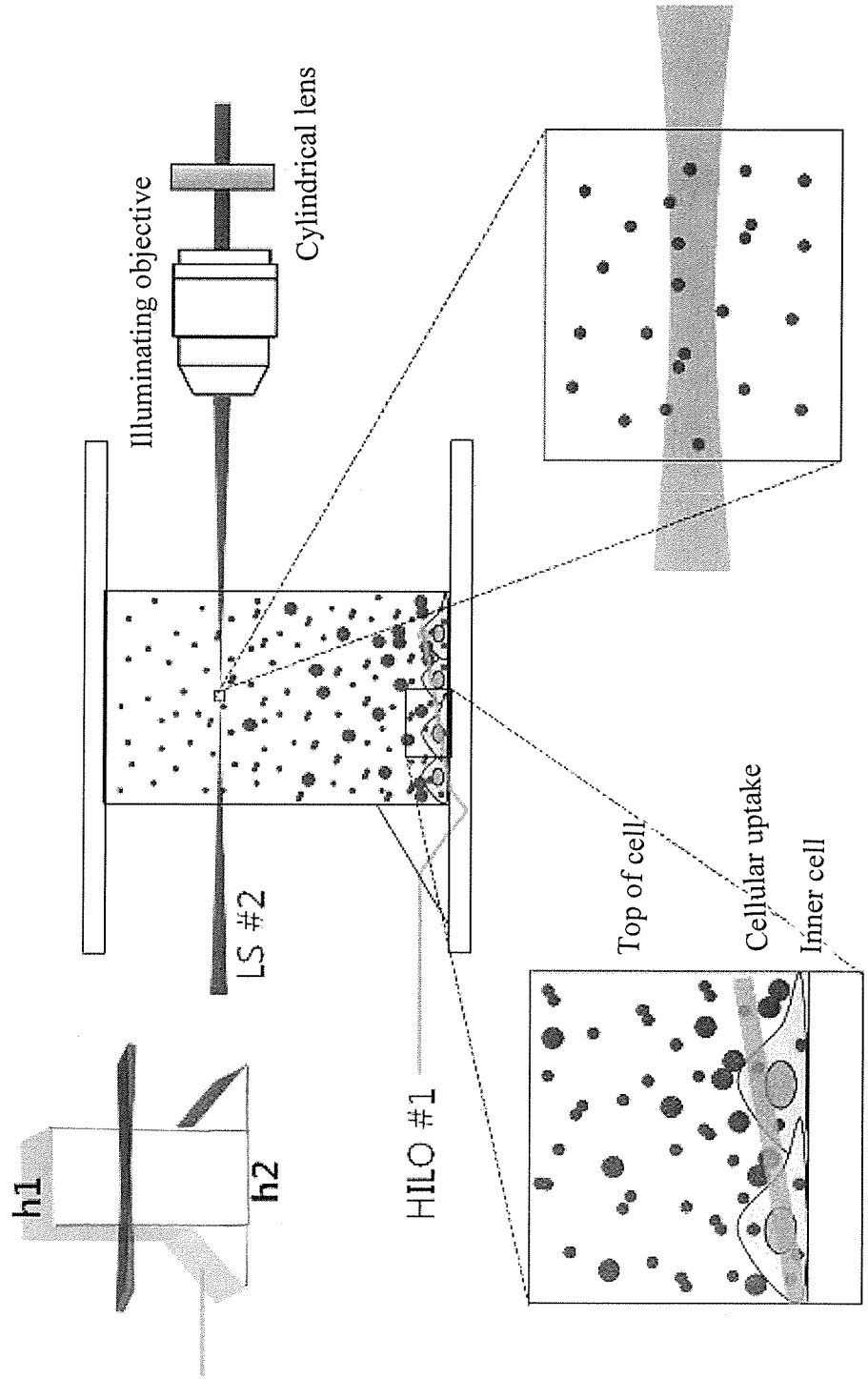
FIG. 10: a schematic diagram of the combined form of HILO mode to measure the cellular uptake dose of the nano-particles and PLS mode to measure the nano-particles dispersed in a solution at the same time.

FIG. 10 is a schematic diagram of the combined form of HILO mode to measure the cellular uptake dose of the nano-particles and PLS mode to measure the nano-particles dispersed in a solution at the same time. The nano-particles accumulated in the cells were directly observed with the light source of the HILO form which traverses the cells cultured on the bottom face of the sample holder (HILO#1) while the nano-particles, which changed over time, were monitored with the light source of the PLS form, which traverses the middle of the sample holder (LS#2).

Figure 11:
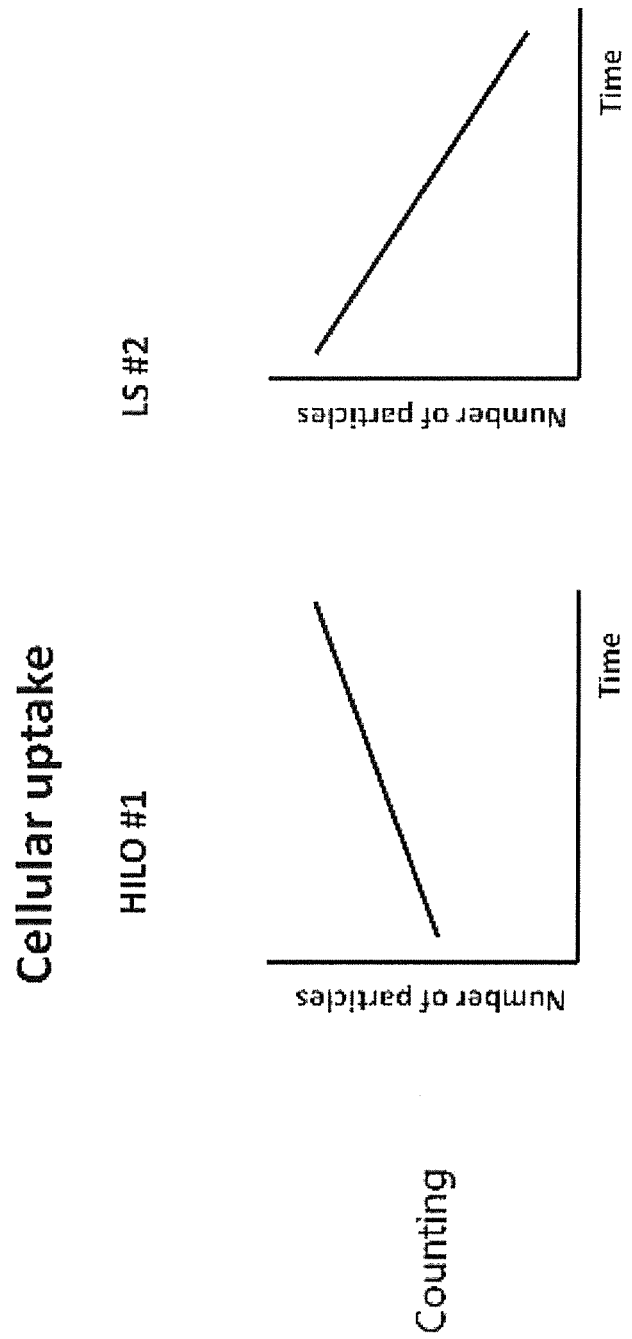
FIG. 11: results of monitoring the nano-particles under the same conditions of FIG. 10.

As a result, as shown in FIG. 11, the cellular uptake dose increased in a time-dependent manner (HILO#1) while the dose of the dispersed nano-particles at the upper part of the cell decreased in a time-dependent manner (LS#2).

Figure 12:
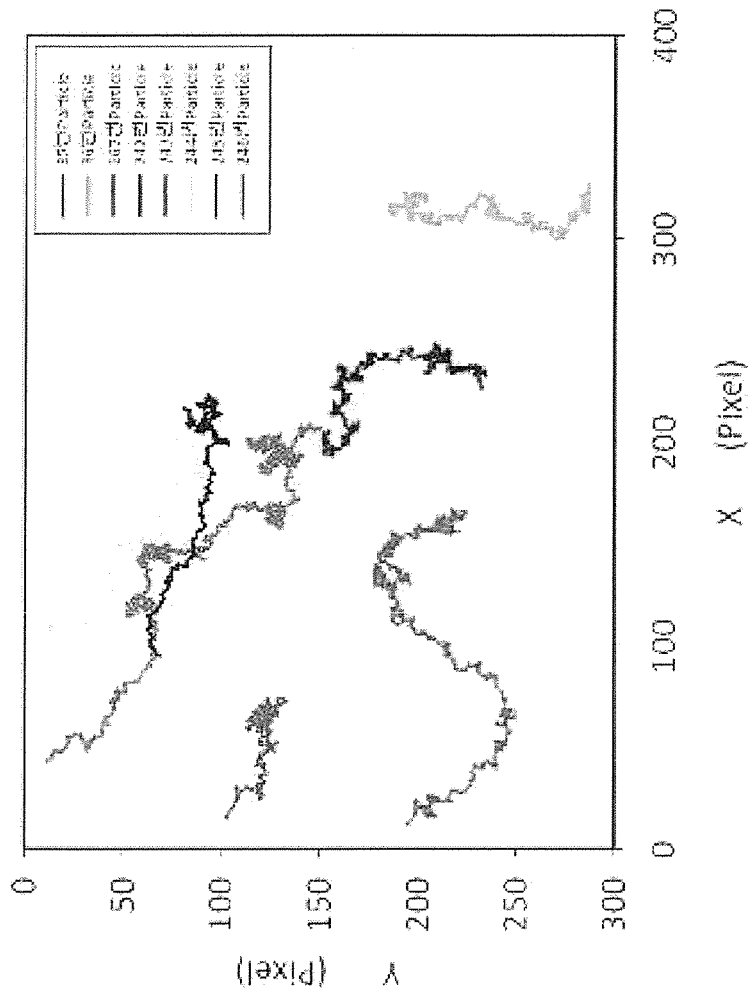
FIG. 12: results of observing the Brownian movement of nano-particles when the nano-particles are actually sedimented with an optical microscope in HILO mode.
Figure 12:
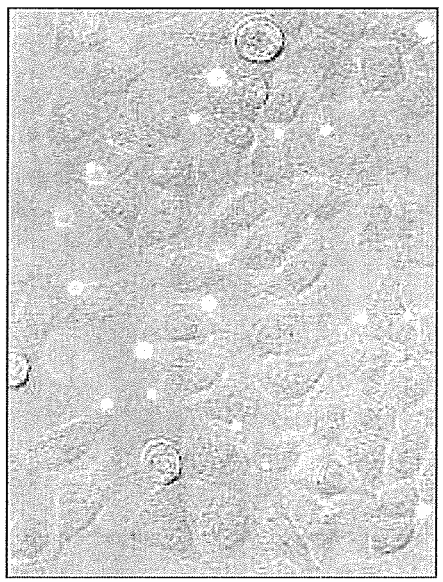
Figure 12:
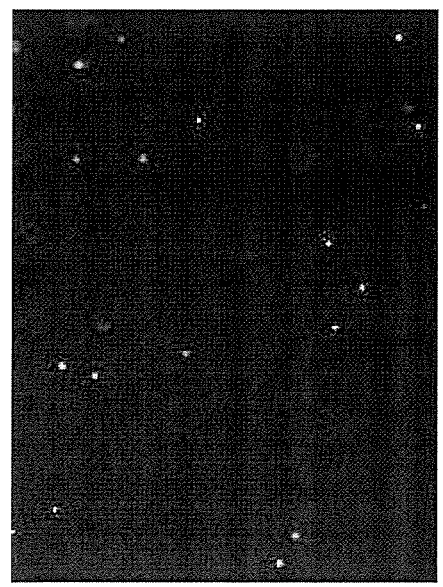

When the Brownian particles are tracked, a point when the movements are slowing down can determine whether the particles are accumulated in the cell, and therefore, the results of observing the cells and the nano-particles actually dispersed in the cell culture solution with HILO mode are shown in FIG. 12. The Brownian movements of the dispersed particles on the cell surface were observed before they accumulated in the cell.

Example 1-2

Cellular Responsiveness Analysis to Nano-Materials

The effectiveness of the method analyzing the cellular responsiveness of the nano-materials was experimentally checked as follows.

(1) Measuring Cellular Responsiveness Using Image Cytometry

The cells exposed to the nano-particles were stained using a fluorescent dye related to apoptosis, their images were filmed, and then the apoptosis was quantitatively analyzed by image cytometry.

MTT (3-(4,5-dimethyl thiazol-2-yl)-2,5-diphenyl tetrazolium bromide)) was used as the dye for the fluorescent staining. Image cytometry was performed for the obtained bright field images using image analysis program software (ImageJ).

The degree of apoptosis progress was quantitatively analyzed by quantifying the cell number, cell morphology, absorbance per cell and the like using information about the absorption factor and circularity from the above analyzed results.

The image analysis system used for the above analysis used a technique using an optical microscope equipped with a tungsten lamp as a light source and a charge coupling device (CCD) as a basic technique in order to obtain optical images (bright field images), and a microfluidic chip was mounted on an xy-z stage, followed by taking images about the apoptosis progress of the cells cultured in the microfluidic chip from a computer connected to the CCD camera, and then the microfluidic chip was arranged to culture the cells under continuous flow conditions using the flow from a syringe pump connected to the medium and a sample reservoir or gravity.

The cell culture environment, similar to the cell culture incubator, could be prepared on the microscope by maintaining the condition of 5% $CO_2$ and 37° C. in the microfluidic chip of the microscope, and real-time cell image shooting was made possible. The images saved on the computer were analyzed using image processing software. Through the analysis, a result that the cells exposed to the toxic material of relatively lower concentration had a low circularity value, but the cells exposed to the toxic material of the relatively higher concentration had a high morphology factor (circularity), was obtained. It was confirmed that the mean value of the morphology factor of the cells, which grow by being attached to the culture dish, was present between 0.5 and 0.7, and the value of the morphology factor of the cells that changed shape going through apoptosis was 0.8 or more.

The absorbance per cell as the absorption factor per cell can be extracted from the shot images by distinguishing the cells in the shot images at a microscope equipped with an image acquiring constituent, analyzing the shot images with the image analysis program to segmentate, and overlapping each analyzed and selected cell to an image which was transferred to absorbance after dividing the signal (I) in the original image with signal value ($I_0$) of the background region not containing the cells, followed by transforming it to log value:

$$A = \log(I_0/I)$$

In the above step, the degree of apoptosis can be quantified by analyzing the value of the morphology factor selected from a group consisting of occupied area per cell and circularity; or at least one absorbance per cell as a fluorescence factor selected from a group consisting of mean absorbance per cell and integrated absorbance (A: absorbance per cell, I: intensity of light expressed in a region containing cells at shot optical images, $I_0$: intensity of light expressed in a background region not containing cells at shot optical images), wherein $$\text{circularity} = 4\pi \times (\text{cell area}/\text{cell perimeter}^2);$$

mean absorbance per cell=mean of absorbances of each fixel in a cell region;

integrated absorbance per cell=mean absorbance per cell× number of fixel occupied by a cell.

In the step of quantifying the degree of apoptosis, parameters comprising the absorbance per cell obtained from image analysis were independently subjected to univariate analysis to obtain a dose-responsiveness curve, and the degree of apoptosis progression was quantified. And error in a conventional apoptosis analysis method caused by the scattering of the nano-particles themselves, i.e., optical or catalytic reactivity of the nano-particles, was reduced by using image cytometry.

Herein, the relation of the cellular responsiveness to the actual cellular uptake of the nano-particles was analyzed by linking the actually accumulated amount of the nano-particles in the cell measured in HILO form with the degree of apoptosis measured by image analysis, and the results are illustrated in FIG. 12.

(2) Using a Normal and Inverted Nano-Material Exposure Apparatus

Figure 22:
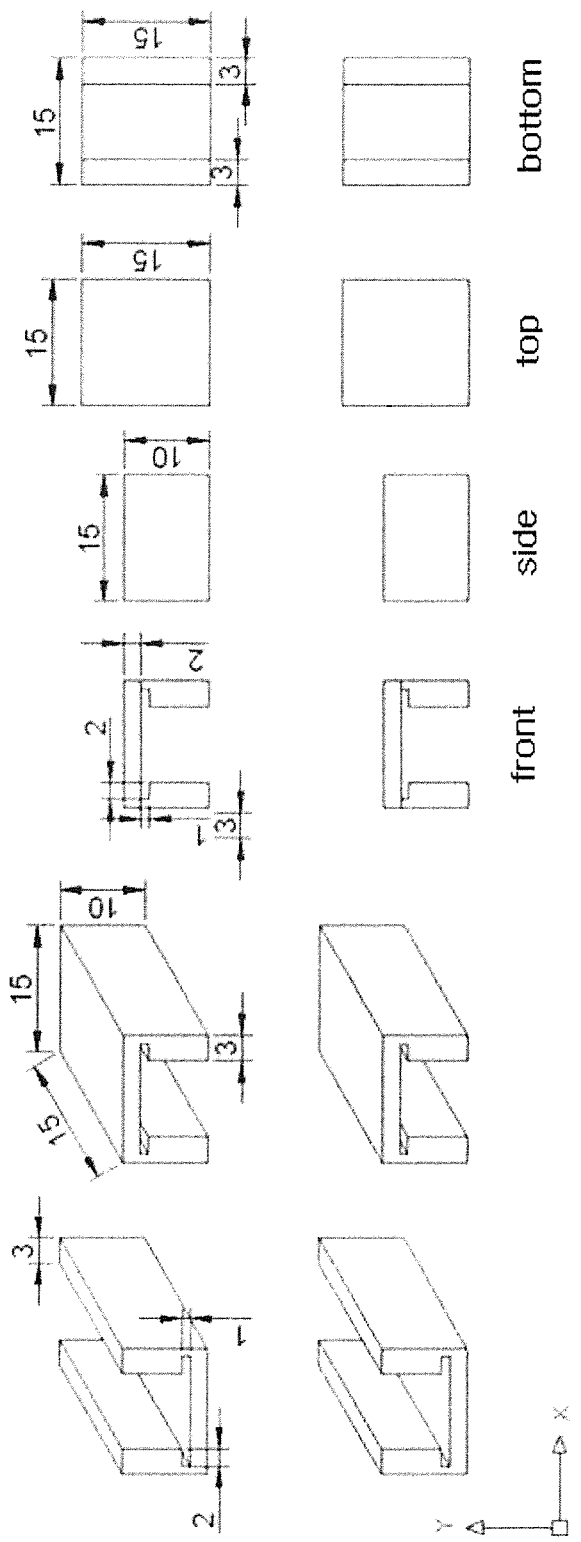
FIG. 22: drawings of a nano-material exposure apparatus.

1) Preparation of Normal and Inverted Nano-Material Exposure Apparatus, and Cell Culture Like the drawings shown in FIG. 22, a normal and inverted exposure apparatus was prepared using transparent polycarbonate and acrylic bonds. Two rectangles measuring 1.5 cm×0.8 cm×0.3 cm were attached to a square top measuring 1.5 cm×1.5 cm×0.2 cm to prepare a desk-shaped structure with legs. A polystyrene plate measuring 1.5 cm×1.5 cm was used as a cell culture substrate. The nano-material exposure apparatus and the cell culture substrate were washed with soapy water, and then submerged in 70% ethanol and sonicated for 30 min to wash.

On the other hand, the plasma-treated square polystyrene plate measuring 1.5 cm×1.5 cm was located in a 12-multiwell plate, and the nano-material exposure apparatus was mounted on the edge of the polystyrene plate followed by fixing.

The cultured cancer cell line (Hela cell line, Korea Biological Resource Center, Korea) was extracted as a suspension from the bottom of the cell culture dish to the concentration of $10^4 \sim 10^5$ cells/mL, and then seeded to the multiwell plate. The seeded cells formed an attached monolayer cell colony on the surface of the polystyrene plate. At this time, Dulcecoo's modified Eagle's medium (DMEM, Gibco, Grand Island, N.Y., USA, with 10% fetal bovine serum (Gibco, Grand Island, N.Y., USA)), 1% Penicillin-Streptomycin (Gibco, Grand Island, N.Y., USA))) was used and incubated for about 24 hours.

2) Treatment of Nano-Materials Using a Normal and Inverted Exposure Apparatus

A cell culture substrate, wherein animal cells were attached, was installed to the normal and inverted nano-material exposure apparatus facing up and down, respectively, and fixed. For normal nano-material exposure, the medium was removed in the state that the cells were cultured, and for inverted nano-material exposure, the nano-material exposure apparatus was installed to make legs thereof face up and to make the top touch the bottom side followed by installing the cell culture substrate to the cell attached side face down. And, the nano-material exposure apparatus wherein the cell layer was fixed thereto was installed in a multiwell plate, and the nano-materials were exposed. Namely, the cell culture solution comprising the nano-materials ($TiO_2$) was exposed, and at this time, the solution was added to the volume (3 ml) to submerge the cell culture substrate in the inverted nano-material exposure apparatus.

Figure 23:
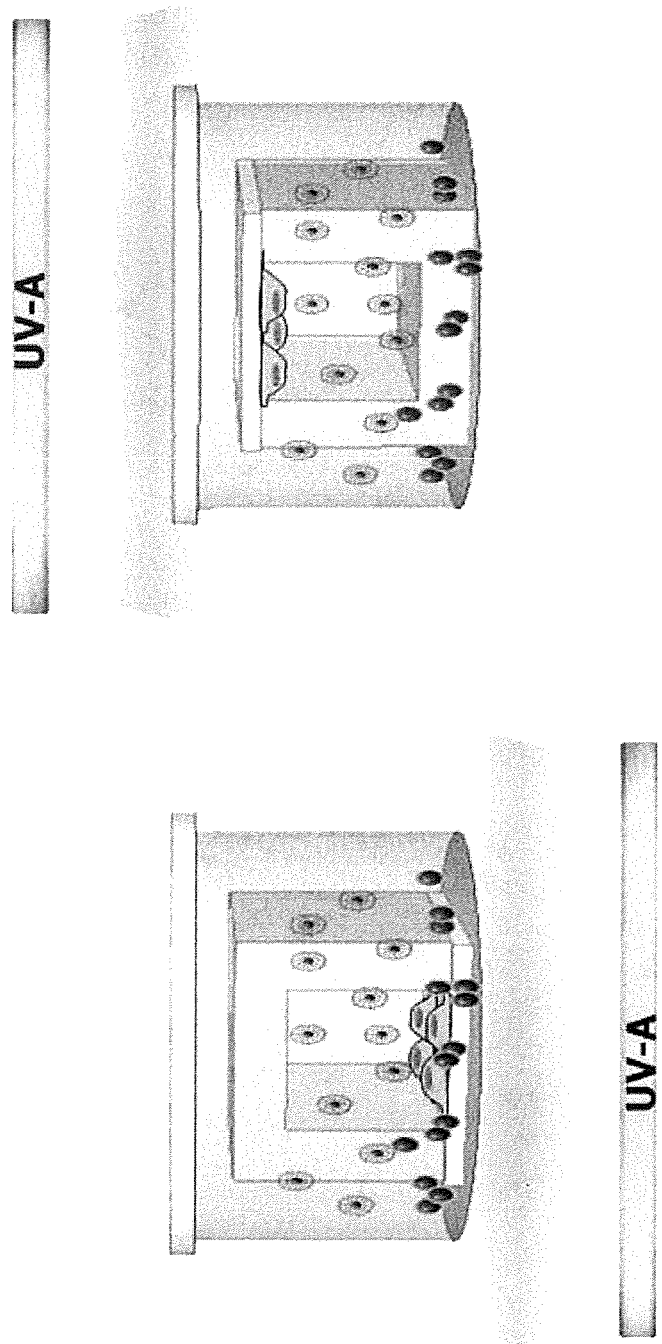
FIG. 23: diagrams of exposing nano-materials to a normal and inverted nano-material exposure apparatus followed by radiating UV-A.

The normal exposure was conducted by irradiating UV-A to the nano-materials from the bottom side of the multi well plate for 1 hour and 20 min, and the inverted exposure was conducted by irradiating UV-A to the nano-materials from the top side of the multi well plate for 1 hour and 20 min (FIG. 23). Then, the UV-A irradiated plates were put into an incubator (temperature: 37° C., and $CO_2$ concentration: 5%), and the nano-particles ($TiO_2$) were exposed for a total of 20 hours, including the UV-A irradiation time.

3) Analysis of Degree of Apoptosis

Figure 21:
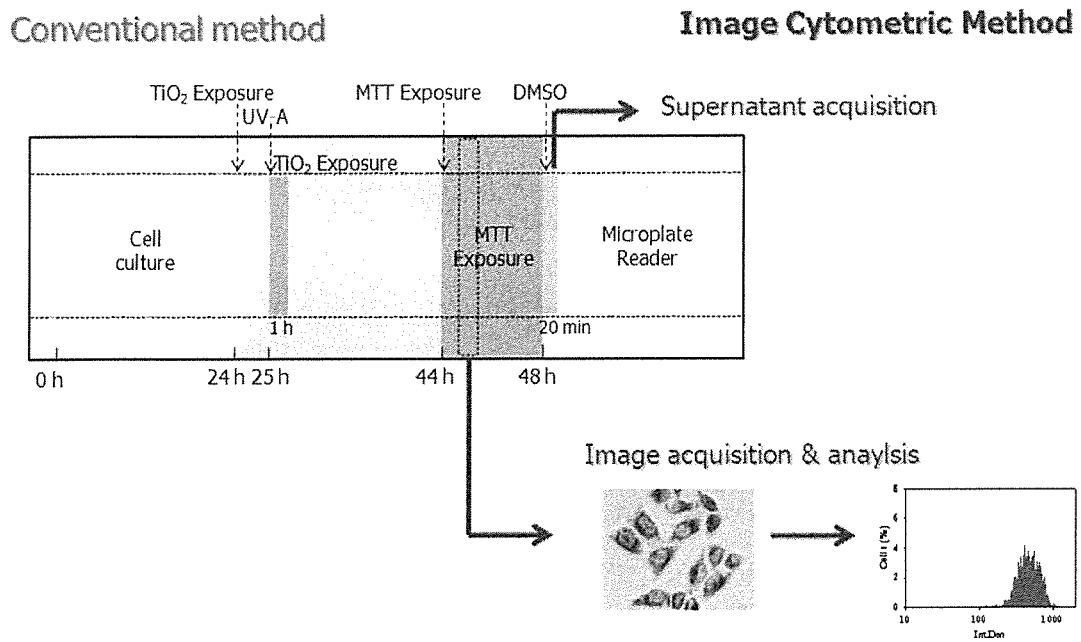
FIG. 21: an image comparing a conventional method and a method using an inverted exposure apparatus according to the present invention.

The modified MTT assay according to the present invention and a conventional MTT assay as a control were performed. The processes of a conventional method and a modified method according to the present invention are shown in FIG. 21, respectively.

To perform the conventional MTT assay, cells were cultured in a 96 well plate to the proper concentration followed by adding a toxic material, and then 100 μL of non-aqueous yellow MTT solution diluted 10-fold with the medium was added to each well. The plate was incubated in an incubator (temperature: 37° C., $CO_2$ concentration: 5%) to form formazan crystal. After about 4 hours, the extra medium was removed, and 200 μL of DMSO was added to each well to dissolve the non-aqueous formazan formed in the cell, followed by analyzing the absorbance at 595 nm using a microplate reader.

And, an MTT assay was performed according to the image cytometry suggested in the present invention (Example 1-2)). The nano-materials were treated with the cells, which were properly cultured in a multi well plate, for 20 hours, and then the nano-materials were removed, followed by exposing 1.5 ml MTT solution diluted 10-folds with the medium. The absorbance value by the MTT formazan crystal should be within a range having an effective fixel value at a bright field image. Therefore, in order to optimize the crystal formation time, a total of 30 min of formazan crystal formation time was given. After the crystals were formed, a process of dissolving the formazan crystals with an organic solvent (e.g., DMSO) was not needed, unlike the existing MTT assay, and bright field images were obtained using a microscope for image acquisition and treatment with the formazan formed in the cell. Because the MTT formazan has a maximum absorbance peak at about 550 nm, a bandpass filter having a maximum permeability at 530 nm and a bandwidth of 45 nm was used to obtain a short wavelength light source when optical images were obtained.

Cell viability was measured according to the method described above.

Figure 24A:
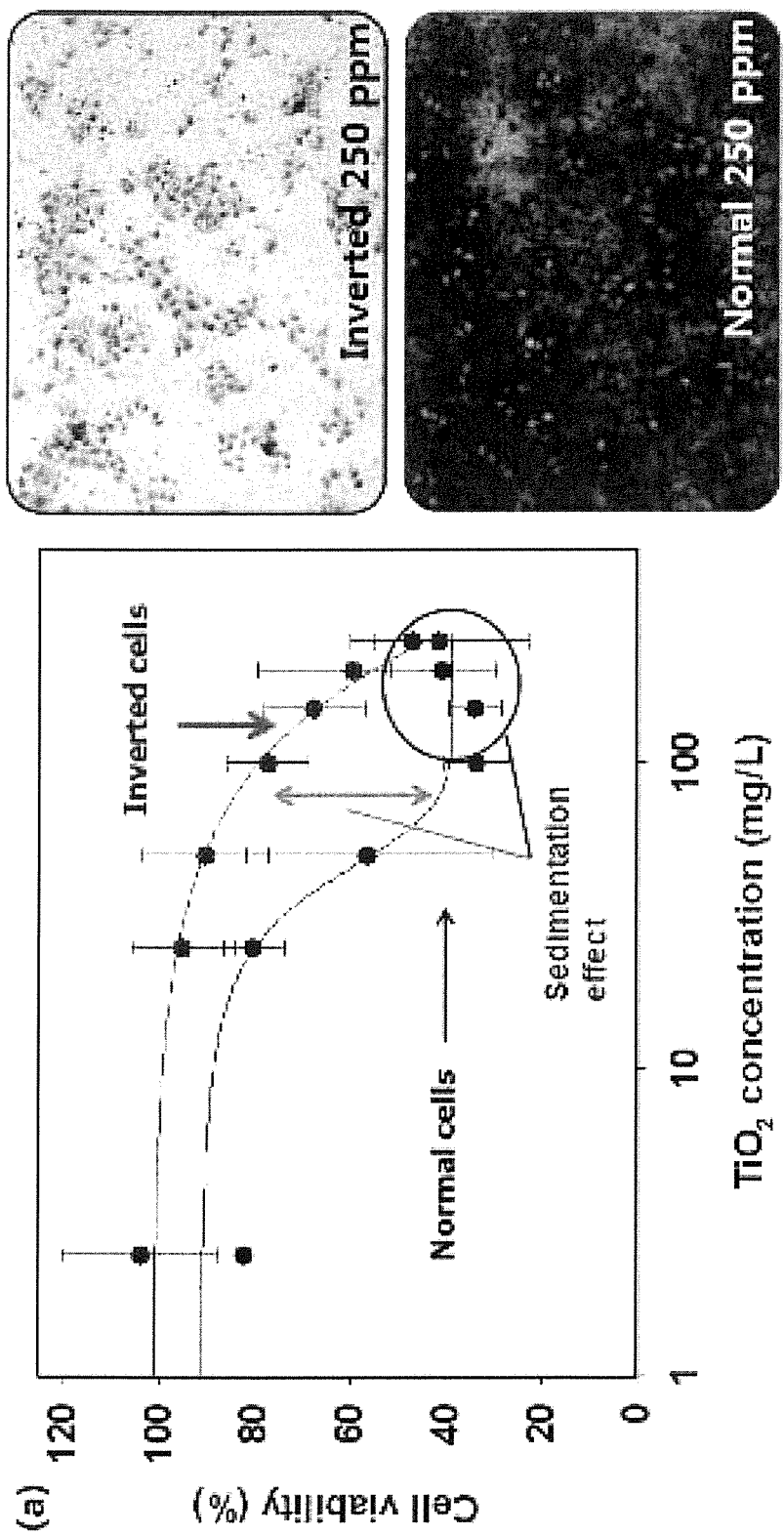
FIG. 24: graphs for cell viability according to the concentration of the titanium dioxide nano-particles exposed to a normal and inverted nano-material exposure apparatus.
Figure 24B:
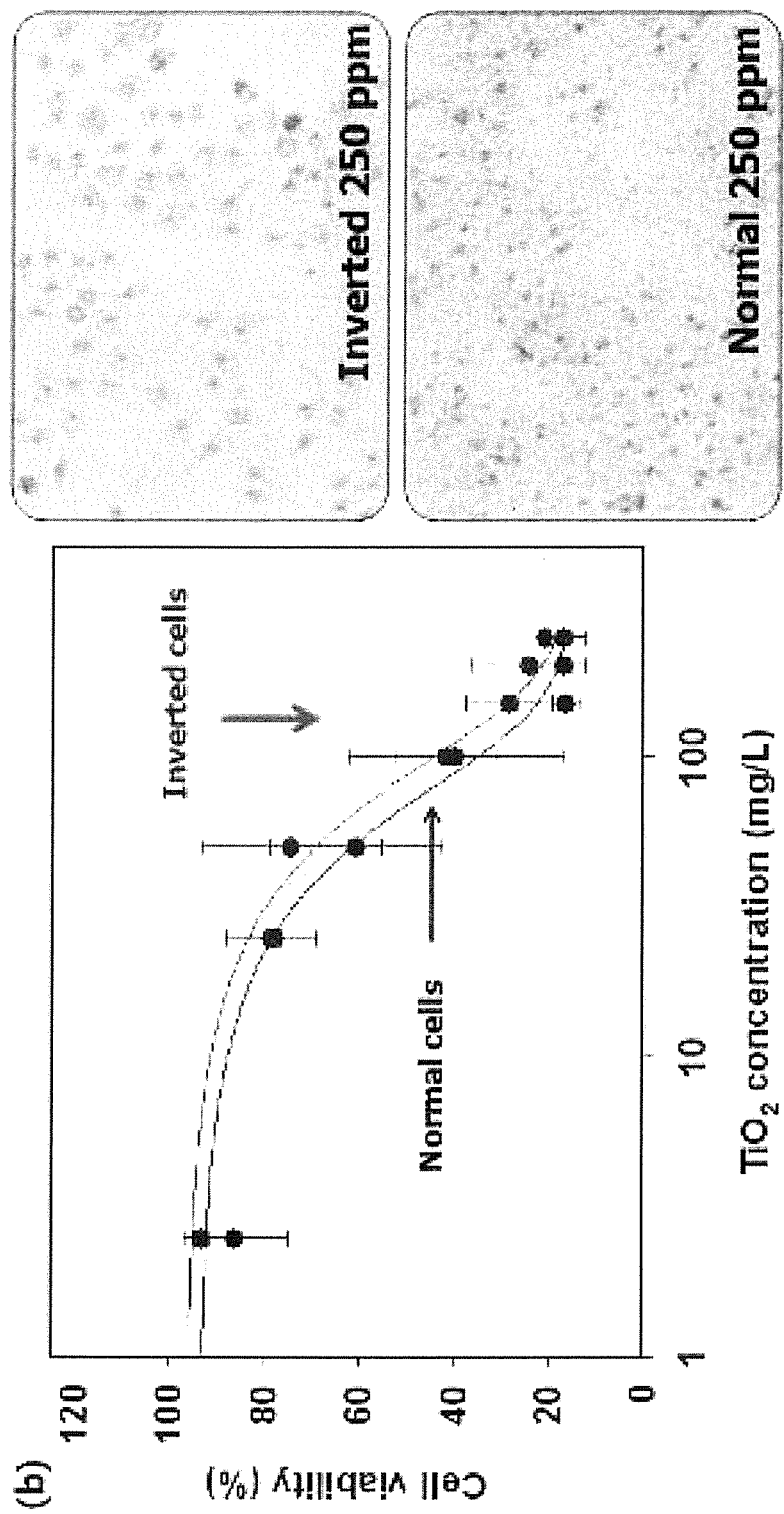

First of all, the cell viability according to the concentration of the titanium dioxide nano-particles exposed to the normal and inverted nano-material exposure apparatus was checked and is illustrated in FIG. 24. The graph of FIG. 24(a) is the result of the experiment using titanium dioxide nano-particles having 300 nm mean size in an aqueous solution, and the graph of FIG. 24(b) is the result of the experiment using titanium dioxide nano-particles having 700 nm mean size in an aqueous solution. In the result of (a), the toxicities of the normal cells and inverted cells were different from each other when the particles were sedimented because there were many large particles. Namely, the use of the inverted exposure apparatus is meaningful. However, in (b), the toxicities of the normal and inverted cells were not very different because there was little sedimentation. Namely, it was confirmed that the errors according to the cellular toxicity when the nano-materials were sedimented can be significantly reduced by a method of the present invention using the normal exposure apparatus with the inverted exposure apparatus. However, the error resulting from the scattering of the nano-particles themselves was found, although MTT formazan was not generated (FIG. 24(a)).

Therefore, the apoptosis reaction was measured using absorbance by analyzing images wherein the influence of the nano-particles was additionally removed by absorbance.

Figure 25:
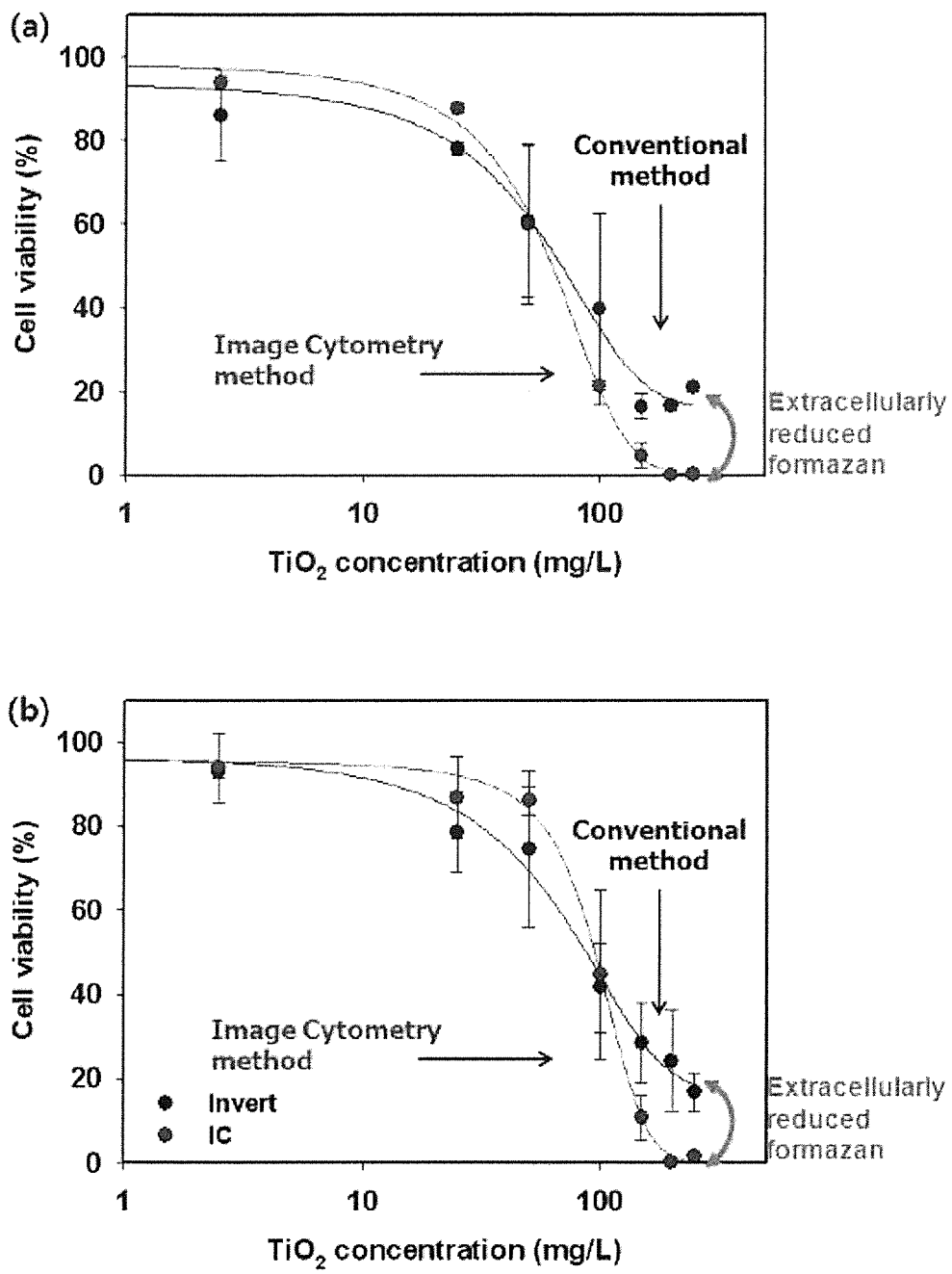
FIG. 25: graphs comparing apoptosis reaction by micro plate reader analysis and image cytometry removing the influence of the nano-particles.

FIG. 25 is a graph showing that error was generated from measuring absorbance by the nano-particles. FIG. 25(a) shows the result of comparing the result of apoptosis in the normal nano-material exposure apparatus with the result of apoptosis obtained from image cytometry, and (b) shows the result of comparing the result of apoptosis in the inverted nano-material exposure apparatus with the result of apoptosis obtained from image cytometry. Namely, it was confirmed that, as shown in FIG. 25, there is a difference between the result of using image cytometry and the result of the analysis using a microplate reader.

Therefore, by combining the above results, it can be confirmed that the errors of the existing apoptosis analysis method can be reduced using the inverted nano-material exposure apparatus, and in addition to, the errors caused by the scattering of the nano-particles themselves can be reduced by further analyzing the result of image cytometry. Thus, the effectiveness of each assessing method was confirmed, namely, it was confirmed that the dose characteristics of the nano-materials can be analyzed by the steps of the present invention, namely, by mSPIM, and the apoptosis analysis also can be more objectively analyzed than conventional methods. Therefore, it was expected that a more accurate toxicity assessment was achieved by combining the results of these two analyses, and the toxicities to the silica nano-materials and silver nano-materials were actually analyzed according to the present invention. In this case, image cytometry was used as a method to analyze the cellular responsiveness in the following experiments, but it is obvious to a skilled person in the art that the results also can be combined by a method using the normal•inverted exposure apparatus.

Example 2

Toxicity Assessment of Silica Nano-Materials

Figure 26:
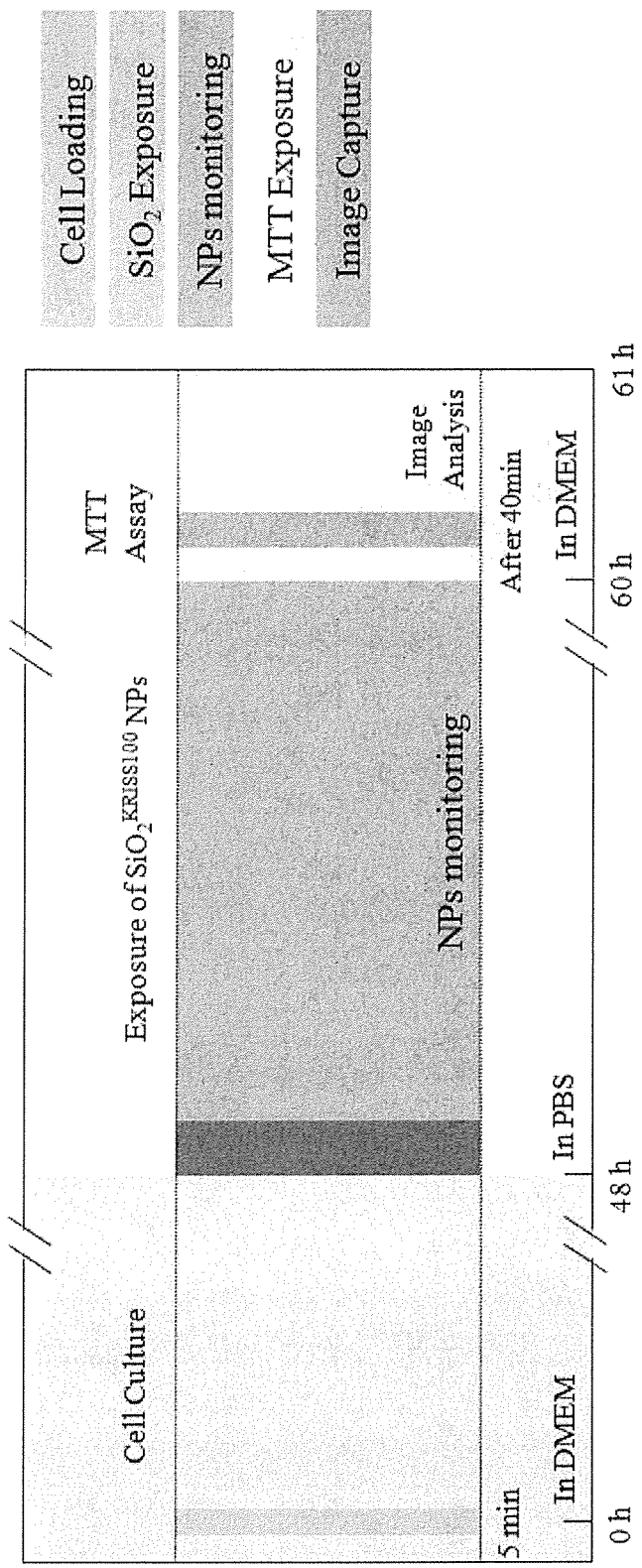
FIG. 26: a diagram of a method for assessing the characteristics of the silica nano-materials and measuring the cellular responsiveness sequentially according to the present invention.

A diagram of a system for sequentially assessing the dose characteristics and the cellular responsiveness of the silica nano-materials is illustrated in FIG. 26.

(1) mSPIM System

The laser light entering the sample was provided by a laser beam having a wide width (~250 um) and being thin (5 um) using an objective lens and cylindrical lens, and then irradiated to the side of the sample. Then, a microscope system was installed to observe the light scattered from the particles and the cells at the point where the irradiated laser beam and the focus coincided.

(2) Preparation of a Microfluidic Chip to Use mSPIM

A microfluidic chip was prepared to use the mSPIM system. As shown in FIG. 3 (a chip for sequentially assessing the characteristics and measuring the cellular responsiveness of the silica nano-materials), the microfluidic chip was produced by preparing a chip having a height of 3 mm using an upper mold, followed by attaching a top chip, which can link each section, to the top thereof.

(3) Cell Culture in the Chip for Using mSPIM

Cells were injected through a loading port in a cell culture channel. Because each section was linked to each other through a microchannel of the top chip, the cells were able to be injected only via the cell culture channel. After injecting the cells, the cells were stably cultured in a cell incubator with 5% $CO_2$ for 48 hours.

(4) Exposure of Nano-Particles and Observation of Nano-Particles

A solution prepared by adding the silica nano-particles of each concentration to PBS was injected into a microfluidic cell chip. Then, the chip was located in the mSPIM system, and laser was irradiated by the light sheet way to obtain images from the silica nano-particles using scattered light. The number and the size of the silica nano-particles were analyzed from the one hundred photos continuously taken.

(5) Measuring the number and the size of nano-particles through image analysis

The measurement was performed using the method suggested in Example 1. The silica nano-particles having the size of 100 nm were exposed, and then the number and the size thereof were analyzed.

The silica nano-particles were tracked from the images using an IDL program. Through the tracked silica nano-particles, the analysis was performed by the number of detected silica nano-particles per image, and the diffusion coefficient D of the silica nano-particles was obtained by mean-square-displacements (MSD), mean-square of the moving distance, of each Brownian movement particle. Then, the size of the tracked nano-particles was calculated by substituting MSD in the stoke-einstein formula.

Figure 27:
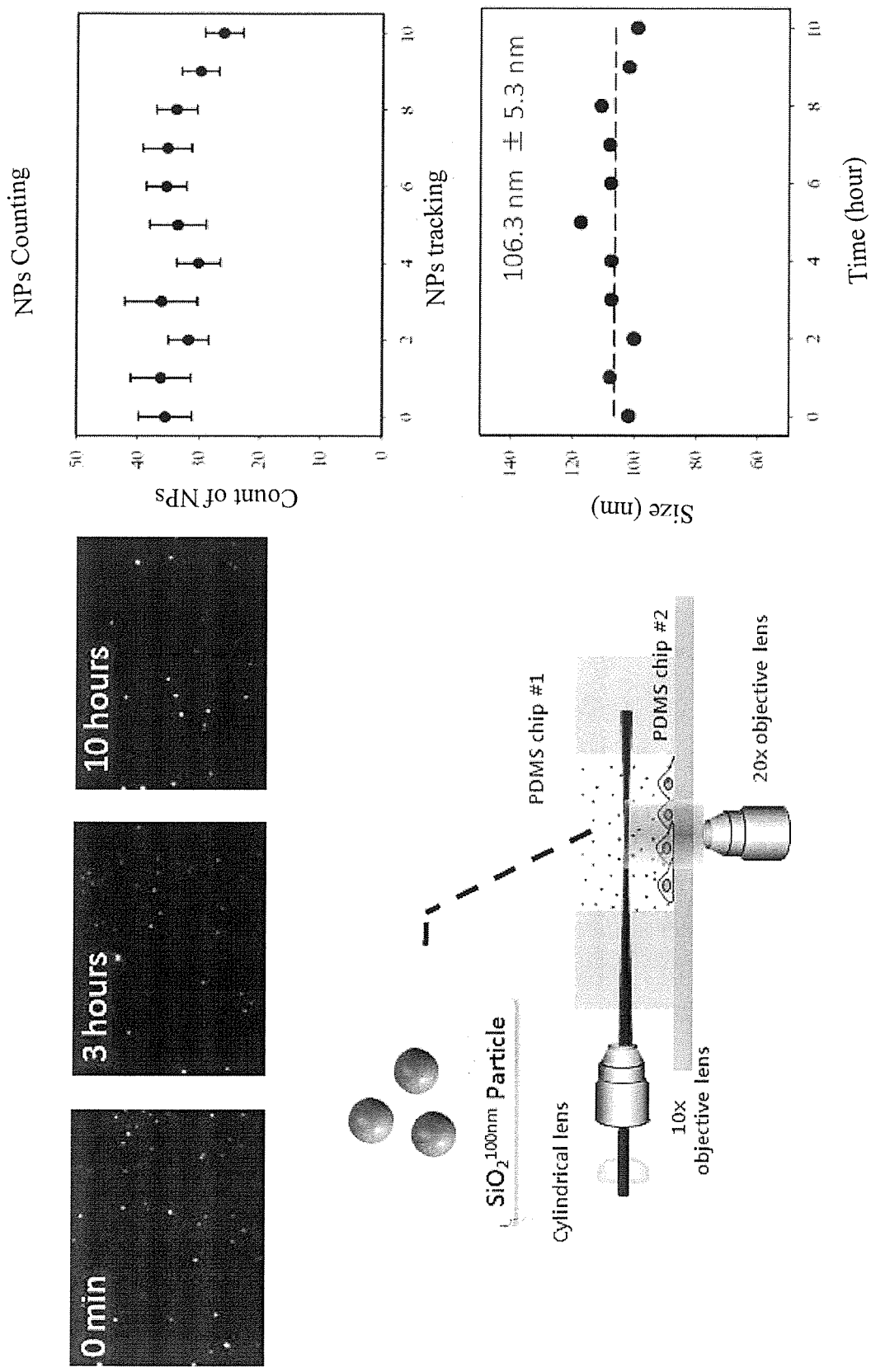
FIG. 27: images and graphs showing the change in the number (concentration) and the size of the silica nano-particles.
Figure 28A:
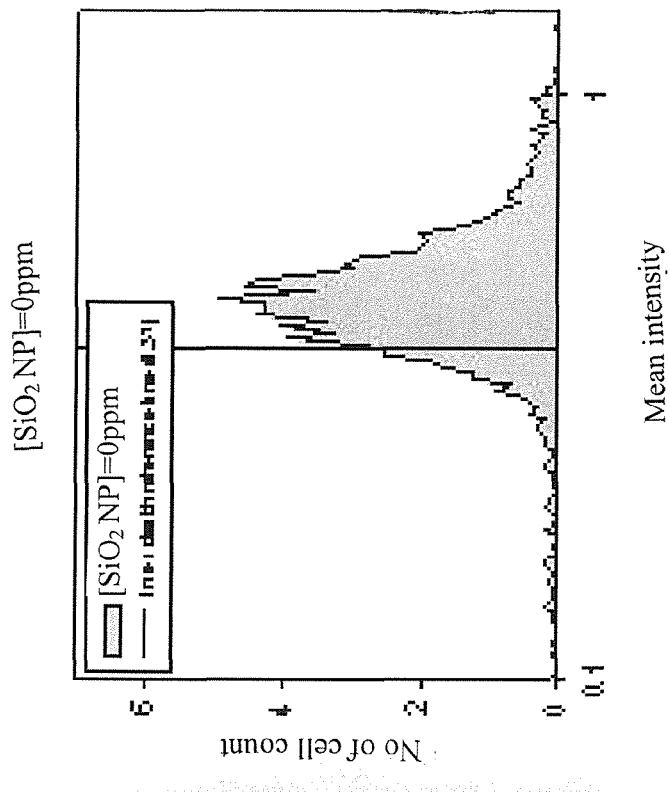
FIG. 28: cell images, histograms and scatter diagrams for the cellular responsiveness assessment to the silica nano-particles.
Figure 28A:
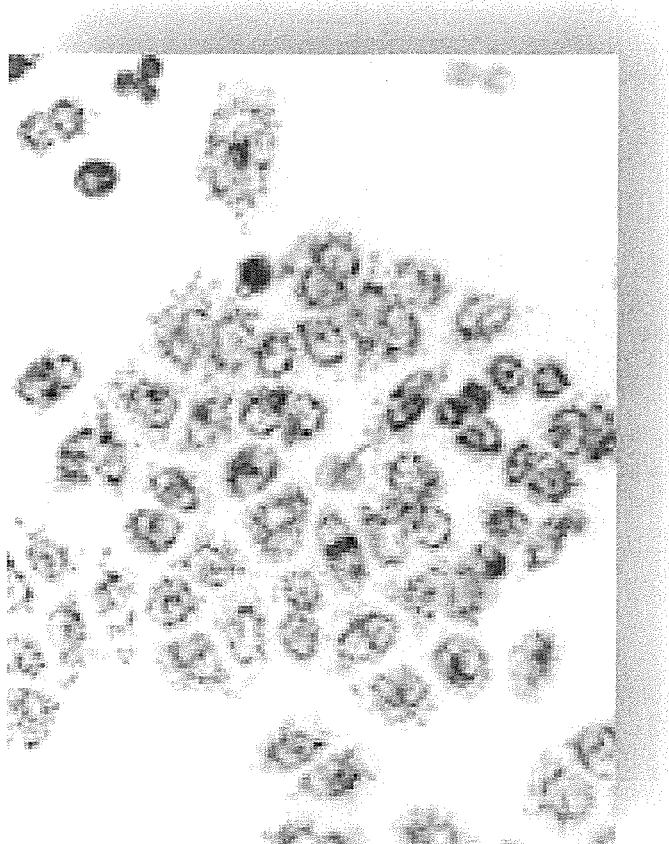
Figure 28B:
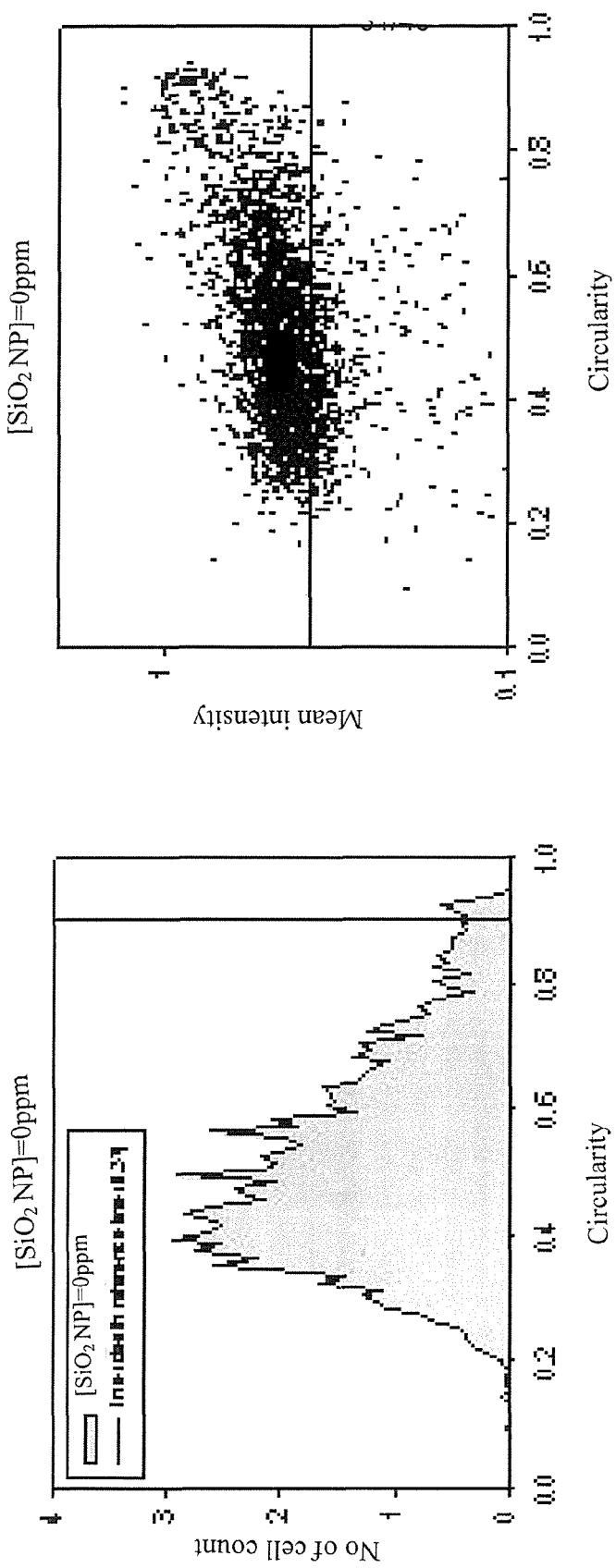
Figure 28C:
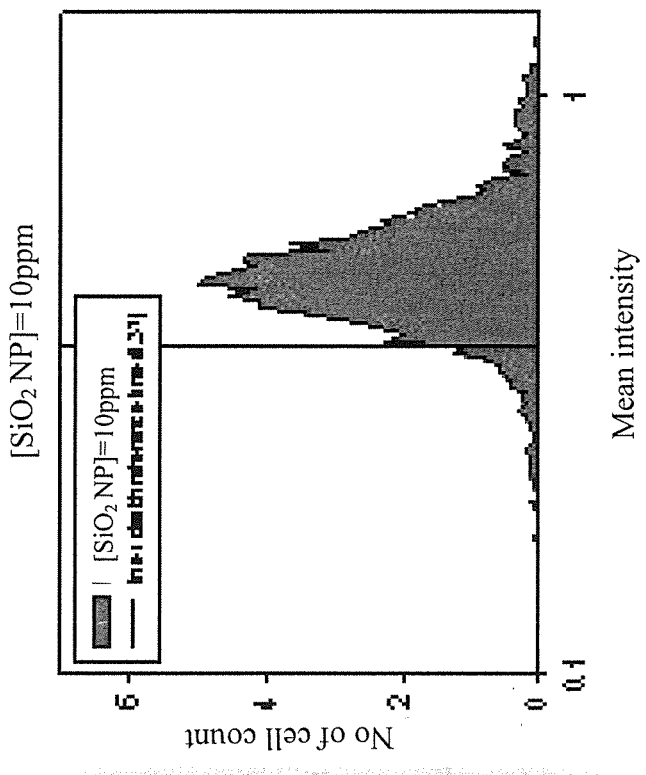
Figure 28C:
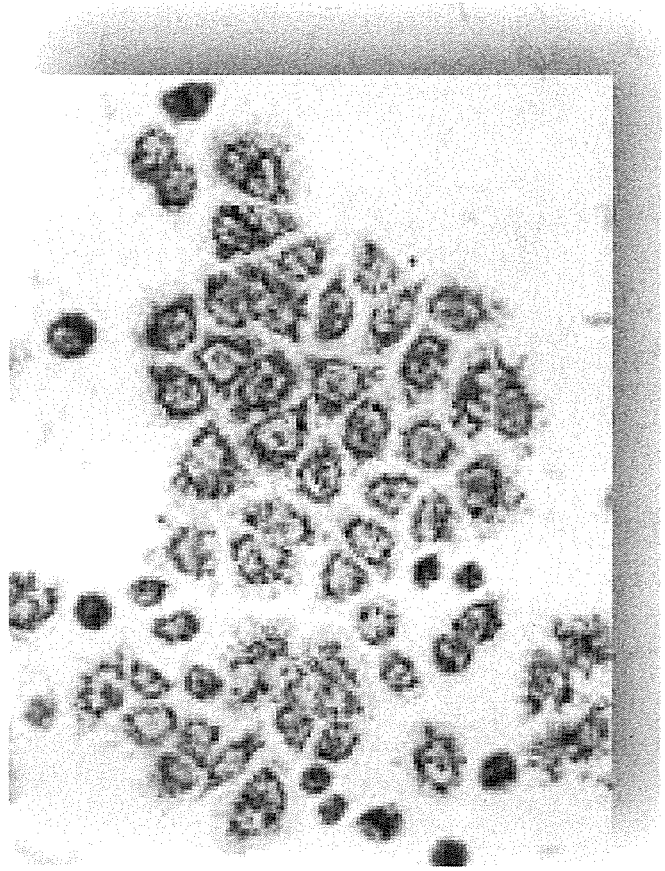
Figure 28D:
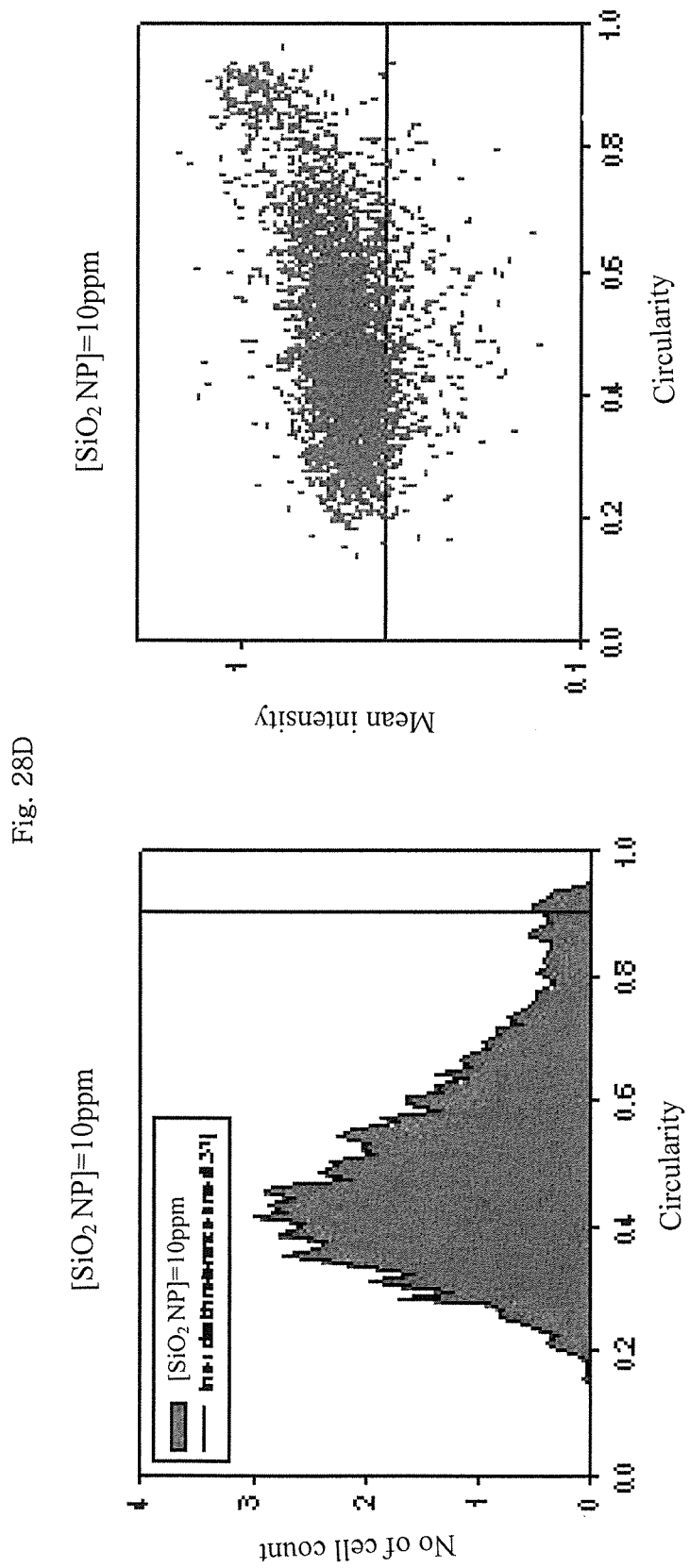
Figure 28E:
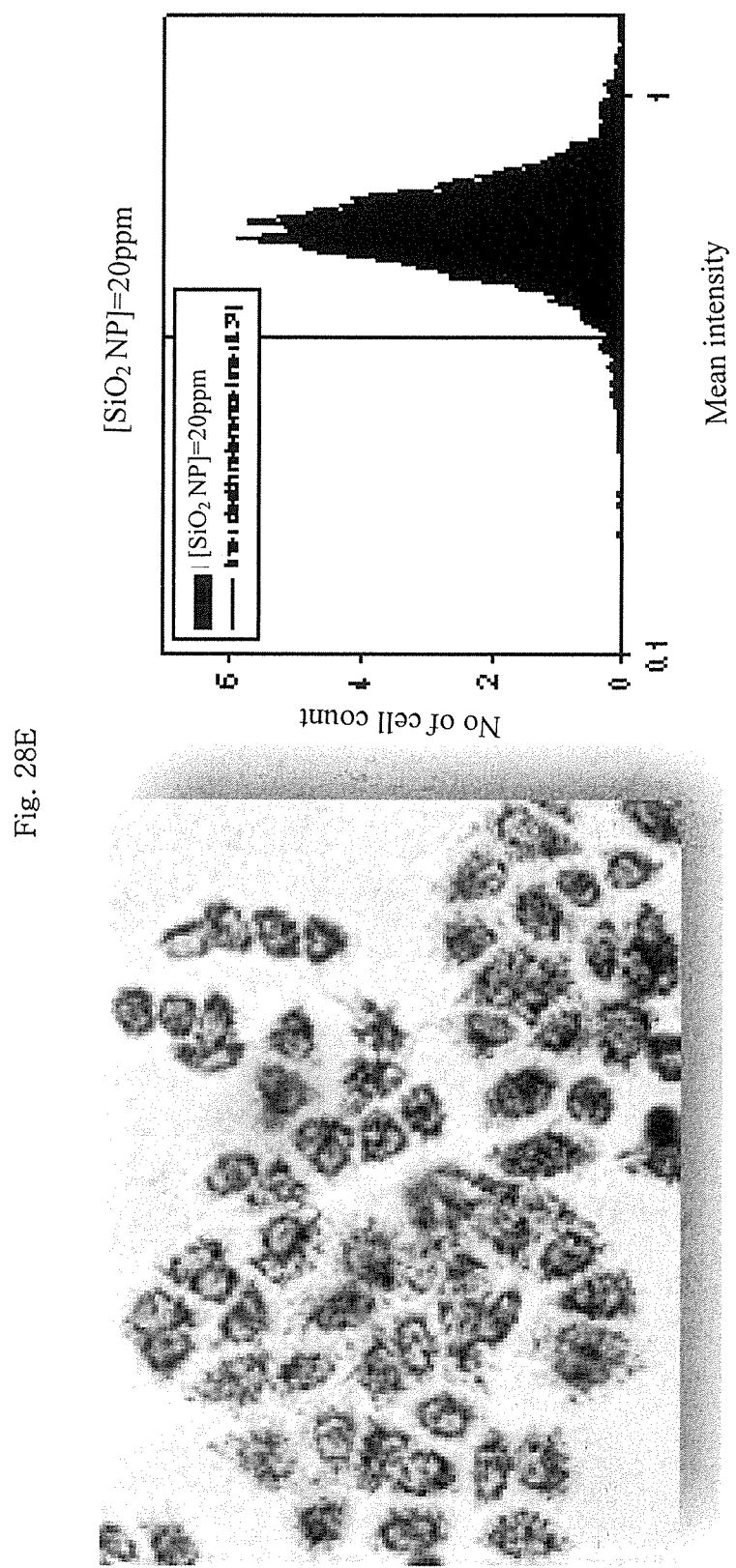
Figure 28F:
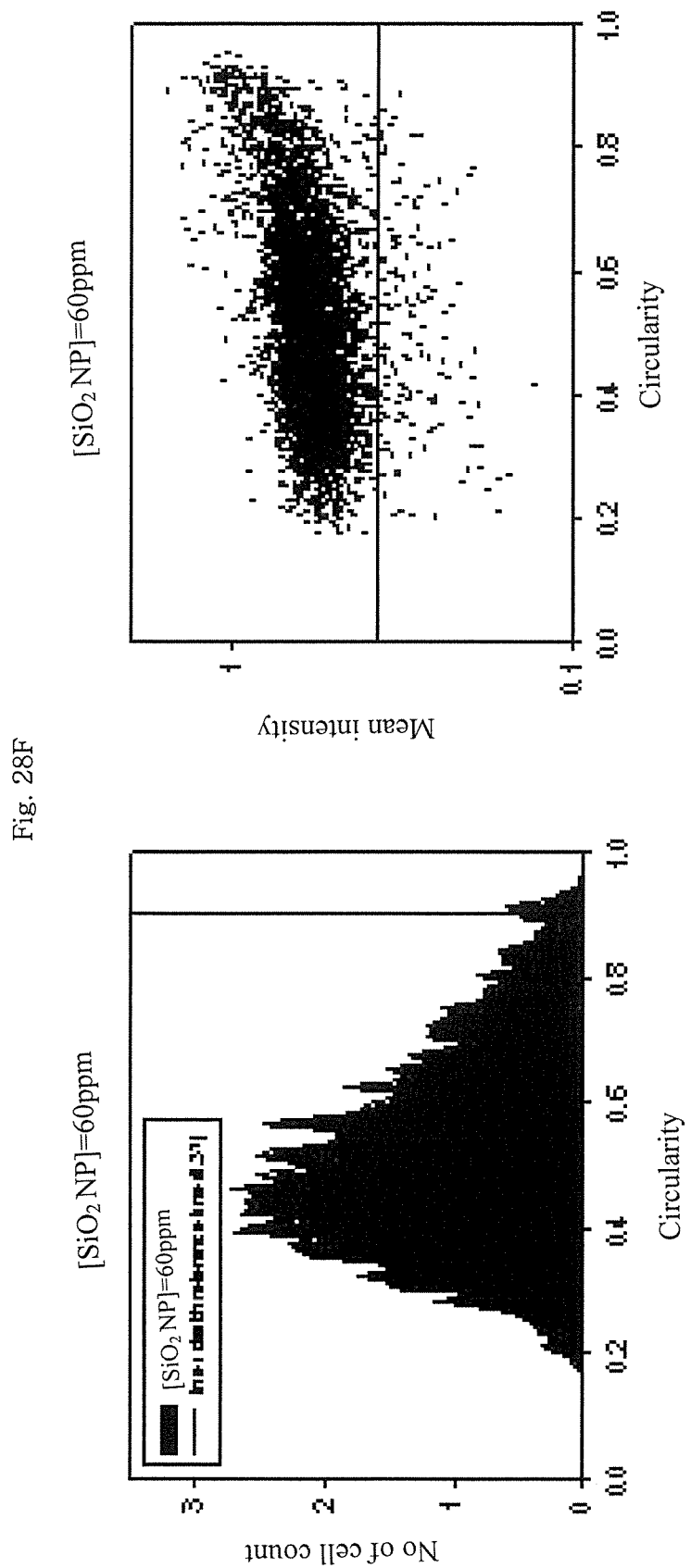

Consequently, as shown in FIG. 27, the changes in the number (concentration) and the size of the silica nano-particles over time were observed. As shown in FIG. 27, it was confirmed that the size of the silica nano-particles in the cell culture solution was maintained to about 106 nm after exposure due to their stability, and the particle number was little reduced. Further, it was realized that the characteristics of the silica nano-particles in the cell culture solution were maintained.

(6) Cellular Responsiveness Analysis

In order to analyze the responsiveness of the cells exposed to the silica nano-particles for 10 hours, absorption analysis (modified MTT assay) was performed. The cells exposed to the MTT solution did not form purple formazan according to the degree of apoptosis, and the absorption image of the cells was analyzed using this fact. Through image analysis, the absorbance and circularity factors per cell were determined.

Consequently, as shown in FIG. 28, the cellular responsiveness suggested in cell images, histograms and scatter diagrams was analyzed.

Then, it was observed that the degree of the MTT formazan production of the cells exposed to the silica nano-particles by the modified MTT assay was not changed even when the concentration increased, and the circularity remained constant. Therefore, it was quantitatively determined by the scatter diagrams that the cells did not die.

Example 3

Toxicity Assessment of Silver Nano-Materials

The sequential assessments of the dose characteristics and the cellular responsiveness analysis of silver (Ag) nano-materials were performed by an almost identical method to that of the silica nano-materials in Example 2.

First of all, silver nano-particles measuring 11 nm were exposed using mSPIM system, and then the number and the size of the nano-particles were analyzed.

Figure 29:
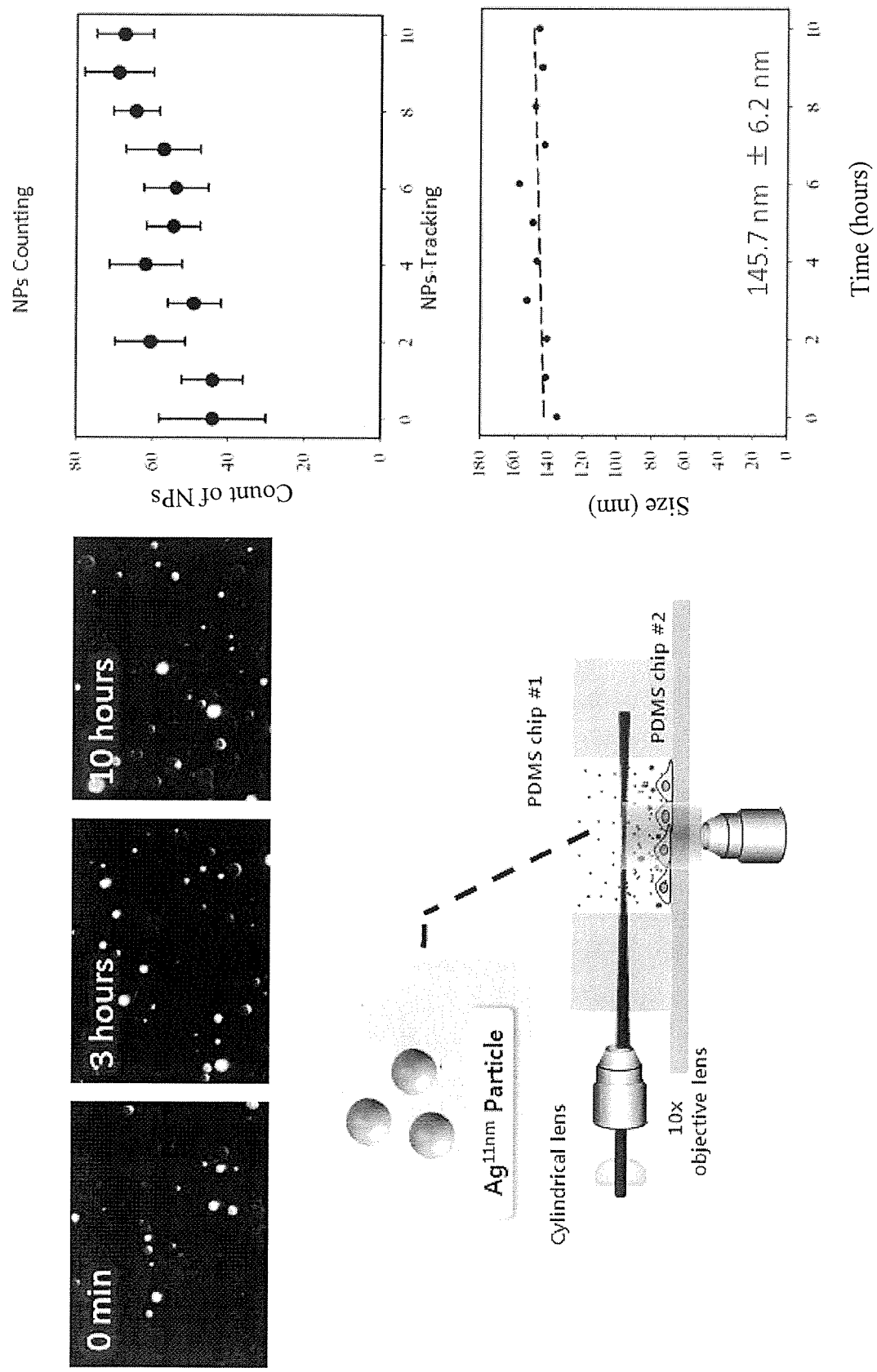
FIG. 29: images and graphs showing the change in the number (concentration) and the size of the nano-particles.
Figure 30A:
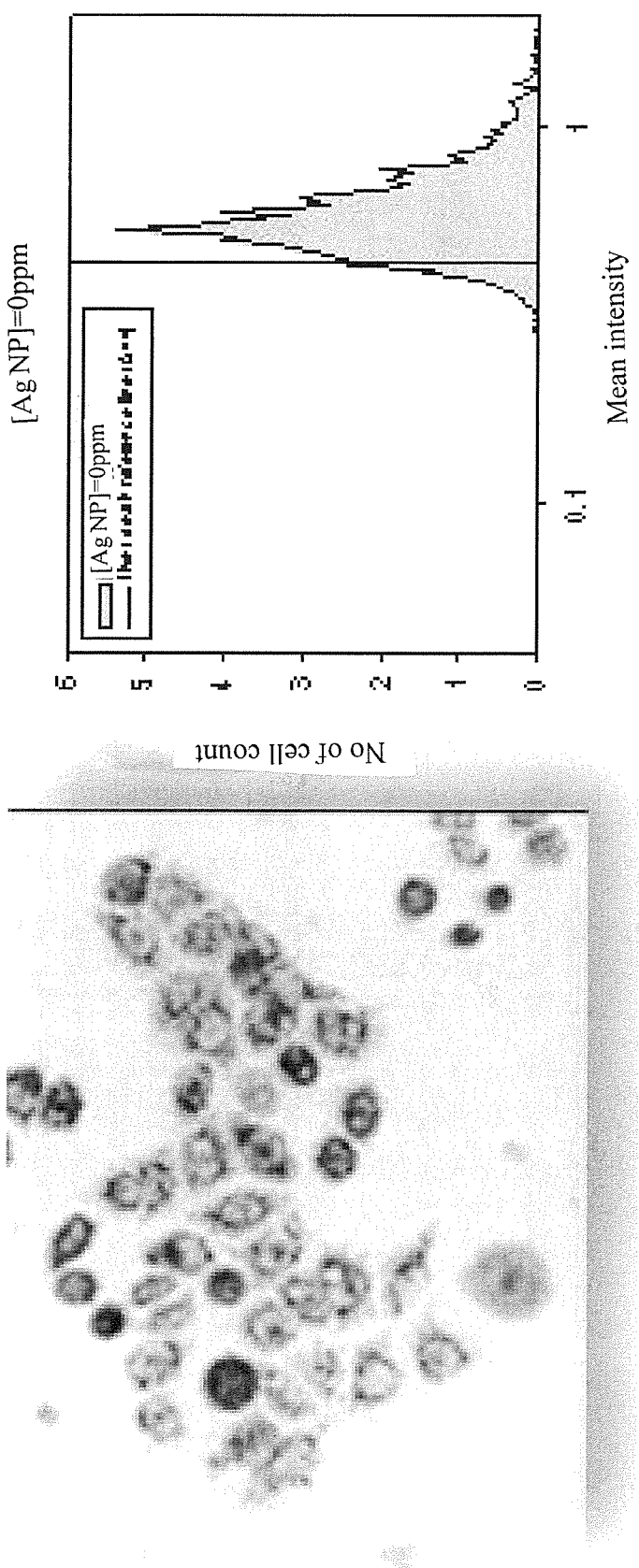
FIG. 30: cell images, histograms and scatter diagrams for the cellular responsiveness assessment to the nano-particles.
Figure 30B:
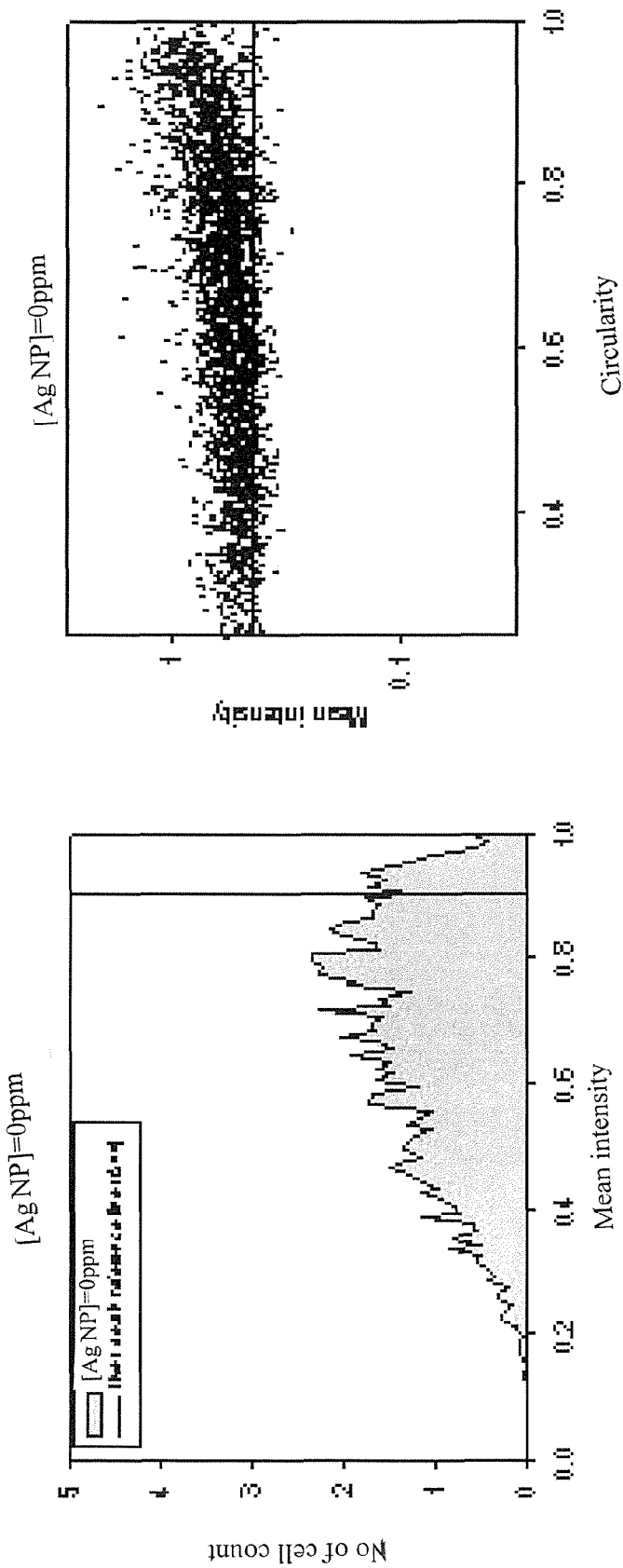
Figure 30C:
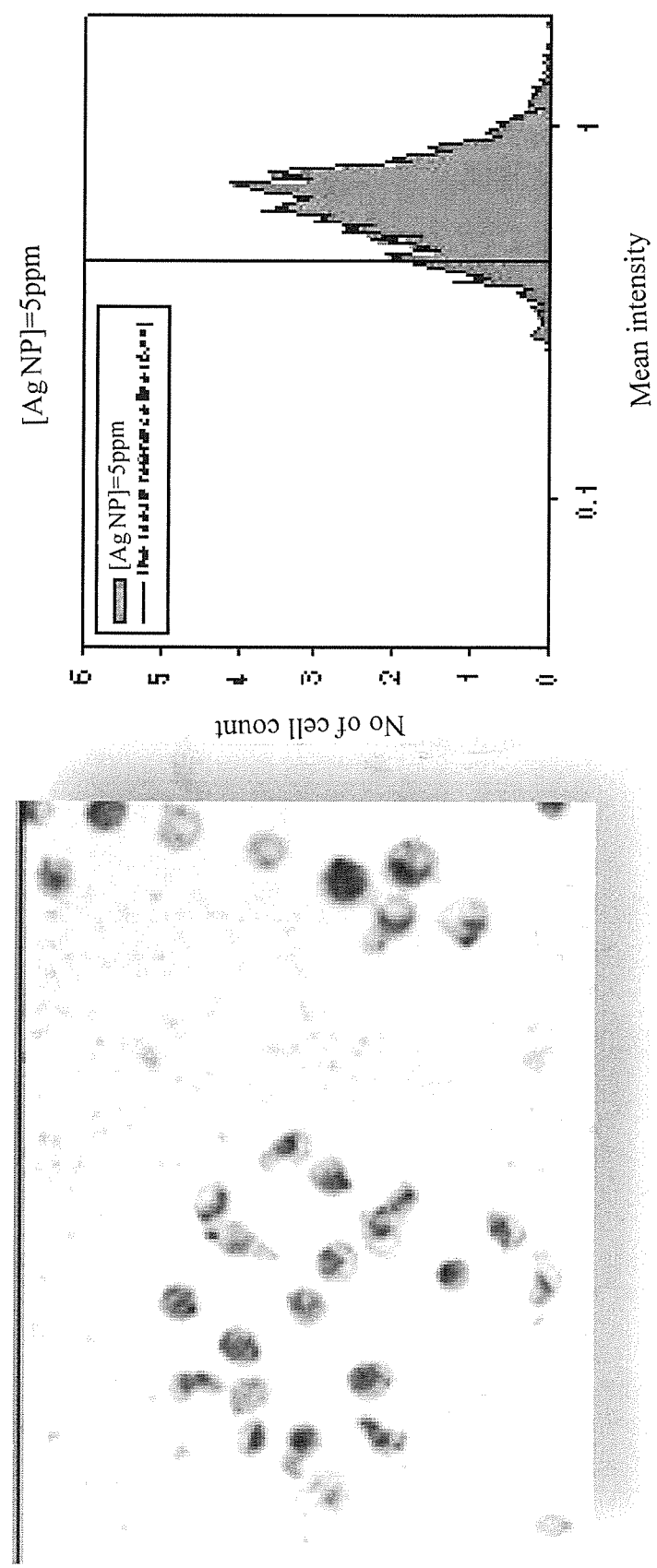
Figure 30D:
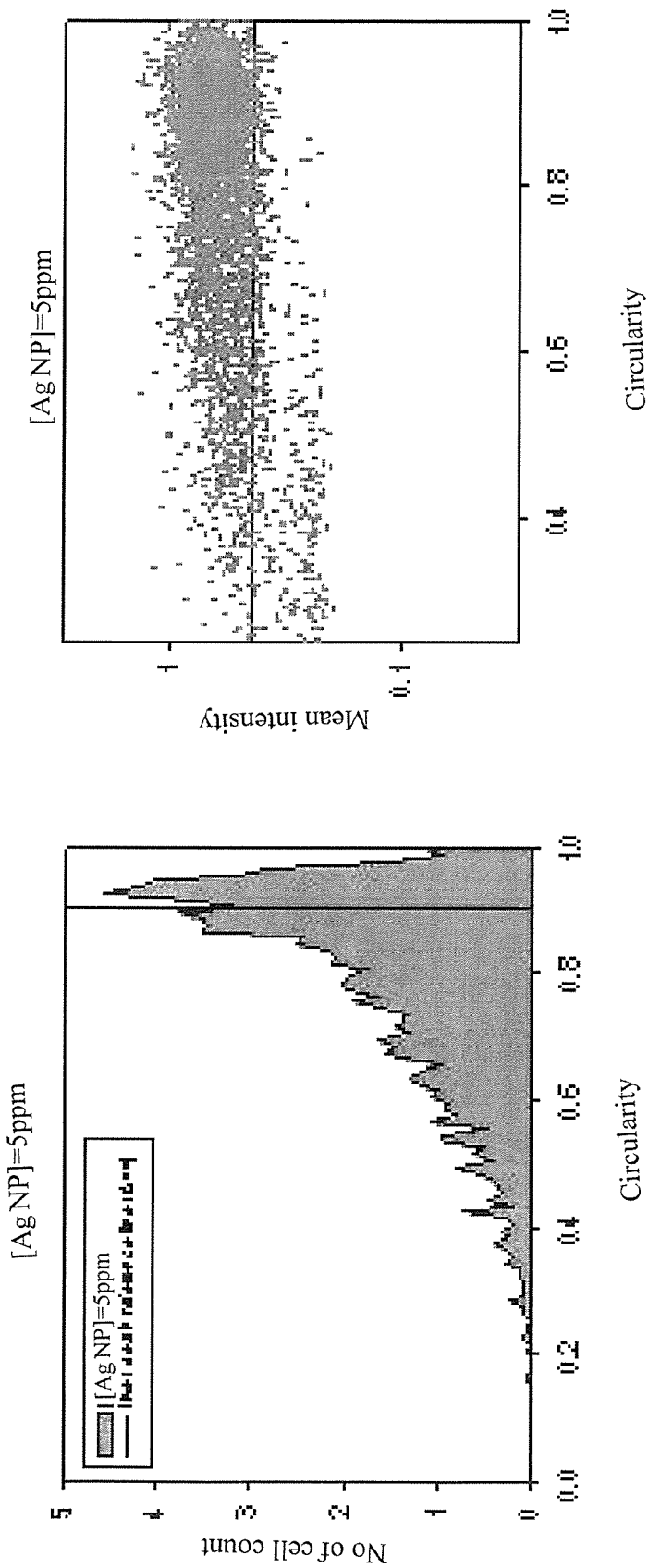
Figure 30E:
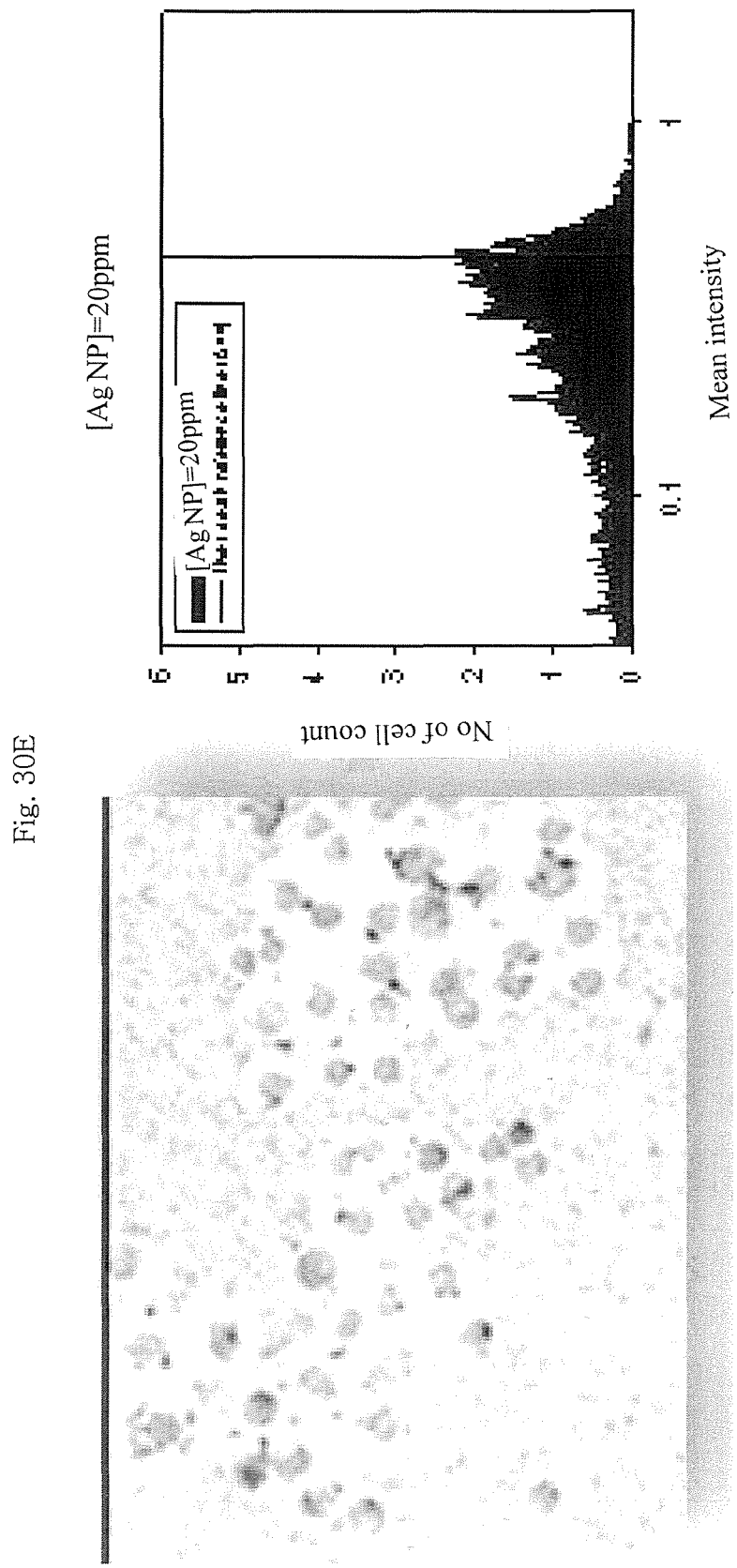
Figure 30F:
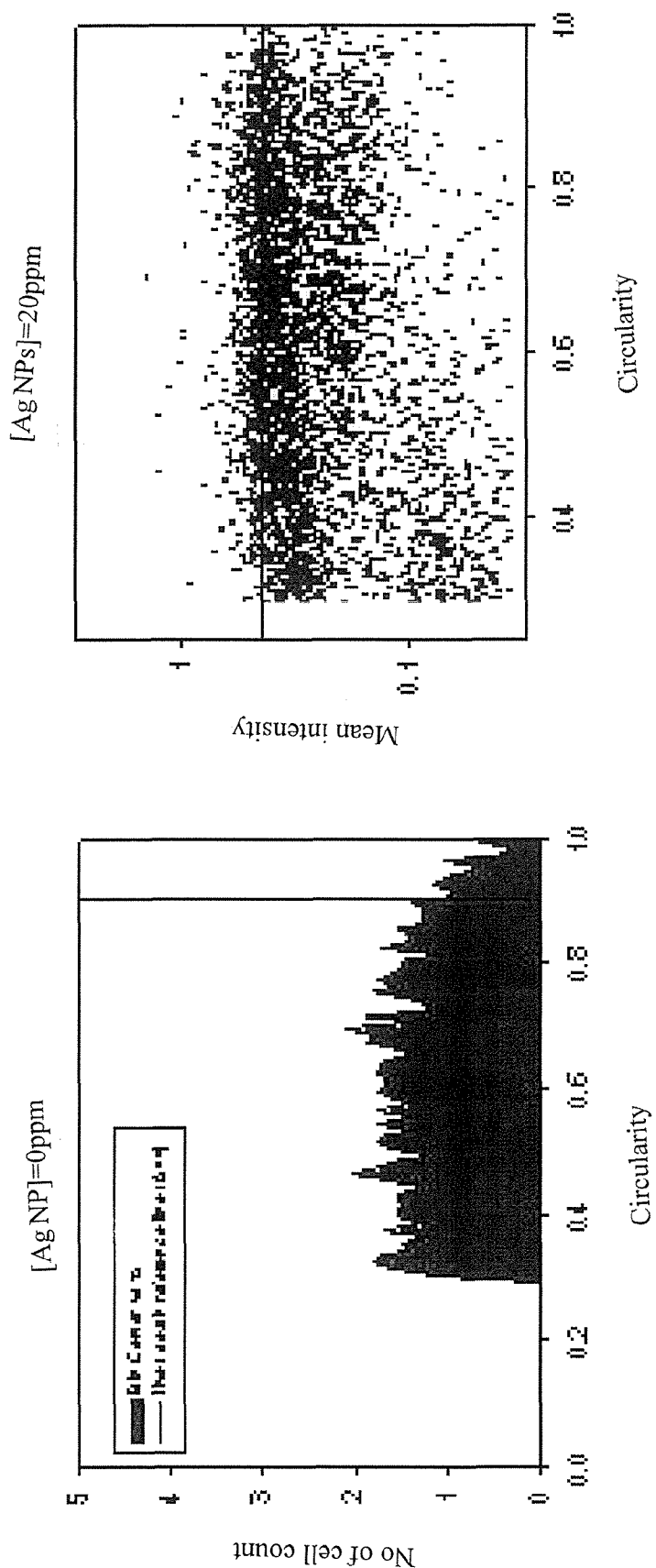

The results are illustrated in FIGS. 29 and 30. The changes in the number (concentration) and the size of the silver nano-particles over time are illustrated above, and the cellular responsiveness as suggested in cell images, histograms and scatter diagrams is illustrated.

As shown in FIG. 29, it was confirmed that the size of the silver nano-particles in the cell culture solution increased to about 145 nm right after exposure due to their instability, and the number thereof increased. It was realized that the characteristics of the silver nano-particles in the cell culture solution was changed, and then, it was observed that the production of the MTT formazan of cells exposed to the silver nano-particles decreased with the increased concentration, and the circularity increased and then decreased in the modified MTT assay. Therefore, apoptosis could be quantitatively analyzed through scatter diagrams (FIG. 30).

What is claimed is:

1. A method for toxicity assessment of nano-materials comprising:
   exposing the nano-materials to a cell medium including cells;
   analyzing dosimetry of the nano-materials using Selective Multi-Plane Illumination Microscopy (mSPIM), and
   analyzing cellular responses to the nano-materials using a normal and inverted exposure apparatus.

2. The method for the toxicity assessment of nano-materials of claim 1, further comprising conducting image cytometry.

3. The method for the toxicity assessment of nano-materials of claim 1, wherein the normal and inverted exposure apparatus comprises a microfluidic chip.

4. The method for the toxicity assessment of nano-materials of claim 1, wherein the normal and inverted exposure apparatus is installed to expose a cultured cell layer to the nano-materials by orienting the cultured cell layer face up to measure cellular responses caused by both active and passive intake of nano-materials in a normal exposure mode, or by orienting the cultured cell layer face down to measure cellular responses caused only by active intake of the nano-materials in an inverted exposure mode, the normal and inverted exposure apparatus used for effective dose correction of the nano-materials.

5. The method for the toxicity assessment of nano-materials of claim 2, wherein the image cytometry is conducted by a method selected from a group consisting of an absorption method and fluorescence method.

6. The method for the toxicity assessment of nano-materials of claim 5, wherein
   the absorption method is conducted by using an absorption dye selected from a group consisting of: MTT (3-(4,5-dimethyl thiazol-2-yl)-2,5-diphenyl tetrazolium bromide)), MTS (5-(3-caroboxymethoxyphenyl)-2H-tetrazolium inner salt), WST (4-[3-(4-Iodophenyl)-2(4-nitrophenyl)-2H-5-tetrazolio]1,3-benzene disulfonate) and trypan blue.

7. The method for the toxicity assessment of nano-materials of claim 6, wherein cell image analysis is conducted by obtaining a bright field cellular image with an MTT formazan absorbance.

8. The method for the toxicity assessment of nano-materials of claim 5, wherein
   the fluorescence method is conducted by using an organic fluorescent dye or a fluorescent protein.

9. A method of toxicity assessment of nano-materials comprising:
   exposing the nano-materials to a cell medium including cells;
   measuring the concentration and the size distribution of the nano-materials dispersed in the cell medium using Selective Multi-Plane Illumination Microscopy (mSPIM);
   measuring the change in concentration and size distribution over time using mSPIM and calculating the agglomeration and sedimentation coefficients of the nano-materials in the cell medium;
   measuring the concentration and hydrodynamic size distribution of the nano-materials accumulated in the cells after exposure to the cell medium using mSPIM and calculating the cellular uptake of the nano-materials in the cells;
   inducing crystal formation or cell staining by injection of absorption dyes in cells exposed to the nano-materials to show apoptosis;
   taking images of the cells over time to show the progress of apoptosis; and
   determining the degree of apoptosis from the images by calculating a value based on the group consisting of occupied area per cell, circularity, fluorescent intensity, and absorbance per cell.

* * * * *